US005756312A

United States Patent [19]

Weiner et al.

[11] Patent Number: 5,756,312

[45] Date of Patent: May 26, 1998

[54] IMMUNOREACTIVE POLYPEPTIDE COMPOSITIONS

[75] Inventors: Amy J. Weiner, Benicia; Michael Houghton, Danville, both of Calif.

[73] Assignee: Chiron Corporation, Emeryville, Calif.

[21] Appl. No.: 231,368

[22] Filed: Apr. 19, 1994

Related U.S. Application Data

[63] Continuation of Ser. No. 759,575, Sep. 13, 1991.

[51] Int. Cl.$^6$ .......................... C12N 15/51; A61K 39/29; C12Q 1/70; C07K 14/18

[52] U.S. Cl. ..................... 435/69.3; 435/172.3; 435/325; 424/184.1; 424/185.1; 424/189.1; 424/192.1; 424/204.1; 424/228.1; 536/23.72; 536/23.4; 530/350; 530/826

[58] Field of Search ............................. 424/184.1, 185.1, 424/192.1, 204.1, 228.1, 189.1; 435/69.3, 172.3, 325; 530/350, 826; 536/23.72, 23.4

[56] References Cited

U.S. PATENT DOCUMENTS 5,372,928 12/1994 Miyamura et al. .......................... 435/5

FOREIGN PATENT DOCUMENTS

| | | |
|---|---|---|
| 0318216 | 5/1989 | European Pat. Off. . |
| 318216 | 5/1989 | European Pat. Off. . |
| 0388232 | 9/1990 | European Pat. Off. . |
| 0 149 182 A1 | 3/1991 | European Pat. Off. . |
| 8904669 | 6/1989 | WIPO . |
| 9011089 | 10/1990 | WIPO . |
| 9014436 | 11/1990 | WIPO . |

OTHER PUBLICATIONS

Neurath, A.R. et al. (90) Mol. Immunol. 27:539–549.

Haigwood, N.L. et al (90) AIDS Res. and Hum. Retrovir. 6:855–869.

Goodenow, M., et al., "HIV-1 isolates are rapidly evolving quasispecies: Evidence for viral mixtures and preferred nucleotide substitutions" *Journal of Acquired Immune Deficiency Syndromes* (1989) 2(4):344–352.

Weiner et al., "Variable and hypervariable domains are found in the regions of HCV corresponding to the flavivirus envelope and NS1 proteins and the pestivirus envelope glycoproteins" *Virology* (1991) 180:842–848.

Weiner et al., "Evidence for immune selection of hepatitis C virus (HCV) putative envelope glycoprotein variants: potential role in chronic HCV infections" *Proc. Natl. Acad. Sci. USA* (1992) 89:3468–3472.

Okamoto et al., "Nucleotide sequence of the genomic RNA of hepatitis C virus isolated from a human carrier: comparison with reported isolates for conserved and divergent regions" *Journal of General Virology* (1991) 72(11):2697–2704.

Kremsdorf et al., "Partial nucleotide sequence analysis of a French hepatits C virus: implications for HCV genetic variability in the E2/NS1 protein" *Journal of General Virology* (1991) 72:2557–2561.

Kubo et al., 1989, *Japan Nucl. Acids Res 17*(24):10367–10372.

Choo et al. 1990, *Brit. Med. Bull. 46*:423–442.

Kato et al., 1990, *Proc. Natl. Acad. Sci. USA 87*:9524–9528.

Takeuchi et al., 1990, *Gene 91*:287–291.

Takeuchi et al., 1990, *J. Gen. Virol. 71*:3027–3033.

Takeuchi et al., 1990, *Nucl. Acids Res. 18*(15):4626.

Choo et al., 1991, *Proc. Natl. Acad. Sci. USA 88*:2451–2455.

Han et al., 1991, *Proc. Natl. Acad. Sci. USA 88*:2451–2455.

Okamoto et al., 1991, *Japan J. Exp. Med. 60*(3):167–177.

Takamizawa et al., 1991, *J. Virol. 65*:1105–1113.

Weiner et al., 1991, *Virol. 180*:842–848.

Houghton et al., 1991, *Hepatology 14*(2):381–388.

*Primary Examiner*—Michael P. Woodward
*Attorney, Agent, or Firm*—Alisa A. Harbin; Susan A. Wolffe; Robert P. Blackburn

[57] ABSTRACT

This invention relates generally to immunoreactive polypeptide compositions comprising hepatitis type C viral epitopes, methods of using the compositions in immunological applications, and materials and methods for making the compositions.

8 Claims, 32 Drawing Sheets

```
HCV-1   192  YQVRNSTGLYHVTNDCPNSSIVYEAADAILHTPGCVPC
HCT18        H-------------------------------------
Th           -------------------------------A------
HCT23        -------------------------------A------
HCT27        ------S-I---------------T--T---S------
HC-J1        -------------------------H------------
              *   *          *       * *
HC-J4        -E---VS-I-------S-------M-M-----------
HCV-J        -E---VS-I-------S-------M-M-----------
HCV J1       -E---VS-I-------S-------V-M-A---------
BK           -E-H-VS-I-------S-A-----L-M-----------

HCV-1   230  VREGNASRCWVAMTPTVATRDGKLPATQLRRHIDLLVGSATLCSALYVGDLCGSVFLVGQ
HCT18        -H---V------V------------T----------------------------------
Th           ------------------A---R--T----------------------------I-----
HCT23        ---D-V------V------K-----T----------------------------I-----
HCT27        -------K---PVA--------N-------------------------------------
HC-J1        -----V---------------------------------------------------I--
                  *      *   *   **** *      *     * *    *            *
HC-J4        ---D-S------L---L-A-NASV-T-TI---V-----A-AF---M------------S-
HCV-J        ---S-F------L---L-A-NSSI-T-TI---V-----A-A----M------------S-
HCV J1       ---N-S------L---L-A-NASV-T-T----V-----T-AF---M-----------IS-
BK           -----S------L---L-A-NVTI-T-TI---V-----A-AF---M------------S-

HCV-1   290  LFTFSPRRHWTTQGCNCSIYPGHITGHRMAWDMMMNWSPTTALVMAQLLRIPQAILDMIA
HCT18        ----------------------------------------A--------------M----
Th           --------------------------------------------V---------------
HCT23        -------------D--------------------------A---V---------------
HCT27        -------------D--------------------------A-------------------
HC-J1        ----------------------------------------A-------------------
                      * *           **                    *        *   *
HC-J4        ---------E-V-D---------LS-------------------VS--------VV--V-
HCV-J        --------YE-V-D---------VS-------------------VS--------VV--V-
HCV J1       ---------E-V-D---------VS---------------A---VS--------VM--V-
BK           ---------V-L-D---------VS-------------------VS--------VV--V-
```

FIG. 2A

```
HCV-1     350    GAHWGVLAGIAYFSMVGNWAKVLVVLLLFAGVDA
HCT18            ----------------------------------
Th               ----------------------------------
HCT23            ---------M------------------------
HCT27            ----------------------------------
HC-J1            ----------------------------------
                          *  *        * *          *
HC-J4            ---------L--Y--------I-A----------G
HCV-J            ---------L--Y--------I-M----------G
HCV J1           ---------L--Y--------I-M----------G
BK               ---------L--Y--A-----I-M----------G
```

FIG. 2B

Comparative Amino Acid Sequence of the Putative E2/NS1 Region of HCV Isolates

```
HCV-1    370    KVLVVLLLFAGVDAETHVTGGSAGHTVSGFVSLLAPGAKQNVQLINTNGSWHLNSTALNC
HCT27           --------------T-YT---N-AR-TQALT-FFS-----DI----------I-R-----
HCVE1           ---L------------YT----TAR-TQ-L---FSR----DI----------I-R-----
H77             ------------------------R-TA-L-G--T------I----------I-------
H90             ------------------------RS-L-IA-F-TR-P---I---K------I-------
Th              ----------------T------A-GAL-IA--FNQ--R--I----------I-------
HC-J1           ----------------I-S--Q-ARAM--L---FT------I----------I-------
HC-J4           ---I-A-------G--YTS--A-S--T-TLA--FS---S-RI--V-------I-R-----
HCV-J           ---I-M-------GH------RVASSTQSL--W-SQ-PS-KI--V-------I-R-----
JH-1            ---I-M-------GH-R----VQ--VT-TLT--FR---S-KI--V-------I-R-----
BK              ---I-M-------GD------AQAK-TNRL--MF-S-PS-KI----------I-R-----

HCV-1    430    NDSLNTGWLAGLFYHHKFNSSGCPERLASCRPLTDFDQGWGPISYANGSGPDQRPYCWHY
HCT27           -G--D---V-----Y-----------M------A--Q--------------EH-------
HCVE1           -E--D---V-----Y-----------M------A--------------T--EH-------
H77             -E-----------------------------R----A-------------L-E-------
H90             -----A--I-------G--------------R--------------------E-------
Th       ****   ----h---I-----Y---------------------------------------------
HC-J1           -E----------I-Q----------------R------------H---------------
HC-J4           ----H--F--A---T-R---------M-----IDW-A------T-TEPDS----------
HCV-J           ----Q--FI-A---A-R--A------M-----IDE-A------THDMPESS---------
JH-1            ----Q--F--A---T----A------M----SIDK--------T--QPDNS---------
BK              ----Q--F--A---T-S---------M-Q--TIDK--------T--ES-RS---------

HCV-1    490    PPKPCGIVPAKSVCGPVYCFTPSPVVVGTTDRSGAPTYSWGENDTDVFVLNNTRPPLGNW
HCT27           ----------QN------------------NKL-----N--S-E----------------
HCVE1           ----------QT------------------NKL-----N--C------------------
H77             --R--------------------------------------A------------------
H90             --R-----------------------------------N--------LI-----------
Th              --------------------------------------N--A------------------
HC-J1           ------------------------
HC-J4           A-R-------SQ------------
HCV-J           A-R-------SQ--------------------F----------E---LL-S-----Q---
JH-1            A-RQ------SQ--------------------F-----N--D-E---LL-------H---
BK              --PQ-T----SE--------------------F-V---R----E---LL-------Q---
```

FIG. 3A

```
HCV-1    550   FGCTWMNSTGFTKVCGAPPCVIGGAGNNTLHCPTDCFRKHPDATYSRCGSGPWITPRCLV
HCT27          --------S---------------V-----Q-----------------AA----------
HCVE1          -----V--S---------------------Y----------E------------------
H77            ------------------------V-----L----------E----------------M-
H90            ------------------------V-----R----------E----------------M-
Th             ------------------------V-----------------------------------
HC-J1
HC-J4
HCV-J          -------------T--G---N---V-----V----------E---TK------L----M-
JH-1           -------------T--G---N---V-----T----------E---TK------L------
BK             -------------T--G---N---V-----T----------E---TK------L----M-

HCV-1    610   DYPYRLWHYPCTINYTIFKIRMYVGGVEHRLEAACNWTRGERCDLEDRDRSELSPLLLTT
HCT27          H-----------V----VQ--------D----V------------D--------RL--S-
HCVE1          G-----------V---L--V-----------QV----------N-D------------S-
H77            -------------------V--------------------------------------S-
H90            H------------------V------I-------------------------------S-
Th             N------------------V------------------
HC-J1
HC-J4
HCV-J          ------------V-F-V--V-----------N--------------------------S-
JH-1           ------------V-F----V---------
BK             ------------V-F----V-----------N------------------P-------S-
```

FIG. 3B

```
HCV-1    670   TQWQVLPCSFTTLPALSTGLIHIHQNIVDVQYLYGVGSSIASWAIKWEYVVLLFLLLADA
HCT27          -----------------T----------------------V---------I-------N-
HCVE1          -----------------T----------------------V---------I---------
H77            ------------------------------------------------------------
H90            --------------------------------------------T---------------
Th
HC-J1
HC-J4
HCV-J          -E--I--------------------R----------I--AVV-F-------IL-------
JH-1
BK             -E----------------------------------I--AVV-F--------L-------

HCV-1    730   RVCSCLWMMLLISQAEAALENLVILNAASLAGTHGLVSFLVFFCFAWYLKGKWVPGAVYT
HCT27          -I---------------------L--------A-AVA--------------R-----A-A
HCVE1          -------
H77            -------------------------------------------------
H90            --------------------------------A----------------
Th
HC-J1
HC-J4
HCV-J
HCV-J          ---A--------A----T-----V-----V--A---L-------A---I--RL----A-A
JH-1
BK             ---A--------A----------V--S--V--A--IL-------A---I--RL----T-A

HCV-1    790   FYGMWPLLLLLLALPQRAYALDTEVAASCGGVVLVGLMALTLSPYYKRYISWCLWWLQYF
HCT27          ------------------------M
Th
HC-J1
HC-J4
HCV-J
HCV-J          L--V-----------P----M-R-M------A-F---VL--------VFLARLI------
JH-1
BK             L--V-----------P----M-R-M------A-F---VL--------VFLARLI------
```

```
                     M
HCV J1.1   384   HTRVTGGVQGHVTSTLTSLFRPGASQKIQLVNTNGSWHINRTALNCNDSLQTGFLAALFY
HCV J1.2         N-H--------GAFG-----Q-----------------------------K---------
                   R   A

                                   VG            R*
HCV J1.1   444   THKFNASGCPERMASCRSIDKFDQGWGPITYAQPDNSDQRPYCWHYAPRQCGIVPASQVC
HCV J1.2         --R--------------------------------------------T------------

                                   F V
HCV J1.1   504   GPVYCFTPSPVVVGTTDRSGAPTYNWGDNETDVLLLNNTRPPHGNWFGCTWMNSTGFTKT
HCV J1.2         ------------------------------------------------------------

                                           R
                           A     I         E                        R
HCV J1.1   564   CGGPPCNIGGVGNNTLTCPTDCFRKHPDATYTKCGSGPWLTPRCLVDYPYRLWHYPCTVN
HCV J1.2         ------------------------------------------------------------

                       K   E
HCV J1.1   624   FTIFKVRMYVGGVEHRLDAACNWTRGER   651
HCV J1.2         ----------------------------
```

FIG. 8A

```
                    E2 HV
            |--------------------------|
HCT27  384  TTYTTGGNAARTTQALTSFFSPGAKQDIQLINTNGSWHINRTALNCNGSLDTGWVAGLFY
HCVE1       E------ST-----G-V-L--R-------------------------E------------

HCT27  444  YHKFNSSGCPERMASCRPLADFQQGWGPISYANGSGPEHRPYCWHYPPKPCGIVPAQNVC
HCVE1       ----------------------D-----------T----------------------T--

HCT27  504  GPVYCFTPSPVVVGTTNKLGAPTYNWGSNETDVFVLNNTRPPLGNWFGCTWMNSSGFTKV
HCVE1       ---------------------------C-D---------------------V--------

HCT27  564  CGAPPCVIGGVGNNTLQCPTDCFRKHPDATYSRCAAGPWITPRCLVHYPYRLWHYPCTVN
HCVE1       ----------A-----Y----------E------GS----------G-------------

HCT27  624  YTIVQIRMYVGGVDHRLEVACNWTRGERCDLDDRDRSELRLLLLSTTQWQVLPCSFTTLP
HCVE1       --LFKV-------E---Q-----------N---------SP-------------------

HCT27  684  ALTTGLIHLHQNIVDVQYLYGVGSSIVSWAIKWEYVILLFLLLANARICSCLW
HCVE1       --------------------------------------------D--V-----
```

FIG. 8B

```
Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175
```

FIG. 9A

| | | | | | | | | | | | | | | | |
|---|---|---|---|---|---|---|---|---|---|---|---|---|---|---|---|
| Phe | Leu | Leu | Ala | Leu | Leu | Ser | Cys | Leu | Thr | Val | Pro | Ala | Ser | Ala | Tyr |
| | | | 180 | | | | | 185 | | | | | 190 | | |
| Gln | Val | Arg | Asn | Ser | Thr | Gly | Leu | Tyr | His | Val | Thr | Asn | Asp | Cys | Pro |
| | | 195 | | | | | 200 | | | | | 205 | | | |
| Asn | Ser | Ser | Ile | Val | Tyr | Glu | Ala | Ala | Asp | Ala | Ile | Leu | His | Thr | Pro |
| | 210 | | | | | 215 | | | | | 220 | | | | |
| Gly | Cys | Val | Pro | Cys | Val | Arg | Glu | Gly | Asn | Ala | Ser | Arg | Cys | Trp | Val |
| 225 | | | | | 230 | | | | | 235 | | | | | 240 |
| Ala | Met | Thr | Pro | Thr | Val | Ala | Thr | Arg | Asp | Gly | Lys | Leu | Pro | Ala | Thr |
| | | | | 245 | | | | | 250 | | | | | 255 | |
| Gln | Leu | Arg | Arg | His | Ile | Asp | Leu | Leu | Val | Gly | Ser | Ala | Thr | Leu | Cys |
| | | | 260 | | | | | 265 | | | | | 270 | | |
| Ser | Ala | Leu | Tyr | Val | Gly | Asp | Leu | Cys | Gly | Ser | Val | Phe | Leu | Val | Gly |
| | | 275 | | | | | 280 | | | | | 285 | | | |
| Gln | Leu | Phe | Thr | Phe | Ser | Pro | Arg | Arg | His | Trp | Thr | Thr | Gln | Gly | Cys |
| | 290 | | | | | 295 | | | | | 300 | | | | |
| Asn | Cys | Ser | Ile | Tyr | Pro | Gly | His | Ile | Thr | Gly | His | Arg | Met | Ala | Trp |
| 305 | | | | | 310 | | | | | 315 | | | | | 320 |
| Asp | Met | Met | Met | Asn | Trp | Ser | Pro | Thr | Thr | Ala | Leu | Val | Met | Ala | Gln |
| | | | | 325 | | | | | 330 | | | | | 335 | |
| Leu | Leu | Arg | Ile | Pro | Gln | Ala | Ile | Leu | Asp | Met | Ile | Ala | Gly | Ala | His |
| | | | 340 | | | | | 345 | | | | | 350 | | |

FIG. 9B

Trp Gly Val Leu Ala Gly Ile Ala Tyr Phe Ser Met Val Gly Asn Trp
355 360 365

Ala Lys Val Leu Val Val Leu Leu Leu Phe Ala Gly Val Asp Ala Glu
370 375 380

Thr His Val Thr Gly Gly Ser Ala Gly His Thr Val Ser Gly Phe Val
385 390 395 400

Ser Leu Leu Ala Pro Gly Ala Lys Gln Asn Val Gln Leu Ile Asn Thr
405 410 415

Asn Gly Ser Trp His Leu Asn Ser Thr Ala Leu Asn Cys Asn Asp Ser
420 425 430

Leu Asn Thr Gly Trp Leu Ala Gly Leu Phe Tyr His His Lys Phe Asn
435 440 445

Ser Ser Gly Cys Pro Glu Arg Leu Ala Ser Cys Arg Pro Leu Thr Asp
450 455 460

Phe Asp Gln Gly Trp Gly Pro Ile Ser Tyr Ala Asn Gly Ser Gly Pro
465 470 475 480

Asp Gln Arg Pro Tyr Cys Trp His Tyr Pro Pro Lys Pro Cys Gly Ile
485 490 495

Val Pro Ala Lys Ser Val Cys Gly Pro Val Tyr Cys Phe Thr Pro Ser
500 505 510

Pro Val Val Val Gly Thr Thr Asp Arg Ser Gly Ala Pro Thr Tyr Ser
515 520 525

FIG. 9C

```
Trp Gly Glu Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Ala Gly Asn
                565                 570                 575

Asn Thr Leu His Cys Pro Thr Asp Cys Phe Arg Lys His Pro Asp Ala
            580                 585                 590

Thr Tyr Ser Arg Cys Gly Ser Gly Pro Trp Ile Thr Pro Arg Cys Leu
        595                 600                 605

Val Asp Tyr Pro Tyr Arg Leu Trp His Tyr Pro Cys Thr Ile Asn Tyr
    610                 615                 620

Thr Ile Phe Lys Ile Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Thr Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700
```

FIG. 9D

```
Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Lys Trp Val Pro
    770                 775                 780

Gly Ala Val Tyr Thr Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Leu Trp Trp Leu Gln Tyr
        835                 840                 845

Phe Leu Thr Arg Val Glu Ala Gln Leu His Val Trp Ile Pro Pro Leu
    850                 855                 860

Asn Val Arg Gly Gly Arg Asp Ala Val Ile Leu Leu Met Cys Ala Val
865                 870                 875                 880
```

FIG. 9E

```
His Pro Thr Leu Val Phe Asp Ile Thr Lys Leu Leu Leu Ala Val Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Phe Cys Ala Leu Ala Arg Lys Met
        915                 920                 925

Ile Gly Gly His Tyr Val Gln Met Val Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Gln Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Arg
        995                1000                1005

Glu Ile Leu Leu Gly Pro Ala Asp Gly Met Val Ser Lys Gly Trp Arg
   1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
                1045                1050                1055
```

FIG. 9F

```
Gly Glu Val Gln Ile Val Ser Thr Ala Ala Gln Thr Phe Leu Ala Thr
            1060                1065                1070

Cys Ile Asn Gly Val Cys Trp Thr Val Tyr His Gly Ala Gly Thr Arg
        1075                1080                1085

Thr Ile Ala Ser Pro Lys Gly Pro Val Ile Gln Met Tyr Thr Asn Val
    1090                1095                1100

Asp Gln Asp Leu Val Gly Trp Pro Ala Pro Gln Gly Ser Arg Ser Leu
1105                1110                1115                1120

Thr Pro Cys Thr Cys Gly Ser Ser Asp Leu Tyr Leu Val Thr Arg His
                1125                1130                1135

Ala Asp Val Ile Pro Val Arg Arg Arg Gly Asp Ser Arg Gly Ser Leu
            1140                1145                1150

Leu Ser Pro Arg Pro Ile Ser Tyr Leu Lys Gly Ser Ser Gly Gly Pro
        1155                1160                1165

Leu Leu Cys Pro Ala Gly His Ala Val Gly Ile Phe Arg Ala Ala Val
    1170                1175                1180

Cys Thr Arg Gly Val Ala Lys Ala Val Asp Phe Ile Pro Val Glu Asn
1185                1190                1195                1200

Leu Glu Thr Thr Met Arg Ser Pro Val Phe Thr Asp Asn Ser Ser Pro
                1205                1210                1215

Pro Val Val Pro Gln Ser Phe Gln Val Ala His Leu His Ala Pro Thr
            1220                1225                1230
```

FIG. 9G

```
Gly Ser Gly Lys Ser Thr Lys Val Pro Ala Ala Tyr Ala Ala Gln Gly
        1235                1240                1245

Tyr Lys Val Leu Val Leu Asn Pro Ser Val Ala Ala Thr Leu Gly Phe
    1250                1255                1260

Gly Ala Tyr Met Ser Lys Ala His Gly Ile Asp Pro Asn Ile Arg Thr
1265                1270                1275                1280

Gly Val Arg Thr Ile Thr Thr Gly Ser Pro Ile Thr Tyr Ser Thr Tyr
                1285                1290                1295

Gly Lys Phe Leu Ala Asp Gly Gly Cys Ser Gly Gly Ala Tyr Asp Ile
            1300                1305                1310

Ile Ile Cys Asp Glu Cys His Ser Thr Asp Ala Thr Ser Ile Leu Gly
        1315                1320                1325

Ile Gly Thr Val Leu Asp Gln Ala Glu Thr Ala Gly Ala Arg Leu Val
    1330                1335                1340

Val Leu Ala Thr Ala Thr Pro Pro Gly Ser Val Thr Val Pro His Pro
1345                1350                1355                1360

Asn Ile Glu Glu Val Ala Leu Ser Thr Thr Gly Glu Ile Pro Phe Tyr
                1365                1370                1375

Gly Lys Ala Ile Pro Leu Glu Val Ile Lys Gly Gly Arg His Leu Ile
            1380                1385                1390

Phe Cys His Ser Lys Lys Lys Cys Asp Glu Leu Ala Ala Lys Leu Val
        1395                1400                1405
```

FIG. 9H

Ala Leu Gly Ile Asn Ala Val Ala Tyr Tyr Arg Gly Leu Asp Val Ser
1410 1415 1420

Val Ile Pro Thr Ser Gly Asp Val Val Val Val Ala Thr Asp Ala Leu
1425 1430 1435 1440

Met Thr Gly Tyr Thr Gly Asp Phe Asp Ser Val Ile Asp Cys Asn Thr
1445 1450 1455

Cys Val Thr Gln Thr Val Asp Phe Ser Leu Asp Pro Thr Phe Thr Ile
1460 1465 1470

Glu Thr Ile Thr Leu Pro Gln Asp Ala Val Ser Arg Thr Gln Arg Arg
1475 1480 1485

Gly Arg Thr Gly Arg Gly Lys Pro Gly Ile Tyr Arg Phe Val Ala Pro
1490 1495 1500

Gly Glu Arg Pro Ser Gly Met Phe Asp Ser Ser Val Leu Cys Glu Cys
1505 1510 1515 1520

Tyr Asp Ala Gly Cys Ala Trp Tyr Glu Leu Thr Pro Ala Glu Thr Thr
1525 1530 1535

Val Arg Leu Arg Ala Tyr Met Asn Thr Pro Gly Leu Pro Val Cys Gln
1540 1545 1550

Asp His Leu Glu Phe Trp Glu Gly Val Phe Thr Gly Leu Thr His Ile
1555 1560 1565

Asp Ala His Phe Leu Ser Gln Thr Lys Gln Ser Gly Glu Asn Leu Pro
1570 1575 1580

FIG. 9I

```
Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
                1605                1610                1615

Thr Leu His Gly Pro Thr Pro Leu Leu Tyr Arg Leu Gly Ala Val Gln
            1620                1625                1630

Asn Glu Ile Thr Leu Thr His Pro Val Thr Lys Tyr Ile Met Thr Cys
        1635                1640                1645

Met Ser Ala Asp Leu Glu Val Val Thr Ser Thr Trp Val Leu Val Gly
    1650                1655                1660

Gly Val Leu Ala Ala Leu Ala Ala Tyr Cys Leu Ser Thr Gly Cys Val
1665                1670                1675                1680

Val Ile Val Gly Arg Val Val Leu Ser Gly Lys Pro Ala Ile Ile Pro
                1685                1690                1695

Asp Arg Glu Val Leu Tyr Arg Glu Phe Asp Glu Met Glu Glu Cys Ser
            1700                1705                1710

Gln His Leu Pro Tyr Ile Glu Gln Gly Met Met Leu Ala Glu Gln Phe
        1715                1720                1725

Lys Gln Lys Ala Leu Gly Leu Leu Gln Thr Ala Ser Arg Gln Ala Glu
    1730                1735                1740

Val Ile Ala Pro Ala Val Gln Thr Asn Trp Gln Lys Leu Glu Thr Phe
1745                1750                1755                1760
```

FIG. 9J

```
Trp Ala Lys His Met Trp Asn Phe Ile Ser Gly Ile Gln Tyr Leu Ala
                1765                1770                1775

Gly Leu Ser Thr Leu Pro Gly Asn Pro Ala Ile Ala Ser Leu Met Ala
            1780                1785                1790

Phe Thr Ala Ala Val Thr Ser Pro Leu Thr Thr Ser Gln Thr Leu Leu
        1795                1800                1805

Phe Asn Ile Leu Gly Gly Trp Val Ala Ala Gln Leu Ala Ala Pro Gly
    1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Ile Asp Ile Leu Ala Gly Tyr Gly
                1845                1850                1855

Ala Gly Val Ala Gly Ala Leu Val Ala Phe Lys Ile Met Ser Gly Glu
            1860                1865                1870

Val Pro Ser Thr Glu Asp Leu Val Asn Leu Leu Pro Ala Ile Leu Ser
        1875                1880                1885

Pro Gly Ala Leu Val Val Gly Val Val Cys Ala Ala Ile Leu Arg Arg
    1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                1925                1930                1935
```

FIG. 9K

```
Glu Ser Asp Ala Ala Ala Arg Val Thr Ala Ile Leu Ser Ser Leu Thr
            1940                1945                1950

Val Thr Gln Leu Leu Arg Arg Leu His Gln Trp Ile Ser Ser Glu Cys
        1955                1960                1965

Thr Thr Pro Cys Ser Gly Ser Trp Leu Arg Asp Ile Trp Asp Trp Ile
    1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Lys
                2005                2010                2015

Gly Val Trp Arg Val Asp Gly Ile Met His Thr Arg Cys His Cys Gly
            2020                2025                2030

Ala Glu Ile Thr Gly His Val Lys Asn Gly Thr Met Arg Ile Val Gly
        2035                2040                2045

Pro Arg Thr Cys Arg Asn Met Trp Ser Gly Thr Phe Pro Ile Asn Ala
    2050                2055                2060

Tyr Thr Thr Gly Pro Cys Thr Pro Leu Pro Ala Pro Asn Tyr Thr Phe
2065                2070                2075                2080

Ala Leu Trp Arg Val Ser Ala Glu Glu Tyr Val Glu Ile Arg Gln Val
                2085                2090                2095

Gly Asp Phe His Tyr Val Thr Gly Met Thr Thr Asp Asn Leu Lys Cys
            2100                2105                2110
```

FIG. 9L

```
Pro Cys Gln Val Pro Ser Pro Glu Phe Phe Thr Glu Leu Asp Gly Val
        2115                2120                2125

Arg Leu His Arg Phe Ala Pro Pro Cys Lys Pro Leu Leu Arg Glu Glu
    2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
                2165                2170                2175

Asp Pro Ser His Ile Thr Ala Glu Ala Ala Gly Arg Arg Leu Ala Arg
            2180                2185                2190

Gly Ser Pro Pro Ser Val Ala Ser Ser Ser Ala Ser Gln Leu Ser Ala
        2195                2200                2205

Pro Ser Leu Lys Ala Thr Cys Thr Ala Asn His Asp Ser Pro Asp Ala
    2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
                2245                2250                2255

Asp Pro Leu Val Ala Glu Glu Asp Glu Arg Glu Ile Ser Val Pro Ala
            2260                2265                2270

Glu Ile Leu Arg Lys Ser Arg Arg Phe Ala Gln Ala Leu Pro Val Trp
        2275                2280                2285
```

FIG. 9M

```
Ala Arg Pro Asp Tyr Asn Pro Pro Leu Val Glu Thr Trp Lys Lys Pro
    2290                2295                2300

Asp Tyr Glu Pro Pro Val Val His Gly Cys Pro Leu Pro Pro Pro Lys
2305                2310                2315                2320

Ser Pro Pro Val Pro Pro Pro Arg Lys Lys Arg Thr Val Val Leu Thr
                2325                2330                2335

Glu Ser Thr Leu Ser Thr Ala Leu Ala Glu Leu Ala Thr Arg Ser Phe
            2340                2345                2350

Gly Ser Ser Ser Thr Ser Gly Ile Thr Gly Asp Asn Thr Thr Thr Ser
        2355                2360                2365

Ser Glu Pro Ala Pro Ser Gly Cys Pro Pro Asp Ser Asp Ala Glu Ser
    2370                2375                2380

Tyr Ser Ser Met Pro Pro Leu Glu Gly Glu Pro Gly Asp Pro Asp Leu
2385                2390                2395                2400

Ser Asp Gly Ser Trp Ser Thr Val Ser Ser Glu Ala Asn Ala Glu Asp
                2405                2410                2415

Val Val Cys Cys Ser Met Ser Tyr Ser Trp Thr Gly Ala Leu Val Thr
            2420                2425                2430

Pro Cys Ala Ala Glu Glu Gln Lys Leu Pro Ile Asn Ala Leu Ser Asn
        2435                2440                2445

Ser Leu Leu Arg His His Asn Leu Val Tyr Ser Thr Thr Ser Arg Ser
    2450                2455                2460
```

FIG. 9N

```
Ala Cys Gln Arg Gln Lys Lys Val Thr Phe Asp Arg Leu Gln Val Leu
2465                2470                2475                2480

Asp Ser His Tyr Gln Asp Val Leu Lys Glu Val Lys Ala Ala Ala Ser
                2485                2490                2495

Lys Val Lys Ala Asn Leu Leu Ser Val Glu Glu Ala Cys Ser Leu Thr
            2500                2505                2510

Pro Pro His Ser Ala Lys Ser Lys Phe Gly Tyr Gly Ala Lys Asp Val
        2515                2520                2525

Arg Cys His Ala Arg Lys Ala Val Thr His Ile Asn Ser Val Trp Lys
    2530                2535                2540

Asp Leu Leu Glu Asp Asn Val Thr Pro Ile Asp Thr Thr Ile Met Ala
2545                2550                2555                2560

Lys Asn Glu Val Phe Cys Val Gln Pro Glu Lys Gly Gly Arg Lys Pro
                2565                2570                2575

Ala Arg Leu Ile Val Phe Pro Asp Leu Gly Val Arg Val Cys Glu Lys
            2580                2585                2590

Met Ala Leu Tyr Asp Val Val Thr Lys Leu Pro Leu Ala Val Met Gly
        2595                2600                2605

Ser Ser Tyr Gly Phe Gln Tyr Ser Pro Gly Gln Arg Val Glu Phe Leu
    2610                2615                2620

Val Gln Ala Trp Lys Ser Lys Lys Thr Pro Met Gly Phe Ser Tyr Asp
2625                2630                2635                2640
```

FIG. 9O

```
Thr Arg Cys Phe Asp Ser Thr Val Thr Glu Ser Asp Ile Arg Thr Glu
                2645                2650                2655

Glu Ala Ile Tyr Gln Cys Cys Asp Leu Asp Pro Gln Ala Arg Val Ala
            2660                2665                2670

Ile Lys Ser Leu Thr Glu Arg Leu Tyr Val Gly Gly Pro Leu Thr Asn
        2675                2680                2685

Ser Arg Gly Glu Asn Cys Gly Tyr Arg Arg Cys Arg Ala Ser Gly Val
    2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
                2725                2730                2735

Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
        2755                2760                2765

Pro Pro Gly Asp Pro Pro Gln Pro Glu Tyr Asp Leu Glu Leu Ile Thr
    2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
                2805                2810                2815
```

FIG. 9P

```
Trp Glu Thr Ala Arg His Thr Pro Val Asn Ser Trp Leu Gly Asn Ile
            2820                2825                2830

Ile Met Phe Ala Pro Thr Leu Trp Ala Arg Met Ile Leu Met Thr His
        2835                2840                2845

Phe Phe Ser Val Leu Ile Ala Arg Asp Gln Leu Glu Gln Ala Leu Asp
    2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
                2885                2890                2895

Tyr Ser Pro Gly Glu Ile Asn Arg Val Ala Ala Cys Leu Arg Lys Leu
            2900                2905                2910

Gly Val Pro Pro Leu Arg Ala Trp Arg His Arg Ala Arg Ser Val Arg
        2915                2920                2925

Ala Arg Leu Leu Ala Arg Gly Gly Arg Ala Ala Ile Cys Gly Lys Tyr
    2930                2935                2940

Leu Phe Asn Trp Ala Val Arg Thr Lys Leu Lys Leu Thr Pro Ile Ala
2945                2950                2955                2960

Ala Ala Gly Gln Leu Asp Leu Ser Gly Trp Phe Thr Ala Gly Tyr Ser
                2965                2970                2975

Gly Gly Asp Ile Tyr His Ser Val Ser His Ala Arg Pro Arg Trp Ile
            2980                2985                2990
```

FIG. 9Q

```
Trp Phe Cys Leu Leu Leu Leu Ala Ala Gly Val Gly Ile Tyr Leu Leu
        2995                3000                3005

Pro Asn Arg
    3010
```

FIG. 9R

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GGTGCTCACT GGGGAGTCCT 20

( 2 ) INFORMATION FOR SEQ ID NO:2:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

CATTGCAGTT CAGGGCCGTG CTA 23

( 2 ) INFORMATION FOR SEQ ID NO:3:

( i ) SEQUENCE CHARACTERISTICS:
( A ) LENGTH: 20 base pairs

-continued ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

TCCATGGTGG GGAACTGGGC 20

( 2 ) INFORMATION FOR SEQ ID NO:4:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

TGCCAACTGC CATTGGTGTT 20

( 2 ) INFORMATION FOR SEQ ID NO:5:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

TAACGGGCTG AGCTCGGA 18

( 2 ) INFORMATION FOR SEQ ID NO:6:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

CAATTGGTTC GGTTGTACC 19

( 2 ) INFORMATION FOR SEQ ID NO:7:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

CGTCCAGTTC GGAGGCAGCT TC 22

( 2 ) INFORMATION FOR SEQ ID NO:8:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

CAGGGCAGTA TCTGCCACTC 20

( 2 ) INFORMATION FOR SEQ ID NO:9:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

TGAGACGGAC GTGCTGCTCC T 21

( 2 ) INFORMATION FOR SEQ ID NO:10:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

TTTGATGTAC CAGGCGGCGC A 21

( 2 ) INFORMATION FOR SEQ ID NO:11:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

GGATCCGCTA GCCATACCCG CGTGACGGGG GGGGTGCAA 39

( 2 ) INFORMATION FOR SEQ ID NO:12:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:12:

GGATCCTCTA GATTACTCTT CTGACCTATC CCTGTCCTCC AAGTC 45

( 2 ) INFORMATION FOR SEQ ID NO:13:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:13:

CAACTGGTTC GGCTGTACA 19

( 2 ) INFORMATION FOR SEQ ID NO:14:

( i ) SEQUENCE CHARACTERISTICS:
( A ) LENGTH: 480 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:14:

```
Lys Val Leu Val Val Leu Leu Leu Phe Ala Gly Val Asp Ala Glu Thr
1               5                   10                  15

His Val Thr Gly Gly Ser Ala Gly His Thr Val Ser Gly Phe Val Ser
            20                  25                  30

Leu Leu Ala Pro Gly Ala Lys Gln Asn Val Gln Leu Ile Asn Thr Asn
        35                  40                  45

Gly Ser Trp His Leu Asn Ser Thr Ala Leu Asn Cys Asn Asp Ser Leu
    50                  55                  60

Asn Thr Gly Trp Leu Ala Gly Leu Phe Tyr His His Lys Phe Asn Ser
65                  70                  75                  80

Ser Gly Cys Pro Glu Arg Leu Ala Ser Cys Arg Pro Leu Thr Asp Phe
                85                  90                  95

Asp Gln Gly Trp Gly Pro Ile Ser Tyr Ala Asn Gly Ser Gly Pro Asp
            100                 105                 110

Gln Arg Pro Tyr Cys Trp His Tyr Pro Pro Lys Pro Cys Gly Ile Val
        115                 120                 125

Pro Ala Lys Ser Val Cys Gly Pro Val Tyr Cys Phe Thr Pro Ser Pro
    130                 135                 140

Val Val Val Gly Thr Thr Asp Arg Ser Gly Ala Pro Thr Tyr Ser Trp
145                 150                 155                 160

Gly Glu Asn Asp Thr Asp Val Phe Val Leu Asn Asn Thr Arg Pro Pro
                165                 170                 175

Leu Gly Asn Trp Phe Gly Cys Thr Trp Met Asn Ser Thr Gly Phe Thr
            180                 185                 190

Lys Val Cys Gly Ala Pro Pro Cys Val Ile Gly Gly Ala Gly Asn Asn
        195                 200                 205

Thr Leu His Cys Pro Thr Asp Cys Phe Arg Lys His Pro Asp Ala Thr
    210                 215                 220

Tyr Ser Arg Cys Gly Ser Gly Pro Trp Ile Thr Pro Arg Cys Leu Val
225                 230                 235                 240

Asp Tyr Pro Tyr Arg Leu Trp His Tyr Pro Cys Thr Ile Asn Tyr Thr
                245                 250                 255

Ile Phe Lys Ile Arg Met Tyr Val Gly Gly Val Glu His Arg Leu Glu
            260                 265                 270

Ala Ala Cys Asn Trp Thr Arg Gly Glu Arg Cys Asp Leu Glu Asp Arg
        275                 280                 285

Asp Arg Ser Glu Leu Ser Pro Leu Leu Leu Thr Thr Thr Gln Trp Gln
    290                 295                 300

Val Leu Pro Cys Ser Phe Thr Thr Leu Pro Ala Leu Ser Thr Gly Leu
305                 310                 315                 320

Ile His Leu His Gln Asn Ile Val Asp Val Gln Tyr Leu Tyr Gly Val
                325                 330                 335

Gly Ser Ser Ile Ala Ser Trp Ala Ile Lys Trp Glu Tyr Val Val Leu
            340                 345                 350

Leu Phe Leu Leu Leu Ala Asp Ala Arg Val Cys Ser Cys Leu Trp Met
```

-continued

```
        355                 360                 365

Met Leu Leu Ile Ser Gln Ala Glu Ala Ala Leu Glu Asn Leu Val Ile
    370                 375                 380

Leu Asn Ala Ala Ser Leu Ala Gly Thr His Gly Leu Val Ser Phe Leu
385                 390                 395                 400

Val Phe Phe Cys Phe Ala Trp Tyr Leu Lys Gly Lys Trp Val Pro Gly
                405                 410                 415

Ala Val Tyr Thr Phe Tyr Gly Met Trp Pro Leu Leu Leu Leu Leu Leu
            420                 425                 430

Ala Leu Pro Gln Arg Ala Tyr Ala Leu Asp Thr Glu Val Ala Ala Ser
        435                 440                 445

Cys Gly Gly Val Val Leu Val Gly Leu Met Ala Leu Thr Leu Ser Pro
    450                 455                 460

Tyr Tyr Lys Arg Tyr Ile Ser Trp Cys Leu Trp Trp Leu Gln Tyr Phe
465                 470                 475                 480
```

( 2 ) INFORMATION FOR SEQ ID NO:15:

( i ) SEQUENCE CHARACTERISTICS:
( A ) LENGTH: 278 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:15:

```
Lys Val Leu Val Val Leu Leu Leu Phe Ala Gly Val Asp Ala Glu Thr
1               5                   10                  15

Thr Val Thr Gly Gly Ser Ala Ala His Gly Ala Leu Gly Ile Ala Ser
            20                  25                  30

Leu Phe Asn Gln Gly Ala Arg Gln Asn Ile Gln Leu Ile Asn Thr Asn
        35                  40                  45

Gly Ser Trp His Ile Asn Ser Thr Ala Leu Asn Cys Asn Asp Ser Leu
    50                  55                  60

Asn Thr Gly Trp Ile Ala Gly Leu Phe Tyr Tyr His Lys Phe Asn Ser
65                  70                  75                  80

Ser Gly Cys Pro Glu Arg Leu Ala Ser Cys Arg Pro Leu Thr Asp Phe
                85                  90                  95

Asp Gln Gly Trp Gly Pro Ile Ser Tyr Ala Asn Gly Ser Gly Pro Asp
            100                 105                 110

Gln Arg Pro Tyr Cys Trp His Tyr Pro Pro Lys Pro Cys Gly Ile Val
        115                 120                 125

Pro Ala Lys Ser Val Cys Gly Pro Val Tyr Cys Phe Thr Pro Ser Pro
    130                 135                 140

Val Val Val Gly Thr Thr Asp Arg Ser Gly Ala Pro Thr Tyr Asn Trp
145                 150                 155                 160

Gly Ala Asn Asp Thr Asp Val Phe Val Leu Asn Asn Thr Arg Pro Pro
                165                 170                 175

Leu Gly Asn Trp Phe Gly Cys Thr Trp Met Asn Ser Thr Gly Phe Thr
            180                 185                 190

Lys Val Cys Gly Ala Pro Pro Cys Val Ile Gly Gly Val Gly Asn Asn
        195                 200                 205

Thr Leu His Cys Pro Thr Asp Cys Phe Arg Lys His Pro Asp Ala Thr
    210                 215                 220

Tyr Ser Arg Cys Gly Ser Gly Pro Trp Ile Thr Pro Arg Cys Leu Val
225                 230                 235                 240
```

-continued

Asn Tyr Pro Tyr Arg Leu Trp His Tyr Pro Cys Thr Ile Asn Tyr Thr
245 250 255

Ile Phe Lys Val Arg Met Tyr Val Gly Gly Val Glu His Arg Leu Glu
260 265 270

Ala Ala Cys Asn Trp Thr
275

( 2 ) INFORMATION FOR SEQ ID NO:16:

( i ) SEQUENCE CHARACTERISTICS:
( A ) LENGTH: 269 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:16:

Lys Val Leu Ile Val Met Leu Leu Phe Ala Gly Val Asp Gly His Thr
1 5 10 15

Arg Val Thr Gly Gly Val Gln Gly His Val Thr Ser Thr Leu Thr Ser
20 25 30

Leu Phe Arg Pro Gly Ala Ser Gln Lys Ile Gln Leu Val Asn Thr Asn
35 40 45

Gly Ser Trp His Ile Asn Arg Thr Ala Leu Asn Cys Asn Asp Ser Leu
50 55 60

Gln Thr Gly Phe Leu Ala Ala Leu Phe Tyr Thr His Lys Phe Asn Ala
65 70 75 80

Ser Gly Cys Pro Glu Arg Met Ala Ser Cys Arg Ser Ile Asp Lys Phe
85 90 95

Asp Gln Gly Trp Gly Pro Ile Thr Tyr Ala Gln Pro Asp Asn Ser Asp
100 105 110

Gln Arg Pro Tyr Cys Trp His Tyr Ala Pro Arg Gln Cys Gly Ile Val
115 120 125

Pro Ala Ser Gln Val Cys Gly Pro Val Tyr Cys Phe Thr Pro Ser Pro
130 135 140

Val Val Val Gly Thr Thr Asp Arg Phe Gly Ala Pro Thr Tyr Asn Trp
145 150 155 160

Gly Asp Asn Glu Thr Asp Val Leu Leu Leu Asn Asn Thr Arg Pro Pro
165 170 175

His Gly Asn Trp Phe Gly Cys Thr Trp Met Asn Ser Thr Gly Phe Thr
180 185 190

Lys Thr Cys Gly Gly Pro Pro Cys Asn Ile Gly Gly Val Gly Asn Asn
195 200 205

Thr Leu Thr Cys Pro Thr Asp Cys Phe Arg Lys His Pro Glu Ala Thr
210 215 220

Tyr Thr Lys Cys Gly Ser Gly Pro Trp Leu Thr Pro Arg Cys Leu Val
225 230 235 240

Asp Tyr Pro Tyr Arg Leu Trp His Tyr Pro Cys Thr Val Asn Phe Thr
245 250 255

Ile Phe Lys Val Arg Met Tyr Val Gly Gly Val Glu His
260 265

( 2 ) INFORMATION FOR SEQ ID NO:17:

( i ) SEQUENCE CHARACTERISTICS:
( A ) LENGTH: 367 amino acids
( B ) TYPE: amino acid -continued ( C ) STRANDEDNESS: single
( D ) TOPOLOGY: linear ( i i ) MOLECULE TYPE: protein ( x i ) SEQUENCE DESCRIPTION: SEQ ID NO:17:

| | | | | | | | | | | | | | | | |
|---|---|---|---|---|---|---|---|---|---|---|---|---|---|---|---|
| Lys | Val | Leu | Leu | Val | Leu | Leu | Leu | Phe | Ala | Gly | Val | Asp | Ala | Glu | Thr |
| 1 | | | | 5 | | | | | 10 | | | | | 15 | |
| Tyr | Thr | Thr | Gly | Gly | Ser | Thr | Ala | Arg | Thr | Thr | Gln | Gly | Leu | Val | Ser |
| | | | 20 | | | | | 25 | | | | | 30 | | |
| Leu | Phe | Ser | Arg | Gly | Ala | Lys | Gln | Asp | Ile | Gln | Leu | Ile | Asn | Thr | Asn |
| | | 35 | | | | | 40 | | | | | 45 | | | |
| Gly | Ser | Trp | His | Ile | Asn | Arg | Thr | Ala | Leu | Asn | Cys | Asn | Glu | Ser | Leu |
| | 50 | | | | | 55 | | | | | 60 | | | | |
| Asp | Thr | Gly | Trp | Val | Ala | Gly | Leu | Phe | Tyr | Tyr | His | Lys | Phe | Asn | Ser |
| 65 | | | | | 70 | | | | | 75 | | | | | 80 |
| Ser | Gly | Cys | Pro | Glu | Arg | Met | Ala | Ser | Cys | Arg | Pro | Leu | Ala | Asp | Phe |
| | | | | 85 | | | | | 90 | | | | | 95 | |
| Asp | Gln | Gly | Trp | Gly | Pro | Ile | Ser | Tyr | Ala | Asn | Gly | Thr | Gly | Pro | Glu |
| | | | 100 | | | | | 105 | | | | | 110 | | |
| His | Arg | Pro | Tyr | Cys | Trp | His | Tyr | Pro | Pro | Lys | Pro | Cys | Gly | Ile | Val |
| | | 115 | | | | | 120 | | | | | 125 | | | |
| Pro | Ala | Gln | Thr | Val | Cys | Gly | Pro | Val | Tyr | Cys | Phe | Thr | Pro | Ser | Pro |
| | 130 | | | | | 135 | | | | | 140 | | | | |
| Val | Val | Val | Gly | Thr | Thr | Asn | Lys | Leu | Gly | Ala | Pro | Thr | Tyr | Asn | Trp |
| 145 | | | | | 150 | | | | | 155 | | | | | 160 |
| Gly | Cys | Asn | Asp | Thr | Asp | Val | Phe | Val | Leu | Asn | Asn | Thr | Arg | Pro | Pro |
| | | | | 165 | | | | | 170 | | | | | 175 | |
| Leu | Gly | Asn | Trp | Phe | Gly | Cys | Thr | Trp | Val | Asn | Ser | Ser | Gly | Phe | Thr |
| | | | 180 | | | | | 185 | | | | | 190 | | |
| Lys | Val | Cys | Gly | Ala | Pro | Pro | Cys | Val | Ile | Gly | Gly | Ala | Gly | Asn | Asn |
| | | 195 | | | | | 200 | | | | | 205 | | | |
| Thr | Leu | Tyr | Cys | Pro | Thr | Asp | Cys | Phe | Arg | Lys | His | Pro | Glu | Ala | Thr |
| | 210 | | | | | 215 | | | | | 220 | | | | |
| Tyr | Ser | Arg | Cys | Gly | Ser | Gly | Pro | Trp | Ile | Thr | Pro | Arg | Cys | Leu | Val |
| 225 | | | | | 230 | | | | | 235 | | | | | 240 |
| Gly | Tyr | Pro | Tyr | Arg | Leu | Trp | His | Tyr | Pro | Cys | Thr | Val | Asn | Tyr | Thr |
| | | | | 245 | | | | | 250 | | | | | 255 | |
| Leu | Phe | Lys | Val | Arg | Met | Tyr | Val | Gly | Gly | Val | Glu | His | Arg | Leu | Gln |
| | | | 260 | | | | | 265 | | | | | 270 | | |
| Val | Ala | Cys | Asn | Trp | Thr | Arg | Gly | Glu | Arg | Cys | Asn | Leu | Asp | Asp | Arg |
| | | 275 | | | | | 280 | | | | | 285 | | | |
| Asp | Arg | Ser | Glu | Leu | Ser | Pro | Leu | Leu | Leu | Ser | Thr | Thr | Gln | Trp | Gln |
| | 290 | | | | | 295 | | | | | 300 | | | | |
| Val | Leu | Pro | Cys | Ser | Phe | Thr | Thr | Leu | Pro | Ala | Leu | Thr | Thr | Gly | Leu |
| 305 | | | | | 310 | | | | | 315 | | | | | 320 |
| Ile | His | Leu | His | Gln | Asn | Ile | Val | Asp | Val | Gln | Tyr | Leu | Tyr | Gly | Val |
| | | | | 325 | | | | | 330 | | | | | 335 | |
| Gly | Ser | Ser | Ile | Val | Ser | Trp | Ala | Ile | Lys | Trp | Glu | Tyr | Val | Ile | Leu |
| | | | 340 | | | | | 345 | | | | | 350 | | |
| Leu | Phe | Leu | Leu | Leu | Ala | Asp | Ala | Arg | Val | Cys | Ser | Cys | Leu | Trp | |
| | | 355 | | | | | 360 | | | | | 365 | | | |

( 2 ) INFORMATION FOR SEQ ID NO:18:

( i ) SEQUENCE CHARACTERISTICS:

-continued ( A ) LENGTH: 480 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:18:

Lys Val Leu Ile Val Met Leu Leu Phe Ala Gly Val Asp Gly His Thr
1 5 10 15

His Val Thr Gly Gly Arg Val Ala Ser Ser Thr Gln Ser Leu Val Ser
20 25 30

Trp Leu Ser Gln Gly Pro Ser Gln Lys Ile Gln Leu Val Asn Thr Asn
35 40 45

Gly Ser Trp His Ile Asn Arg Thr Ala Leu Asn Cys Asn Asp Ser Leu
50 55 60

Gln Thr Gly Phe Ile Ala Ala Leu Phe Tyr Ala His Arg Phe Asn Ala
65 70 75 80

Ser Gly Cys Pro Glu Arg Met Ala Ser Cys Arg Pro Ile Asp Glu Phe
85 90 95

Ala Gln Gly Trp Gly Pro Ile Thr His Asp Met Pro Glu Ser Ser Asp
100 105 110

Gln Arg Pro Tyr Cys Trp His Tyr Ala Pro Arg Pro Cys Gly Ile Val
115 120 125

Pro Ala Ser Gln Val Cys Gly Pro Val Tyr Cys Phe Thr Pro Ser Pro
130 135 140

Val Val Val Gly Thr Thr Asp Arg Phe Gly Ala Pro Thr Tyr Ser Trp
145 150 155 160

Gly Glu Asn Glu Thr Asp Val Leu Leu Leu Ser Asn Thr Arg Pro Pro
165 170 175

Gln Gly Asn Trp Phe Gly Cys Thr Trp Met Asn Ser Thr Gly Phe Thr
180 185 190

Lys Thr Cys Gly Gly Pro Pro Cys Asn Ile Gly Gly Val Gly Asn Asn
195 200 205

Thr Leu Val Cys Pro Thr Asp Cys Phe Arg Lys His Pro Glu Ala Thr
210 215 220

Tyr Thr Lys Cys Gly Ser Gly Pro Trp Leu Thr Pro Arg Cys Met Val
225 230 235 240

Asp Tyr Pro Tyr Arg Leu Trp His Tyr Pro Cys Thr Val Asn Phe Thr
245 250 255

Val Phe Lys Val Arg Met Tyr Val Gly Gly Val Glu His Arg Leu Asn
260 265 270

Ala Ala Cys Asn Trp Thr Arg Gly Glu Arg Cys Asp Leu Glu Asp Arg
275 280 285

Asp Arg Ser Glu Leu Ser Pro Leu Leu Leu Ser Thr Thr Glu Trp Gln
290 295 300

Ile Leu Pro Cys Ser Phe Thr Thr Leu Pro Ala Leu Ser Thr Gly Leu
305 310 315 320

Ile His Leu His Arg Asn Ile Val Asp Val Gln Tyr Leu Tyr Gly Ile
325 330 335

Gly Ser Ala Val Val Ser Phe Ala Ile Lys Trp Glu Tyr Ile Leu Leu
340 345 350

Leu Phe Leu Leu Leu Ala Asp Ala Arg Val Cys Ala Cys Leu Trp Met
355 360 365

Met Leu Leu Ile Ala Gln Ala Glu Ala Thr Leu Glu Asn Leu Val Val
370 375 380

-continued

Leu Asn Ala Ala Ser Val Ala Gly Ala His Gly Leu Leu Ser Phe Leu
385 390 395 400

Val Phe Phe Cys Ala Ala Trp Tyr Ile Lys Gly Arg Leu Val Pro Gly
405 410 415

Ala Ala Tyr Ala Leu Tyr Gly Val Trp Pro Leu Leu Leu Leu Leu Leu
420 425 430

Ala Leu Pro Pro Arg Ala Tyr Ala Met Asp Arg Glu Met Ala Ala Ser
435 440 445

Cys Gly Gly Ala Val Phe Val Gly Leu Val Leu Leu Thr Leu Ser Pro
450 455 460

Tyr Tyr Lys Val Phe Leu Ala Arg Leu Ile Trp Trp Leu Gln Tyr Phe
465 470 475 480

( 2 ) INFORMATION FOR SEQ ID NO:19:

( i ) SEQUENCE CHARACTERISTICS:
( A ) LENGTH: 144 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:19:

Lys Val Leu Ile Val Ala Leu Leu Phe Ala Gly Val Asp Gly Glu Thr
1 5 10 15

Tyr Thr Ser Gly Gly Ala Ala Ser His Thr Thr Ser Thr Leu Ala Ser
20 25 30

Leu Phe Ser Pro Gly Ala Ser Gln Arg Ile Gln Leu Val Asn Thr Asn
35 40 45

Gly Ser Trp His Ile Asn Arg Thr Ala Leu Asn Cys Asn Asp Ser Leu
50 55 60

His Thr Gly Phe Leu Ala Ala Leu Phe Tyr Thr His Arg Phe Asn Ser
65 70 75 80

Ser Gly Cys Pro Glu Arg Met Ala Ser Cys Arg Pro Ile Asp Trp Phe
85 90 95

Ala Gln Gly Trp Gly Pro Ile Thr Tyr Thr Glu Pro Asp Ser Pro Asp
100 105 110

Gln Arg Pro Tyr Cys Trp His Tyr Ala Pro Arg Pro Cys Gly Ile Val
115 120 125

Pro Ala Ser Gln Val Cys Gly Pro Val Tyr Cys Phe Thr Pro Ser Pro
130 135 140

( 2 ) INFORMATION FOR SEQ ID NO:20:

( i ) SEQUENCE CHARACTERISTICS:
( A ) LENGTH: 144 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:20:

Lys Val Leu Val Val Leu Leu Leu Phe Ala Gly Val Asp Ala Glu Thr
1 5 10 15

Ile Val Ser Gly Gly Gln Ala Ala Arg Ala Met Ser Gly Leu Val Ser
20 25 30

Leu Phe Thr Pro Gly Ala Lys Gln Asn Ile Gln Leu Ile Asn Thr Asn
35 40 45

Gly Ser Trp His Ile Asn Ser Thr Ala Leu Asn Cys Asn Glu Ser Leu
50 55 60

Asn Thr Gly Trp Leu Ala Gly Leu Ile Tyr Gln His Lys Phe Asn Ser
65 70 75 80

Ser Gly Cys Pro Glu Arg Leu Ala Ser Cys Arg Arg Leu Thr Asp Phe
85 90 95

Asp Gln Gly Trp Gly Pro Ile Ser His Ala Asn Gly Ser Gly Pro Asp
100 105 110

Gln Arg Pro Tyr Cys Trp His Tyr Pro Pro Lys Pro Cys Gly Ile Val
115 120 125

Pro Ala Lys Ser Val Cys Gly Pro Val Tyr Cys Phe Thr Pro Ser Pro
130 135 140

( 2 ) INFORMATION FOR SEQ ID NO:21:

( i ) SEQUENCE CHARACTERISTICS:
( A ) LENGTH: 409 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:21:

Lys Val Leu Val Val Leu Leu Leu Phe Ala Gly Val Asp Ala Glu Thr
1 5 10 15

His Val Thr Gly Gly Ser Ala Gly Arg Thr Thr Ala Gly Leu Val Gly
20 25 30

Leu Leu Thr Pro Gly Ala Lys Gln Asn Ile Gln Leu Ile Asn Thr Asn
35 40 45

Gly Ser Trp His Ile Asn Ser Thr Ala Leu Asn Cys Asn Glu Ser Leu
50 55 60

Asn Thr Gly Trp Leu Ala Gly Leu Phe Tyr His His Lys Phe Asn Ser
65 70 75 80

Ser Gly Cys Pro Glu Arg Leu Ala Ser Cys Arg Arg Leu Thr Asp Phe
85 90 95

Ala Gln Gly Trp Gly Pro Ile Ser Tyr Ala Asn Gly Ser Gly Leu Asp
100 105 110

Glu Arg Pro Tyr Cys Trp His Tyr Pro Pro Arg Pro Cys Gly Ile Val
115 120 125

Pro Ala Lys Ser Val Cys Gly Pro Val Tyr Cys Phe Thr Pro Ser Pro
130 135 140

Val Val Val Gly Thr Thr Asp Arg Ser Gly Ala Pro Thr Tyr Ser Trp
145 150 155 160

Gly Ala Asn Asp Thr Asp Val Phe Val Leu Asn Asn Thr Arg Pro Pro
165 170 175

Leu Gly Asn Trp Phe Gly Cys Thr Trp Met Asn Ser Thr Gly Phe Thr
180 185 190

Lys Val Cys Gly Ala Pro Pro Cys Val Ile Gly Gly Val Gly Asn Asn
195 200 205

Thr Leu Leu Cys Pro Thr Asp Cys Phe Arg Lys His Pro Glu Ala Thr
210 215 220

Tyr Ser Arg Cys Gly Ser Gly Pro Trp Ile Thr Pro Arg Cys Met Val
225 230 235 240

Asp Tyr Pro Tyr Arg Leu Trp His Tyr Pro Cys Thr Ile Asn Tyr Thr
245 250 255

-continued

| | | | | | | | | | | | | | | | |
|---|---|---|---|---|---|---|---|---|---|---|---|---|---|---|---|
| Ile | Phe | Lys | Val | Arg | Met | Tyr | Val | Gly | Gly | Val | Glu | His | Arg | Leu | Glu |
| | | | 260 | | | | | 265 | | | | | 270 | | |
| Ala | Ala | Cys | Asn | Trp | Thr | Arg | Gly | Glu | Arg | Cys | Asp | Leu | Glu | Asp | Arg |
| | | 275 | | | | | 280 | | | | | 285 | | | |
| Asp | Arg | Ser | Glu | Leu | Ser | Pro | Leu | Leu | Leu | Ser | Thr | Thr | Gln | Trp | Gln |
| | 290 | | | | | 295 | | | | | 300 | | | | |
| Val | Leu | Pro | Cys | Ser | Phe | Thr | Thr | Leu | Pro | Ala | Leu | Ser | Thr | Gly | Leu |
| 305 | | | | | 310 | | | | | 315 | | | | | 320 |
| Ile | His | Leu | His | Gln | Asn | Ile | Val | Asp | Val | Gln | Tyr | Leu | Tyr | Gly | Val |
| | | | | 325 | | | | | 330 | | | | | 335 | |
| Gly | Ser | Ser | Ile | Ala | Ser | Trp | Ala | Ile | Lys | Trp | Glu | Tyr | Val | Val | Leu |
| | | | 340 | | | | | 345 | | | | | 350 | | |
| Leu | Phe | Leu | Leu | Leu | Ala | Asp | Ala | Arg | Val | Cys | Ser | Cys | Leu | Trp | Met |
| | | 355 | | | | | 360 | | | | | 365 | | | |
| Met | Leu | Leu | Ile | Ser | Gln | Ala | Glu | Ala | Ala | Leu | Glu | Asn | Leu | Val | Ile |
| | 370 | | | | | 375 | | | | | 380 | | | | |
| Leu | Asn | Ala | Ala | Ser | Leu | Ala | Gly | Thr | His | Gly | Leu | Val | Ser | Phe | Leu |
| 385 | | | | | 390 | | | | | 395 | | | | | 400 |
| Val | Phe | Phe | Cys | Phe | Ala | Trp | Tyr | Leu | | | | | | | |
| | | | | 405 | | | | | | | | | | | |

( 2 ) INFORMATION FOR SEQ ID NO:22:

( i ) SEQUENCE CHARACTERISTICS:
( A ) LENGTH: 480 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:22:

| | | | | | | | | | | | | | | | |
|---|---|---|---|---|---|---|---|---|---|---|---|---|---|---|---|
| Lys | Val | Leu | Ile | Val | Met | Leu | Leu | Phe | Ala | Gly | Val | Asp | Gly | Asp | Thr |
| 1 | | | | 5 | | | | | 10 | | | | | 15 | |
| His | Val | Thr | Gly | Gly | Ala | Gln | Ala | Lys | Thr | Thr | Asn | Arg | Leu | Val | Ser |
| | | | 20 | | | | | 25 | | | | | 30 | | |
| Met | Phe | Ala | Ser | Gly | Pro | Ser | Gln | Lys | Ile | Gln | Leu | Ile | Asn | Thr | Asn |
| | | 35 | | | | | 40 | | | | | 45 | | | |
| Gly | Ser | Trp | His | Ile | Asn | Arg | Thr | Ala | Leu | Asn | Cys | Asn | Asp | Ser | Leu |
| | 50 | | | | | 55 | | | | | 60 | | | | |
| Gln | Thr | Gly | Phe | Leu | Ala | Ala | Leu | Phe | Tyr | Thr | His | Ser | Phe | Asn | Ser |
| 65 | | | | | 70 | | | | | 75 | | | | | 80 |
| Ser | Gly | Cys | Pro | Glu | Arg | Met | Ala | Gln | Cys | Arg | Thr | Ile | Asp | Lys | Phe |
| | | | | 85 | | | | | 90 | | | | | 95 | |
| Asp | Gln | Gly | Trp | Gly | Pro | Ile | Thr | Tyr | Ala | Glu | Ser | Ser | Arg | Ser | Asp |
| | | | 100 | | | | | 105 | | | | | 110 | | |
| Gln | Arg | Pro | Tyr | Cys | Trp | His | Tyr | Pro | Pro | Pro | Gln | Cys | Thr | Ile | Val |
| | | 115 | | | | | 120 | | | | | 125 | | | |
| Pro | Ala | Ser | Glu | Val | Cys | Gly | Pro | Val | Tyr | Cys | Phe | Thr | Pro | Ser | Pro |
| | 130 | | | | | 135 | | | | | 140 | | | | |
| Val | Val | Val | Gly | Thr | Thr | Asp | Arg | Phe | Gly | Val | Pro | Thr | Tyr | Arg | Trp |
| 145 | | | | | 150 | | | | | 155 | | | | | 160 |
| Gly | Glu | Asn | Glu | Thr | Asp | Val | Leu | Leu | Leu | Asn | Asn | Thr | Arg | Pro | Pro |
| | | | | 165 | | | | | 170 | | | | | 175 | |
| Gln | Gly | Asn | Trp | Phe | Gly | Cys | Thr | Trp | Met | Asn | Ser | Thr | Gly | Phe | Thr |
| | | | 180 | | | | | 185 | | | | | 190 | | |
| Lys | Thr | Cys | Gly | Gly | Pro | Pro | Cys | Asn | Ile | Gly | Gly | Val | Gly | Asn | Asn |

-continued 195 200 205

Thr Leu Thr Cys Pro Thr Asp Cys Phe Arg Lys His Pro Glu Ala Thr
210 215 220

Tyr Thr Lys Cys Gly Ser Gly Pro Trp Leu Thr Pro Arg Cys Met Val
225 230 235 240

Asp Tyr Pro Tyr Arg Leu Trp His Tyr Pro Cys Thr Val Asn Phe Thr
245 250 255

Ile Phe Lys Val Arg Met Tyr Val Gly Gly Val Glu His Arg Leu Asn
260 265 270

Ala Ala Cys Asn Trp Thr Arg Gly Glu Arg Cys Asp Leu Glu Asp Arg
275 280 285

Asp Arg Pro Glu Leu Ser Pro Leu Leu Leu Ser Thr Thr Glu Trp Gln
290 295 300

Val Leu Pro Cys Ser Phe Thr Thr Leu Pro Ala Leu Ser Thr Gly Leu
305 310 315 320

Ile His Leu His Gln Asn Ile Val Asp Val Gln Tyr Leu Tyr Gly Ile
325 330 335

Gly Ser Ala Val Val Ser Phe Ala Ile Lys Trp Glu Tyr Val Leu Leu
340 345 350

Leu Phe Leu Leu Leu Ala Asp Ala Arg Val Cys Ala Cys Leu Trp Met
355 360 365

Met Leu Leu Ile Ala Gln Ala Glu Ala Ala Leu Glu Asn Leu Val Val
370 375 380

Leu Asn Ser Ala Ser Val Ala Gly Ala His Gly Ile Leu Ser Phe Leu
385 390 395 400

Val Phe Phe Cys Ala Ala Trp Tyr Ile Lys Gly Arg Leu Val Pro Gly
405 410 415

Ala Thr Tyr Ala Leu Tyr Gly Val Trp Pro Leu Leu Leu Leu Leu Leu
420 425 430

Ala Leu Pro Pro Arg Ala Tyr Ala Met Asp Arg Glu Met Ala Ala Ser
435 440 445

Cys Gly Gly Ala Val Phe Val Gly Leu Val Leu Leu Thr Leu Ser Pro
450 455 460

Tyr Tyr Lys Val Phe Leu Ala Arg Leu Ile Trp Trp Leu Gln Tyr Phe
465 470 475 480

( 2 ) INFORMATION FOR SEQ ID NO:23:

( i ) SEQUENCE CHARACTERISTICS:
( A ) LENGTH: 445 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:23:

Lys Val Leu Val Val Leu Leu Leu Phe Ala Gly Val Asp Ala Thr Thr
1 5 10 15

Tyr Thr Thr Gly Gly Asn Ala Ala Arg Thr Thr Gln Ala Leu Thr Ser
20 25 30

Phe Phe Ser Pro Gly Ala Lys Gln Asp Ile Gln Leu Ile Asn Thr Asn
35 40 45

Gly Ser Trp His Ile Asn Arg Thr Ala Leu Asn Cys Asn Gly Ser Leu
50 55 60

Asp Thr Gly Trp Val Ala Gly Leu Phe Tyr Tyr His Lys Phe Asn Ser
65 70 75 80

-continued

```
Ser Gly Cys Pro Glu Arg Met Ala Ser Cys Arg Pro Leu Ala Asp Phe
                 85                  90                  95

Gln Gln Gly Trp Gly Pro Ile Ser Tyr Ala Asn Gly Ser Gly Pro Glu
            100                 105                 110

His Arg Pro Tyr Cys Trp His Tyr Pro Pro Lys Pro Cys Gly Ile Val
        115                 120                 125

Pro Ala Gln Asn Val Cys Gly Pro Val Tyr Cys Phe Thr Pro Ser Pro
    130                 135                 140

Val Val Val Gly Thr Thr Asn Lys Leu Gly Ala Pro Thr Tyr Asn Trp
145                 150                 155                 160

Gly Ser Asn Glu Thr Asp Val Phe Val Leu Asn Asn Thr Arg Pro Pro
                165                 170                 175

Leu Gly Asn Trp Phe Gly Cys Thr Trp Met Asn Ser Ser Gly Phe Thr
            180                 185                 190

Lys Val Cys Gly Ala Pro Pro Cys Val Ile Gly Gly Val Gly Asn Asn
        195                 200                 205

Thr Leu Gln Cys Pro Thr Asp Cys Phe Arg Lys His Pro Asp Ala Thr
    210                 215                 220

Tyr Ser Arg Cys Ala Ala Gly Pro Trp Ile Thr Pro Arg Cys Leu Val
225                 230                 235                 240

His Tyr Pro Tyr Arg Leu Trp His Tyr Pro Cys Thr Val Asn Tyr Thr
                245                 250                 255

Ile Val Gln Ile Arg Met Tyr Val Gly Gly Val Asp His Arg Leu Glu
            260                 265                 270

Val Ala Cys Asn Trp Thr Arg Gly Glu Arg Cys Asp Leu Asp Asp Arg
        275                 280                 285

Asp Arg Ser Glu Leu Arg Leu Leu Leu Leu Ser Thr Thr Gln Trp Gln
    290                 295                 300

Val Leu Pro Cys Ser Phe Thr Thr Leu Pro Ala Leu Thr Thr Gly Leu
305                 310                 315                 320

Ile His Leu His Gln Asn Ile Val Asp Val Gln Tyr Leu Tyr Gly Val
                325                 330                 335

Gly Ser Ser Ile Val Ser Trp Ala Ile Lys Trp Glu Tyr Val Ile Leu
            340                 345                 350

Leu Phe Leu Leu Leu Ala Asn Ala Arg Ile Cys Ser Cys Leu Trp Met
        355                 360                 365

Met Leu Leu Ile Ser Gln Ala Glu Ala Ala Leu Glu Asn Leu Val Leu
    370                 375                 380

Leu Asn Ala Ala Ser Leu Ala Gly Ala His Ala Val Ala Ser Phe Leu
385                 390                 395                 400

Val Phe Phe Cys Phe Ala Trp Tyr Leu Lys Gly Arg Trp Val Pro Gly
                405                 410                 415

Ala Ala Tyr Ala Phe Tyr Gly Met Trp Pro Leu Leu Leu Leu Leu Leu
            420                 425                 430

Ala Leu Pro Gln Arg Ala Tyr Ala Leu Asp Thr Glu Met
        435                 440                 445
```

( 2 ) INFORMATION FOR SEQ ID NO:24:

( i ) SEQUENCE CHARACTERISTICS:
- ( A ) LENGTH: 409 amino acids
- ( B ) TYPE: amino acid
- ( C ) STRANDEDNESS: single
- ( D ) TOPOLOGY: linear ( i i ) MOLECULE TYPE: protein -continued ( x i ) SEQUENCE DESCRIPTION: SEQ ID NO:24:

Lys Val Leu Val Val Leu Leu Leu Phe Ala Gly Val Asp Ala Glu Thr
1 5 10 15

His Val Thr Gly Gly Ser Ala Gly Arg Thr Thr Ala Gly Leu Val Gly
20 25 30

Leu Leu Thr Pro Gly Ala Lys Gln Asn Ile Gln Leu Ile Asn Thr Asn
35 40 45

Gly Ser Trp His Ile Asn Ser Thr Ala Leu Asn Cys Asn Glu Ser Leu
50 55 60

Asn Thr Gly Trp Leu Ala Gly Leu Phe Tyr His His Lys Phe Asn Ser
65 70 75 80

Ser Gly Cys Pro Glu Arg Leu Ala Ser Cys Arg Arg Leu Thr Asp Phe
85 90 95

Ala Gln Gly Trp Gly Pro Ile Ser Tyr Ala Asn Gly Ser Gly Leu Asp
100 105 110

Glu Arg Pro Tyr Cys Trp His Tyr Pro Pro Arg Pro Cys Gly Ile Val
115 120 125

Pro Ala Lys Ser Val Cys Gly Pro Val Tyr Cys Phe Thr Pro Ser Pro
130 135 140

Val Val Val Gly Thr Thr Asp Arg Ser Gly Ala Pro Thr Tyr Ser Trp
145 150 155 160

Gly Ala Asn Asp Thr Asp Val Phe Val Leu Asn Asn Thr Arg Pro Pro
165 170 175

Leu Gly Asn Trp Phe Gly Cys Thr Trp Met Asn Ser Thr Gly Phe Thr
180 185 190

Lys Val Cys Gly Ala Pro Pro Cys Val Ile Gly Gly Val Gly Asn Asn
195 200 205

Thr Leu Leu Cys Pro Thr Asp Cys Phe Arg Lys His Pro Glu Ala Thr
210 215 220

Tyr Ser Arg Cys Gly Ser Gly Pro Trp Ile Thr Pro Arg Cys Met Val
225 230 235 240

Asp Tyr Pro Tyr Arg Leu Trp His Tyr Pro Cys Thr Ile Asn Tyr Thr
245 250 255

Ile Phe Lys Val Arg Met Tyr Val Gly Gly Val Glu His Arg Leu Glu
260 265 270

Ala Ala Cys Asn Trp Thr Arg Gly Glu Arg Cys Asp Leu Glu Asp Arg
275 280 285

Asp Arg Ser Glu Leu Ser Pro Leu Leu Leu Ser Thr Thr Gln Trp Gln
290 295 300

Val Leu Pro Cys Ser Phe Thr Thr Leu Pro Ala Leu Ser Thr Gly Leu
305 310 315 320

Ile His Leu His Gln Asn Ile Val Asp Val Gln Tyr Leu Tyr Gly Val
325 330 335

Gly Ser Ser Ile Ala Ser Trp Ala Ile Lys Trp Glu Tyr Val Val Leu
340 345 350

Leu Phe Leu Leu Leu Ala Asp Ala Arg Val Cys Ser Cys Leu Trp Met
355 360 365

Met Leu Leu Ile Ser Gln Ala Glu Ala Ala Leu Glu Asn Leu Val Ile
370 375 380

Leu Asn Ala Ala Ser Leu Ala Gly Thr His Gly Leu Val Ser Phe Leu
385 390 395 400

Val Phe Phe Cys Phe Ala Trp Tyr Leu
405

(2) INFORMATION FOR SEQ ID NO:25:

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:25:

```
Glu Thr Tyr Val Ser Gly Gly Ser Ala Ala Gln Thr Thr Ala Gly Phe
1               5                   10                  15

Val Arg Leu Phe Glu Thr Gly Pro Lys Gln Asn Ile Gln Leu Ile
            20                  25                  30
```

(2) INFORMATION FOR SEQ ID NO:26:

(i) SEQUENCE CHARACTERISTICS:
(A) LENGTH: 88 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:26:

```
Trp Met Asn Ser Thr Gly Phe Thr Glu Val Cys Gly Ala Pro Pro Cys
1               5                   10                  15

Val Ile Gly Gly Ala Gly Asn Asn Thr Leu His Cys Pro Thr Asp Cys
            20                  25                  30

Phe Arg Lys His Pro Asp Ala Thr Tyr Ser Arg Cys Gly Ser Gly Pro
        35                  40                  45

Trp Ile Thr Pro Arg Cys Leu Val Asp Tyr Pro Tyr Arg Leu Trp His
    50                  55                  60

Tyr Pro Cys Thr Ile Asn Tyr Thr Ile Phe Lys Ile Arg Met Tyr Val
65                  70                  75                  80

Gly Gly Val Glu His Arg Leu Glu
                85
```

(2) INFORMATION FOR SEQ ID NO:27:

(i) SEQUENCE CHARACTERISTICS:
(A) LENGTH: 88 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:27:

```
Trp Met Asn Ser Thr Gly Phe Thr Lys Val Cys Gly Ala Pro Pro Cys
1               5                   10                  15

Val Ile Gly Gly Ala Gly Asn Asn Thr Leu His Cys Pro Thr Asp Cys
            20                  25                  30

Phe Arg Lys His Pro Asp Ala Thr Tyr Ser Arg Cys Gly Ser Gly Pro
        35                  40                  45

Trp Ile Thr Pro Arg Cys Leu Val Asp Tyr Pro Tyr Arg Leu Trp His
    50                  55                  60

Tyr Pro Cys Thr Ile Asn Tyr Thr Ile Phe Lys Ile Arg Met Tyr Val
65                  70                  75                  80

Gly Gly Val Glu His Arg Leu Glu
```

-continued

85

( 2 ) INFORMATION FOR SEQ ID NO:28:

( i ) SEQUENCE CHARACTERISTICS:
( A ) LENGTH: 31 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:28:

```
Glu Thr Tyr Val Ser Gly Gly Ala Ala Ala Gln Thr Thr Ala Arg Phe
1               5                   10                  15

Ala Gly Phe Phe Gln Ser Gly Ala Lys Gln Asn Ile Gln Leu Ile
            20                  25                  30
```

( 2 ) INFORMATION FOR SEQ ID NO:29:

( i ) SEQUENCE CHARACTERISTICS:
( A ) LENGTH: 268 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Duplication
( B ) LOCATION: 3
( D ) OTHER INFORMATION: /label=heterogeneity
/ note= "Amino acid #3 can also be Arg."

( i x ) FEATURE:
( A ) NAME/KEY: Duplication
( B ) LOCATION: 7
( D ) OTHER INFORMATION: /label=Heterogeneity
/ note= "Amino Acid #5 can also be Ala."

( x i ) SEQUENCE DESCRIPTION: SEQ ID NO:29:

```
Asn Thr His Val Thr Gly Ala Val Gln Gly His Gly Ala Phe Gly Leu
1               5                   10                  15

Thr Ser Leu Phe Gln Pro Gly Ala Ser Gln Lys Ile Gln Leu Val Asn
            20                  25                  30

Thr Asn Gly Ser Trp His Ile Asn Arg Thr Ala Leu Asn Cys Asn Asp
        35                  40                  45

Ser Leu Lys Thr Gly Phe Leu Ala Ala Leu Phe Tyr Thr His Arg Phe
    50                  55                  60

Asn Ala Ser Gly Cys Pro Glu Arg Met Ala Ser Cys Arg Ser Ile Asp
65                  70                  75                  80

Lys Phe Asp Gln Gly Trp Gly Pro Ile Thr Tyr Ala Gln Pro Asp Asn
                85                  90                  95

Ser Asp Gln Arg Pro Tyr Cys Trp His Tyr Thr Pro Arg Gln Cys Gly
            100                 105                 110

Ile Val Pro Ala Ser Gln Val Cys Gly Pro Val Tyr Cys Phe Thr Pro
        115                 120                 125

Ser Pro Val Val Val Gly Thr Thr Asp Arg Ser Gly Ala Pro Thr Tyr
    130                 135                 140

Asn Trp Gly Asp Asn Glu Thr Asp Val Leu Leu Leu Asn Asn Thr Arg
145                 150                 155                 160

Pro Pro His Gly Asn Trp Phe Gly Cys Thr Trp Met Asn Ser Thr Gly
                165                 170                 175

Phe Thr Lys Thr Cys Gly Gly Pro Pro Cys Asn Ile Gly Gly Val Gly
```

-continued 180 185 190

Asn Asn Thr Leu Thr Cys Pro Thr Asp Cys Phe Arg Lys His Pro Asp
195 200 205

Ala Thr Tyr Thr Lys Cys Gly Ser Gly Pro Trp Leu Thr Pro Arg Cys
210 215 220

Leu Val Asp Tyr Pro Tyr Arg Leu Trp His Tyr Pro Cys Thr Val Asn
225 230 235 240

Phe Thr Ile Phe Lys Val Arg Met Tyr Val Gly Gly Val Glu His Arg
245 250 255

Leu Asp Ala Ala Cys Asn Trp Thr Arg Gly Glu Arg
260 265

( 2 ) INFORMATION FOR SEQ ID NO:30:

( i ) SEQUENCE CHARACTERISTICS:
( A ) LENGTH: 268 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Duplication
( B ) LOCATION: 5
( D ) OTHER INFORMATION: /label=Heterogeneity
/ note= "This amino acid can also be Met."

( i x ) FEATURE:
( A ) NAME/KEY: Duplication
( B ) LOCATION: 79
( D ) OTHER INFORMATION: /label=Heterogeneity
/ note= "This amino acid can also be Val."

( i x ) FEATURE:
( A ) NAME/KEY: Duplication
( B ) LOCATION: 80
( D ) OTHER INFORMATION: /label=Heterogeneity
/ note= "This amino acid can also be Gly."

( i x ) FEATURE:
( A ) NAME/KEY: Duplication
( B ) LOCATION: 93
( D ) OTHER INFORMATION: /label=Heterogeneity
/ note= "This amino acid can also be Gln."

( i x ) FEATURE:
( A ) NAME/KEY: Duplication
( B ) LOCATION: 139
( D ) OTHER INFORMATION: /label=Heterogeneity
/ note= "This amino acid can only be Phe."

( i x ) FEATURE:
( A ) NAME/KEY: Duplication
( B ) LOCATION: 141
( D ) OTHER INFORMATION: /label=Heterogeneity
/ note= "This amino acid can also be Val."

( i x ) FEATURE:
( A ) NAME/KEY: Duplication
( B ) LOCATION: 191
( D ) OTHER INFORMATION: /label=Heterogeneity
/ note= "This amino acid can also be Ala."

( i x ) FEATURE:
( A ) NAME/KEY: Duplication
( B ) LOCATION: 197
( D ) OTHER INFORMATION: /label=Heterogeneity
/ note= "This amino acid can also be Thr."

( i x ) FEATURE:
( A ) NAME/KEY: Duplication
( B ) LOCATION: 208
( D ) OTHER INFORMATION: /label=Heterogeneity / note= "This amino acid can also be Arg and Asp."

( i x ) FEATURE:
( A ) NAME/KEY: Duplication
( B ) LOCATION: 233
( D ) OTHER INFORMATION: /label=Heterogeneity
/ note= "This amino acid can also be Trp."

( i x ) FEATURE:
( A ) NAME/KEY: Duplication
( B ) LOCATION: 247
( D ) OTHER INFORMATION: /label=Heterogeneity
/ note= "This amino acid can also be Lys."

( i x ) FEATURE:
( A ) NAME/KEY: Duplication
( B ) LOCATION: 251
( D ) OTHER INFORMATION: /label=Heterogeneity
/ note= "This amino acid can also be Gly."

( x i ) SEQUENCE DESCRIPTION: SEQ ID NO:30:

His Thr Arg Val Met Gly Gly Val Gln Gly His Val Thr Ser Thr Leu
1 5 10 15

Thr Ser Leu Phe Arg Pro Gly Ala Ser Gln Lys Ile Gln Leu Val Asn
20 25 30

Thr Asn Gly Ser Trp His Ile Asn Arg Thr Ala Leu Asn Cys Asn Asp
35 40 45

Ser Leu Gln Thr Gly Phe Leu Ala Ala Leu Phe Tyr Thr His Lys Phe
50 55 60

Asn Ala Ser Gly Cys Pro Glu Arg Met Ala Ser Cys Arg Ser Ile Asp
65 70 75 80

Lys Phe Asp Gln Gly Trp Gly Pro Ile Thr Tyr Ala Arg Pro Asp Asn
85 90 95

Ser Asp Gln Arg Pro Tyr Cys Trp His Tyr Ala Pro Arg Gln Cys Gly
100 105 110

Ile Val Pro Ala Ser Gln Val Cys Gly Pro Val Tyr Cys Phe Thr Pro
115 120 125

Ser Pro Val Val Val Gly Thr Thr Asp Arg Ser Gly Ala Pro Thr Tyr
130 135 140

Asn Trp Gly Asp Asn Glu Thr Asp Val Leu Leu Leu Asn Asn Thr Arg
145 150 155 160

Pro Pro His Gly Asn Trp Phe Gly Cys Thr Trp Met Asn Ser Thr Gly
165 170 175

Phe Thr Lys Thr Cys Gly Gly Pro Pro Cys Asn Ile Gly Gly Val Gly
180 185 190

Asn Asn Thr Leu Ile Cys Pro Thr Asp Cys Phe Arg Lys His Pro Glu
195 200 205

Ala Thr Tyr Thr Lys Cys Gly Ser Gly Pro Trp Leu Thr Pro Arg Cys
210 215 220

Leu Val Asp Tyr Pro Tyr Arg Leu Arg His Tyr Pro Cys Thr Val Asn
225 230 235 240

Phe Thr Ile Phe Lys Val Arg Met Tyr Val Glu Gly Val Glu His Arg
245 250 255

Leu Asp Ala Ala Cys Asn Trp Thr Arg Gly Glu Arg
260 265

( 2 ) INFORMATION FOR SEQ ID NO:31:

( i ) SEQUENCE CHARACTERISTICS:
( A ) LENGTH: 353 amino acids
( B ) TYPE: amino acid
( C ) STRANDEDNESS: single -continued ( D ) TOPOLOGY: linear ( i i ) MOLECULE TYPE: protein ( x i ) SEQUENCE DESCRIPTION: SEQ ID NO:31:

| | | | | | | | | | | | | | | | |
|---|---|---|---|---|---|---|---|---|---|---|---|---|---|---|---|
| Glu | Thr | Tyr | Thr | Thr | Gly | Gly | Ser | Thr | Ala | Arg | Thr | Thr | Gln | Gly | Leu |
| 1 | | | | 5 | | | | | 10 | | | | | 15 | |
| Val | Ser | Leu | Phe | Ser | Arg | Gly | Ala | Lys | Gln | Asp | Ile | Gln | Leu | Ile | Asn |
| | | | 20 | | | | | 25 | | | | | 30 | | |
| Thr | Asn | Gly | Ser | Trp | His | Ile | Asn | Arg | Thr | Ala | Leu | Asn | Cys | Asn | Glu |
| | | 35 | | | | | 40 | | | | | 45 | | | |
| Ser | Leu | Asp | Thr | Gly | Trp | Val | Ala | Gly | Leu | Phe | Tyr | Tyr | His | Lys | Phe |
| | 50 | | | | | 55 | | | | | 60 | | | | |
| Asn | Ser | Ser | Gly | Cys | Pro | Glu | Arg | Met | Ala | Ser | Cys | Arg | Pro | Leu | Ala |
| 65 | | | | | 70 | | | | | 75 | | | | | 80 |
| Asp | Phe | Asp | Gln | Gly | Trp | Gly | Pro | Ile | Ser | Tyr | Ala | Asn | Gly | Thr | Gly |
| | | | | 85 | | | | | 90 | | | | | 95 | |
| Pro | Glu | His | Arg | Pro | Tyr | Cys | Trp | His | Tyr | Pro | Pro | Lys | Pro | Cys | Gly |
| | | | 100 | | | | | 105 | | | | | 110 | | |
| Ile | Val | Pro | Ala | Gln | Thr | Val | Cys | Gly | Pro | Val | Tyr | Cys | Phe | Thr | Pro |
| | | 115 | | | | | 120 | | | | | 125 | | | |
| Ser | Pro | Val | Val | Val | Gly | Thr | Thr | Asn | Lys | Leu | Gly | Ala | Pro | Thr | Tyr |
| | 130 | | | | | 135 | | | | | 140 | | | | |
| Asn | Trp | Gly | Cys | Asn | Asp | Thr | Asp | Val | Phe | Val | Leu | Asn | Asn | Thr | Arg |
| 145 | | | | | 150 | | | | | 155 | | | | | 160 |
| Pro | Pro | Leu | Gly | Asn | Trp | Phe | Gly | Cys | Thr | Trp | Val | Asn | Ser | Ser | Gly |
| | | | | 165 | | | | | 170 | | | | | 175 | |
| Phe | Thr | Lys | Val | Cys | Gly | Ala | Pro | Pro | Cys | Val | Ile | Gly | Gly | Ala | Gly |
| | | | 180 | | | | | 185 | | | | | 190 | | |
| Asn | Asn | Thr | Leu | Tyr | Cys | Pro | Thr | Asp | Cys | Phe | Arg | Lys | His | Pro | Glu |
| | | 195 | | | | | 200 | | | | | 205 | | | |
| Ala | Thr | Tyr | Ser | Arg | Cys | Gly | Ser | Gly | Pro | Trp | Ile | Thr | Pro | Arg | Cys |
| | 210 | | | | | 215 | | | | | 220 | | | | |
| Leu | Val | Gly | Tyr | Pro | Tyr | Arg | Leu | Trp | His | Tyr | Pro | Cys | Thr | Val | Asn |
| 225 | | | | | 230 | | | | | 235 | | | | | 240 |
| Tyr | Thr | Leu | Phe | Lys | Val | Arg | Met | Tyr | Val | Gly | Gly | Val | Glu | His | Arg |
| | | | | 245 | | | | | 250 | | | | | 255 | |
| Leu | Gln | Val | Ala | Cys | Asn | Trp | Thr | Arg | Gly | Glu | Arg | Cys | Asn | Leu | Asp |
| | | | 260 | | | | | 265 | | | | | 270 | | |
| Asp | Arg | Asp | Arg | Ser | Glu | Leu | Ser | Pro | Leu | Leu | Leu | Ser | Thr | Thr | Gln |
| | | 275 | | | | | 280 | | | | | 285 | | | |
| Trp | Gln | Val | Leu | Pro | Cys | Ser | Phe | Thr | Thr | Leu | Pro | Ala | Leu | Thr | Thr |
| | 290 | | | | | 295 | | | | | 300 | | | | |
| Gly | Leu | Ile | His | Leu | His | Gln | Asn | Ile | Val | Asp | Val | Gln | Tyr | Leu | Tyr |
| 305 | | | | | 310 | | | | | 315 | | | | | 320 |
| Gly | Val | Gly | Ser | Ser | Ile | Val | Ser | Trp | Ala | Ile | Lys | Trp | Glu | Tyr | Val |
| | | | | 325 | | | | | 330 | | | | | 335 | |
| Ile | Leu | Leu | Phe | Leu | Leu | Leu | Ala | Asp | Ala | Arg | Val | Cys | Ser | Cys | Leu |
| | | | 340 | | | | | 345 | | | | | 350 | | |
| Trp | | | | | | | | | | | | | | | |

( 2 ) INFORMATION FOR SEQ ID NO:32:

( i ) SEQUENCE CHARACTERISTICS:

( A ) LENGTH: 353 amino acids ( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:32:

Thr Thr Tyr Thr Thr Gly Gly Asn Ala Ala Arg Thr Thr Gln Ala Leu
1 5 10 15

Thr Ser Phe Phe Ser Pro Gly Ala Lys Gln Asp Ile Gln Leu Ile Asn
20 25 30

Thr Asn Gly Ser Trp His Ile Asn Arg Thr Ala Leu Asn Cys Asn Gly
35 40 45

Ser Leu Asp Thr Gly Trp Val Ala Gly Leu Phe Tyr Tyr His Lys Phe
50 55 60

Asn Ser Ser Gly Cys Pro Glu Arg Met Ala Ser Cys Arg Pro Leu Ala
65 70 75 80

Asp Phe Gln Gln Gly Trp Gly Pro Ile Ser Tyr Ala Asn Gly Ser Gly
85 90 95

Pro Glu His Arg Pro Tyr Cys Trp His Tyr Pro Pro Lys Pro Cys Gly
100 105 110

Ile Val Pro Ala Gln Asn Val Cys Gly Pro Val Tyr Cys Phe Thr Pro
115 120 125

Ser Pro Val Val Val Gly Thr Thr Asn Lys Leu Gly Ala Pro Thr Tyr
130 135 140

Asn Trp Gly Ser Asn Glu Thr Asp Val Phe Val Leu Asn Asn Thr Arg
145 150 155 160

Pro Pro Leu Gly Asn Trp Phe Gly Cys Thr Trp Met Asn Ser Ser Gly
165 170 175

Phe Thr Lys Val Cys Gly Ala Pro Pro Cys Val Ile Gly Gly Val Gly
180 185 190

Asn Asn Thr Leu Gln Cys Pro Thr Asp Cys Phe Arg Lys His Pro Asp
195 200 205

Ala Thr Tyr Ser Arg Cys Ala Ala Gly Pro Trp Ile Thr Pro Arg Cys
210 215 220

Leu Val His Tyr Pro Tyr Arg Leu Trp His Tyr Pro Cys Thr Val Asn
225 230 235 240

Tyr Thr Ile Val Gln Ile Arg Met Tyr Val Gly Gly Val Asp His Arg
245 250 255

Leu Glu Val Ala Cys Asn Trp Thr Arg Gly Glu Arg Cys Asp Leu Asp
260 265 270

Asp Arg Asp Arg Ser Glu Leu Arg Leu Leu Leu Leu Ser Thr Thr Gln
275 280 285

Trp Gln Val Leu Pro Cys Ser Phe Thr Thr Leu Pro Ala Leu Thr Thr
290 295 300

Gly Leu Ile His Leu His Gln Asn Ile Val Asp Val Gln Tyr Leu Tyr
305 310 315 320

Gly Val Gly Ser Ser Ile Val Ser Trp Ala Ile Lys Trp Glu Tyr Val
325 330 335

Ile Leu Leu Phe Leu Leu Leu Ala Asn Ala Arg Ile Cys Ser Cys Leu
340 345 350

Trp ( 2 ) INFORMATION FOR SEQ ID NO:33:

( i ) SEQUENCE CHARACTERISTICS:
( A ) LENGTH: 32 amino acids ( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:33:

Glu Thr Tyr Thr Ser Gly Gly Asn Ala Gly His Thr Met Thr Gly Ile
1 5 10 15

Val Arg Phe Phe Ala Pro Gly Pro Lys Gln Asn Val His Leu Ile Asn
20 25 30

( 2 ) INFORMATION FOR SEQ ID NO:34:

( i ) SEQUENCE CHARACTERISTICS:
( A ) LENGTH: 33 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:34:

Glu Thr Thr Val Thr Gly Gly Ser Ala Ala His Gly Ala Leu Gly Ile
1 5 10 15

Ala Ser Leu Phe Asn Cys Gly Ala Arg Cys Asn Ile Cys Leu Ile Asn
20 25 30

Thr ( 2 ) INFORMATION FOR SEQ ID NO:35:

( i ) SEQUENCE CHARACTERISTICS:
( A ) LENGTH: 32 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:35:

His Thr Arg Val Thr Gly Gly Val Gln Gly His Val Thr Ser Thr Leu
1 5 10 15

Thr Ser Leu Phe Arg Pro Gly Ala Ser Gln Lys Ile Gln Leu Val Asn
20 25 30

( 2 ) INFORMATION FOR SEQ ID NO:36:

( i ) SEQUENCE CHARACTERISTICS:
( A ) LENGTH: 3011 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:36:

Met Ser Thr Asn Pro Lys Pro Gln Lys Lys Asn Lys Arg Asn Thr Asn
1 5 10 15

Arg Arg Pro Gln Asp Val Lys Phe Pro Gly Gly Gly Gln Ile Val Gly
20 25 30

Gly Val Tyr Leu Leu Pro Arg Arg Gly Pro Arg Leu Gly Val Arg Ala
35 40 45

Thr Arg Lys Thr Ser Glu Arg Ser Gln Pro Arg Gly Arg Arg Gln Pro
50 55 60

Ile Pro Lys Ala Arg Arg Pro Glu Gly Arg Thr Trp Ala Gln Pro Gly

-continued 65 70 75 80

Tyr Pro Trp Pro Leu Tyr Gly Asn Glu Gly Cys Gly Trp Ala Gly Trp
85 90 95

Leu Leu Ser Pro Arg Gly Ser Arg Pro Ser Trp Gly Pro Thr Asp Pro
100 105 110

Arg Arg Arg Ser Arg Asn Leu Gly Lys Val Ile Asp Thr Leu Thr Cys
115 120 125

Gly Phe Ala Asp Leu Met Gly Tyr Ile Pro Leu Val Gly Ala Pro Leu
130 135 140

Gly Gly Ala Ala Arg Ala Leu Ala His Gly Val Arg Val Leu Glu Asp
145 150 155 160

Gly Val Asn Tyr Ala Thr Gly Asn Leu Pro Gly Cys Ser Phe Ser Ile
165 170 175

Phe Leu Leu Ala Leu Leu Ser Cys Leu Thr Val Pro Ala Ser Ala Tyr
180 185 190

Gln Val Arg Asn Ser Thr Gly Leu Tyr His Val Thr Asn Asp Cys Pro
195 200 205

Asn Ser Ser Ile Val Tyr Glu Ala Ala Asp Ala Ile Leu His Thr Pro
210 215 220

Gly Cys Val Pro Cys Val Arg Glu Gly Asn Ala Ser Arg Cys Trp Val
225 230 235 240

Ala Met Thr Pro Thr Val Ala Thr Arg Asp Gly Lys Leu Pro Ala Thr
245 250 255

Gln Leu Arg Arg His Ile Asp Leu Leu Val Gly Ser Ala Thr Leu Cys
260 265 270

Ser Ala Leu Tyr Val Gly Asp Leu Cys Gly Ser Val Phe Leu Val Gly
275 280 285

Gln Leu Phe Thr Phe Ser Pro Arg Arg His Trp Thr Thr Gln Gly Cys
290 295 300

Asn Cys Ser Ile Tyr Pro Gly His Ile Thr Gly His Arg Met Ala Trp
305 310 315 320

Asp Met Met Met Asn Trp Ser Pro Thr Thr Ala Leu Val Met Ala Gln
325 330 335

Leu Leu Arg Ile Pro Gln Ala Ile Leu Asp Met Ile Ala Gly Ala His
340 345 350

Trp Gly Val Leu Ala Gly Ile Ala Tyr Phe Ser Met Val Gly Asn Trp
355 360 365

Ala Lys Val Leu Val Val Leu Leu Leu Phe Ala Gly Val Asp Ala Glu
370 375 380

Thr His Val Thr Gly Gly Ser Ala Gly His Thr Val Ser Gly Phe Val
385 390 395 400

Ser Leu Leu Ala Pro Gly Ala Lys Gln Asn Val Gln Leu Ile Asn Thr
405 410 415

Asn Gly Ser Trp His Leu Asn Ser Thr Ala Leu Asn Cys Asn Asp Ser
420 425 430

Leu Asn Thr Gly Trp Leu Ala Gly Leu Phe Tyr His His Lys Phe Asn
435 440 445

Ser Ser Gly Cys Pro Glu Arg Leu Ala Ser Cys Arg Pro Leu Thr Asp
450 455 460

Phe Asp Gln Gly Trp Gly Pro Ile Ser Tyr Ala Asn Gly Ser Gly Pro
465 470 475 480

Asp Gln Arg Pro Tyr Cys Trp His Tyr Pro Pro Lys Pro Cys Gly Ile
485 490 495

-continued

| | | | | | | | | | | | | | | | |
|---|---|---|---|---|---|---|---|---|---|---|---|---|---|---|---|
| Val | Pro | Ala | Lys | Ser | Val | Cys | Gly | Pro | Val | Tyr | Cys | Phe | Thr | Pro | Ser |
| | | | 500 | | | | | 505 | | | | | 510 | | |
| Pro | Val | Val | Val | Gly | Thr | Thr | Asp | Arg | Ser | Gly | Ala | Pro | Thr | Tyr | Ser |
| | | 515 | | | | | 520 | | | | | 525 | | | |
| Trp | Gly | Glu | Asn | Asp | Thr | Asp | Val | Phe | Val | Leu | Asn | Asn | Thr | Arg | Pro |
| | 530 | | | | | 535 | | | | | 540 | | | | |
| Pro | Leu | Gly | Asn | Trp | Phe | Gly | Cys | Thr | Trp | Met | Asn | Ser | Thr | Gly | Phe |
| 545 | | | | | 550 | | | | | 555 | | | | | 560 |
| Thr | Lys | Val | Cys | Gly | Ala | Pro | Pro | Cys | Val | Ile | Gly | Gly | Ala | Gly | Asn |
| | | | | 565 | | | | | 570 | | | | | 575 | |
| Asn | Thr | Leu | His | Cys | Pro | Thr | Asp | Cys | Phe | Arg | Lys | His | Pro | Asp | Ala |
| | | | 580 | | | | | 585 | | | | | 590 | | |
| Thr | Tyr | Ser | Arg | Cys | Gly | Ser | Gly | Pro | Trp | Ile | Thr | Pro | Arg | Cys | Leu |
| | | 595 | | | | | 600 | | | | | 605 | | | |
| Val | Asp | Tyr | Pro | Tyr | Arg | Leu | Trp | His | Tyr | Pro | Cys | Thr | Ile | Asn | Tyr |
| | 610 | | | | | 615 | | | | | 620 | | | | |
| Thr | Ile | Phe | Lys | Ile | Arg | Met | Tyr | Val | Gly | Gly | Val | Glu | His | Arg | Leu |
| 625 | | | | | 630 | | | | | 635 | | | | | 640 |
| Glu | Ala | Ala | Cys | Asn | Trp | Thr | Arg | Gly | Glu | Arg | Cys | Asp | Leu | Glu | Asp |
| | | | | 645 | | | | | 650 | | | | | 655 | |
| Arg | Asp | Arg | Ser | Glu | Leu | Ser | Pro | Leu | Leu | Leu | Thr | Thr | Thr | Gln | Trp |
| | | | 660 | | | | | 665 | | | | | 670 | | |
| Gln | Val | Leu | Pro | Cys | Ser | Phe | Thr | Thr | Leu | Pro | Ala | Leu | Ser | Thr | Gly |
| | | 675 | | | | | 680 | | | | | 685 | | | |
| Leu | Ile | His | Leu | His | Gln | Asn | Ile | Val | Asp | Val | Gln | Tyr | Leu | Tyr | Gly |
| | 690 | | | | | 695 | | | | | 700 | | | | |
| Val | Gly | Ser | Ser | Ile | Ala | Ser | Trp | Ala | Ile | Lys | Trp | Glu | Tyr | Val | Val |
| 705 | | | | | 710 | | | | | 715 | | | | | 720 |
| Leu | Leu | Phe | Leu | Leu | Leu | Ala | Asp | Ala | Arg | Val | Cys | Ser | Cys | Leu | Trp |
| | | | | 725 | | | | | 730 | | | | | 735 | |
| Met | Met | Leu | Leu | Ile | Ser | Gln | Ala | Glu | Ala | Ala | Leu | Glu | Asn | Leu | Val |
| | | | 740 | | | | | 745 | | | | | 750 | | |
| Ile | Leu | Asn | Ala | Ala | Ser | Leu | Ala | Gly | Thr | His | Gly | Leu | Val | Ser | Phe |
| | | 755 | | | | | 760 | | | | | 765 | | | |
| Leu | Val | Phe | Phe | Cys | Phe | Ala | Trp | Tyr | Leu | Lys | Gly | Lys | Trp | Val | Pro |
| | 770 | | | | | 775 | | | | | 780 | | | | |
| Gly | Ala | Val | Tyr | Thr | Phe | Tyr | Gly | Met | Trp | Pro | Leu | Leu | Leu | Leu | Leu |
| 785 | | | | | 790 | | | | | 795 | | | | | 800 |
| Leu | Ala | Leu | Pro | Gln | Arg | Ala | Tyr | Ala | Leu | Asp | Thr | Glu | Val | Ala | Ala |
| | | | | 805 | | | | | 810 | | | | | 815 | |
| Ser | Cys | Gly | Gly | Val | Val | Leu | Val | Gly | Leu | Met | Ala | Leu | Thr | Leu | Ser |
| | | | 820 | | | | | 825 | | | | | 830 | | |
| Pro | Tyr | Tyr | Lys | Arg | Tyr | Ile | Ser | Trp | Cys | Leu | Trp | Trp | Leu | Gln | Tyr |
| | | 835 | | | | | 840 | | | | | 845 | | | |
| Phe | Leu | Thr | Arg | Val | Glu | Ala | Gln | Leu | His | Val | Trp | Ile | Pro | Pro | Leu |
| | 850 | | | | | 855 | | | | | 860 | | | | |
| Asn | Val | Arg | Gly | Gly | Arg | Asp | Ala | Val | Ile | Leu | Leu | Met | Cys | Ala | Val |
| 865 | | | | | 870 | | | | | 875 | | | | | 880 |
| His | Pro | Thr | Leu | Val | Phe | Asp | Ile | Thr | Lys | Leu | Leu | Leu | Ala | Val | Phe |
| | | | | 885 | | | | | 890 | | | | | 895 | |
| Gly | Pro | Leu | Trp | Ile | Leu | Gln | Ala | Ser | Leu | Leu | Lys | Val | Pro | Tyr | Phe |
| | | | 900 | | | | | 905 | | | | | 910 | | |
| Val | Arg | Val | Gln | Gly | Leu | Leu | Arg | Phe | Cys | Ala | Leu | Ala | Arg | Lys | Met |
| | | 915 | | | | | 920 | | | | | 925 | | | |

-continued

```
Ile Gly Gly His Tyr Val Gln Met Val Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Gln Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Arg
        995                 1000                1005

Glu Ile Leu Leu Gly Pro Ala Asp Gly Met Val Ser Lys Gly Trp Arg
    1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
                1045                1050                1055

Gly Glu Val Gln Ile Val Ser Thr Ala Ala Gln Thr Phe Leu Ala Thr
            1060                1065                1070

Cys Ile Asn Gly Val Cys Trp Thr Val Tyr His Gly Ala Gly Thr Arg
        1075                1080                1085

Thr Ile Ala Ser Pro Lys Gly Pro Val Ile Gln Met Tyr Thr Asn Val
    1090                1095                1100

Asp Gln Asp Leu Val Gly Trp Pro Ala Pro Gln Gly Ser Arg Ser Leu
1105                1110                1115                1120

Thr Pro Cys Thr Cys Gly Ser Ser Asp Leu Tyr Leu Val Thr Arg His
                1125                1130                1135

Ala Asp Val Ile Pro Val Arg Arg Arg Gly Asp Ser Arg Gly Ser Leu
            1140                1145                1150

Leu Ser Pro Arg Pro Ile Ser Tyr Leu Lys Gly Ser Ser Gly Gly Pro
        1155                1160                1165

Leu Leu Cys Pro Ala Gly His Ala Val Gly Ile Phe Arg Ala Ala Val
    1170                1175                1180

Cys Thr Arg Gly Val Ala Lys Ala Val Asp Phe Ile Pro Val Glu Asn
1185                1190                1195                1200

Leu Glu Thr Thr Met Arg Ser Pro Val Phe Thr Asp Asn Ser Ser Pro
                1205                1210                1215

Pro Val Val Pro Gln Ser Phe Gln Val Ala His Leu His Ala Pro Thr
            1220                1225                1230

Gly Ser Gly Lys Ser Thr Lys Val Pro Ala Ala Tyr Ala Ala Gln Gly
        1235                1240                1245

Tyr Lys Val Leu Val Leu Asn Pro Ser Val Ala Ala Thr Leu Gly Phe
    1250                1255                1260

Gly Ala Tyr Met Ser Lys Ala His Gly Ile Asp Pro Asn Ile Arg Thr
1265                1270                1275                1280

Gly Val Arg Thr Ile Thr Thr Gly Ser Pro Ile Thr Tyr Ser Thr Tyr
                1285                1290                1295

Gly Lys Phe Leu Ala Asp Gly Gly Cys Ser Gly Gly Ala Tyr Asp Ile
            1300                1305                1310

Ile Ile Cys Asp Glu Cys His Ser Thr Asp Ala Thr Ser Ile Leu Gly
        1315                1320                1325

Ile Gly Thr Val Leu Asp Gln Ala Glu Thr Ala Gly Ala Arg Leu Val
    1330                1335                1340

Val Leu Ala Thr Ala Thr Pro Pro Gly Ser Val Thr Val Pro His Pro
```

-continued

```
1345                     1350                     1355                     1360

Asn Ile Glu Glu Val Ala Leu Ser Thr Thr Gly Glu Ile Pro Phe Tyr
                1365                     1370                     1375

Gly Lys Ala Ile Pro Leu Glu Val Ile Lys Gly Gly Arg His Leu Ile
            1380                     1385                     1390

Phe Cys His Ser Lys Lys Lys Cys Asp Glu Leu Ala Ala Lys Leu Val
        1395                     1400                     1405

Ala Leu Gly Ile Asn Ala Val Ala Tyr Tyr Arg Gly Leu Asp Val Ser
    1410                     1415                     1420

Val Ile Pro Thr Ser Gly Asp Val Val Val Val Ala Thr Asp Ala Leu
1425                     1430                     1435                     1440

Met Thr Gly Tyr Thr Gly Asp Phe Asp Ser Val Ile Asp Cys Asn Thr
                1445                     1450                     1455

Cys Val Thr Gln Thr Val Asp Phe Ser Leu Asp Pro Thr Phe Thr Ile
            1460                     1465                     1470

Glu Thr Ile Thr Leu Pro Gln Asp Ala Val Ser Arg Thr Gln Arg Arg
        1475                     1480                     1485

Gly Arg Thr Gly Arg Gly Lys Pro Gly Ile Tyr Arg Phe Val Ala Pro
    1490                     1495                     1500

Gly Glu Arg Pro Ser Gly Met Phe Asp Ser Ser Val Leu Cys Glu Cys
1505                     1510                     1515                     1520

Tyr Asp Ala Gly Cys Ala Trp Tyr Glu Leu Thr Pro Ala Glu Thr Thr
                1525                     1530                     1535

Val Arg Leu Arg Ala Tyr Met Asn Thr Pro Gly Leu Pro Val Cys Gln
            1540                     1545                     1550

Asp His Leu Glu Phe Trp Glu Gly Val Phe Thr Gly Leu Thr His Ile
        1555                     1560                     1565

Asp Ala His Phe Leu Ser Gln Thr Lys Gln Ser Gly Glu Asn Leu Pro
    1570                     1575                     1580

Tyr Leu Val Ala Tyr Gln Ala Thr Val Cys Ala Arg Ala Gln Ala Pro
1585                     1590                     1595                     1600

Pro Pro Ser Trp Asp Gln Met Trp Lys Cys Leu Ile Arg Leu Lys Pro
                1605                     1610                     1615

Thr Leu His Gly Pro Thr Pro Leu Leu Tyr Arg Leu Gly Ala Val Gln
            1620                     1625                     1630

Asn Glu Ile Thr Leu Thr His Pro Val Thr Lys Tyr Ile Met Thr Cys
        1635                     1640                     1645

Met Ser Ala Asp Leu Glu Val Val Thr Ser Thr Trp Val Leu Val Gly
    1650                     1655                     1660

Gly Val Leu Ala Ala Leu Ala Ala Tyr Cys Leu Ser Thr Gly Cys Val
1665                     1670                     1675                     1680

Val Ile Val Gly Arg Val Val Leu Ser Gly Lys Pro Ala Ile Ile Pro
                1685                     1690                     1695

Asp Arg Glu Val Leu Tyr Arg Glu Phe Asp Glu Met Glu Glu Cys Ser
            1700                     1705                     1710

Gln His Leu Pro Tyr Ile Glu Gln Gly Met Met Leu Ala Glu Gln Phe
        1715                     1720                     1725

Lys Gln Lys Ala Leu Gly Leu Leu Gln Thr Ala Ser Arg Gln Ala Glu
    1730                     1735                     1740

Val Ile Ala Pro Ala Val Gln Thr Asn Trp Gln Lys Leu Glu Thr Phe
1745                     1750                     1755                     1760

Trp Ala Lys His Met Trp Asn Phe Ile Ser Gly Ile Gln Tyr Leu Ala
                1765                     1770                     1775
```

-continued

Gly Leu Ser Thr Leu Pro Gly Asn Pro Ala Ile Ala Ser Leu Met Ala
1780 1785 1790

Phe Thr Ala Ala Val Thr Ser Pro Leu Thr Thr Ser Gln Thr Leu Leu
1795 1800 1805

Phe Asn Ile Leu Gly Gly Trp Val Ala Ala Gln Leu Ala Ala Pro Gly
1810 1815 1820

Ala Ala Thr Ala Phe Val Gly Ala Gly Leu Ala Gly Ala Ala Ile Gly
1825 1830 1835 1840

Ser Val Gly Leu Gly Lys Val Leu Ile Asp Ile Leu Ala Gly Tyr Gly
1845 1850 1855

Ala Gly Val Ala Gly Ala Leu Val Ala Phe Lys Ile Met Ser Gly Glu
1860 1865 1870

Val Pro Ser Thr Glu Asp Leu Val Asn Leu Leu Pro Ala Ile Leu Ser
1875 1880 1885

Pro Gly Ala Leu Val Val Gly Val Val Cys Ala Ala Ile Leu Arg Arg
1890 1895 1900

His Val Gly Pro Gly Glu Gly Ala Val Gln Trp Met Asn Arg Leu Ile
1905 1910 1915 1920

Ala Phe Ala Ser Arg Gly Asn His Val Ser Pro Thr His Tyr Val Pro
1925 1930 1935

Glu Ser Asp Ala Ala Ala Arg Val Thr Ala Ile Leu Ser Ser Leu Thr
1940 1945 1950

Val Thr Gln Leu Leu Arg Arg Leu His Gln Trp Ile Ser Ser Glu Cys
1955 1960 1965

Thr Thr Pro Cys Ser Gly Ser Trp Leu Arg Asp Ile Trp Asp Trp Ile
1970 1975 1980

Cys Glu Val Leu Ser Asp Phe Lys Thr Trp Leu Lys Ala Lys Leu Met
1985 1990 1995 2000

Pro Gln Leu Pro Gly Ile Pro Phe Val Ser Cys Gln Arg Gly Tyr Lys
2005 2010 2015

Gly Val Trp Arg Val Asp Gly Ile Met His Thr Arg Cys His Cys Gly
2020 2025 2030

Ala Glu Ile Thr Gly His Val Lys Asn Gly Thr Met Arg Ile Val Gly
2035 2040 2045

Pro Arg Thr Cys Arg Asn Met Trp Ser Gly Thr Phe Pro Ile Asn Ala
2050 2055 2060

Tyr Thr Thr Gly Pro Cys Thr Pro Leu Pro Ala Pro Asn Tyr Thr Phe
2065 2070 2075 2080

Ala Leu Trp Arg Val Ser Ala Glu Glu Tyr Val Glu Ile Arg Gln Val
2085 2090 2095

Gly Asp Phe His Tyr Val Thr Gly Met Thr Thr Asp Asn Leu Lys Cys
2100 2105 2110

Pro Cys Gln Val Pro Ser Pro Glu Phe Phe Thr Glu Leu Asp Gly Val
2115 2120 2125

Arg Leu His Arg Phe Ala Pro Pro Cys Lys Pro Leu Leu Arg Glu Glu
2130 2135 2140

Val Ser Phe Arg Val Gly Leu His Glu Tyr Pro Val Gly Ser Gln Leu
2145 2150 2155 2160

Pro Cys Glu Pro Glu Pro Asp Val Ala Val Leu Thr Ser Met Leu Thr
2165 2170 2175

Asp Pro Ser His Ile Thr Ala Glu Ala Ala Gly Arg Arg Leu Ala Arg
2180 2185 2190

Gly Ser Pro Pro Ser Val Ala Ser Ser Ser Ala Ser Gln Leu Ser Ala
2195 2200 2205

Pro Ser Leu Lys Ala Thr Cys Thr Ala Asn His Asp Ser Pro Asp Ala
2210 2215 2220

Glu Leu Ile Glu Ala Asn Leu Leu Trp Arg Gln Glu Met Gly Gly Asn
2225 2230 2235 2240

Ile Thr Arg Val Glu Ser Glu Asn Lys Val Val Ile Leu Asp Ser Phe
2245 2250 2255

Asp Pro Leu Val Ala Glu Glu Asp Glu Arg Glu Ile Ser Val Pro Ala
2260 2265 2270

Glu Ile Leu Arg Lys Ser Arg Arg Phe Ala Gln Ala Leu Pro Val Trp
2275 2280 2285

Ala Arg Pro Asp Tyr Asn Pro Pro Leu Val Glu Thr Trp Lys Lys Pro
2290 2295 2300

Asp Tyr Glu Pro Pro Val Val His Gly Cys Pro Leu Pro Pro Pro Lys
2305 2310 2315 2320

Ser Pro Pro Val Pro Pro Pro Arg Lys Lys Arg Thr Val Val Leu Thr
2325 2330 2335

Glu Ser Thr Leu Ser Thr Ala Leu Ala Glu Leu Ala Thr Arg Ser Phe
2340 2345 2350

Gly Ser Ser Ser Thr Ser Gly Ile Thr Gly Asp Asn Thr Thr Thr Ser
2355 2360 2365

Ser Glu Pro Ala Pro Ser Gly Cys Pro Pro Asp Ser Asp Ala Glu Ser
2370 2375 2380

Tyr Ser Ser Met Pro Pro Leu Glu Gly Glu Pro Gly Asp Pro Asp Leu
2385 2390 2395 2400

Ser Asp Gly Ser Trp Ser Thr Val Ser Ser Glu Ala Asn Ala Glu Asp
2405 2410 2415

Val Val Cys Cys Ser Met Ser Tyr Ser Trp Thr Gly Ala Leu Val Thr
2420 2425 2430

Pro Cys Ala Ala Glu Glu Gln Lys Leu Pro Ile Asn Ala Leu Ser Asn
2435 2440 2445

Ser Leu Leu Arg His His Asn Leu Val Tyr Ser Thr Thr Ser Arg Ser
2450 2455 2460

Ala Cys Gln Arg Gln Lys Lys Val Thr Phe Asp Arg Leu Gln Val Leu
2465 2470 2475 2480

Asp Ser His Tyr Gln Asp Val Leu Lys Glu Val Lys Ala Ala Ala Ser
2485 2490 2495

Lys Val Lys Ala Asn Leu Leu Ser Val Glu Glu Ala Cys Ser Leu Thr
2500 2505 2510

Pro Pro His Ser Ala Lys Ser Lys Phe Gly Tyr Gly Ala Lys Asp Val
2515 2520 2525

Arg Cys His Ala Arg Lys Ala Val Thr His Ile Asn Ser Val Trp Lys
2530 2535 2540

Asp Leu Leu Glu Asp Asn Val Thr Pro Ile Asp Thr Thr Ile Met Ala
2545 2550 2555 2560

Lys Asn Glu Val Phe Cys Val Gln Pro Glu Lys Gly Gly Arg Lys Pro
2565 2570 2575

Ala Arg Leu Ile Val Phe Pro Asp Leu Gly Val Arg Val Cys Glu Lys
2580 2585 2590

Met Ala Leu Tyr Asp Val Val Thr Lys Leu Pro Leu Ala Val Met Gly
2595 2600 2605

Ser Ser Tyr Gly Phe Gln Tyr Ser Pro Gly Gln Arg Val Glu Phe Leu
2610 2615 2620

Val Gln Ala Trp Lys Ser Lys Lys Thr Pro Met Gly Phe Ser Tyr Asp

-continued

```
2625                2630                2635                2640

Thr Arg Cys Phe Asp Ser Thr Val Thr Glu Ser Asp Ile Arg Thr Glu
                2645                2650                2655

Glu Ala Ile Tyr Gln Cys Cys Asp Leu Asp Pro Gln Ala Arg Val Ala
            2660                2665                2670

Ile Lys Ser Leu Thr Glu Arg Leu Tyr Val Gly Gly Pro Leu Thr Asn
        2675                2680                2685

Ser Arg Gly Glu Asn Cys Gly Tyr Arg Arg Cys Arg Ala Ser Gly Val
    2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
                2725                2730                2735

Gly Asp Asp Leu Val Val Ile Cys Glu Ser Ala Gly Val Gln Glu Asp
            2740                2745                2750

Ala Ala Ser Leu Arg Ala Phe Thr Glu Ala Met Thr Arg Tyr Ser Ala
        2755                2760                2765

Pro Pro Gly Asp Pro Pro Gln Pro Glu Tyr Asp Leu Glu Leu Ile Thr
    2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
                2805                2810                2815

Trp Glu Thr Ala Arg His Thr Pro Val Asn Ser Trp Leu Gly Asn Ile
            2820                2825                2830

Ile Met Phe Ala Pro Thr Leu Trp Ala Arg Met Ile Leu Met Thr His
        2835                2840                2845

Phe Phe Ser Val Leu Ile Ala Arg Asp Gln Leu Glu Gln Ala Leu Asp
    2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
                2885                2890                2895

Tyr Ser Pro Gly Glu Ile Asn Arg Val Ala Ala Cys Leu Arg Lys Leu
            2900                2905                2910

Gly Val Pro Pro Leu Arg Ala Trp Arg His Arg Ala Arg Ser Val Arg
        2915                2920                2925

Ala Arg Leu Leu Ala Arg Gly Gly Arg Ala Ala Ile Cys Gly Lys Tyr
    2930                2935                2940

Leu Phe Asn Trp Ala Val Arg Thr Lys Leu Lys Leu Thr Pro Ile Ala
2945                2950                2955                2960

Ala Ala Gly Gln Leu Asp Leu Ser Gly Trp Phe Thr Ala Gly Tyr Ser
                2965                2970                2975

Gly Gly Asp Ile Tyr His Ser Val Ser His Ala Arg Pro Arg Trp Ile
            2980                2985                2990

Trp Phe Cys Leu Leu Leu Leu Ala Ala Gly Val Gly Ile Tyr Leu Leu
        2995                3000                3005

Pro Asn Arg
    3010
```

( 2 ) INFORMATION FOR SEQ ID NO:37:

( i ) SEQUENCE CHARACTERISTICS:

( A ) LENGTH: 192 amino acids ( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:37:

```
Tyr Gln Val Arg Asn Ser Thr Gly Leu Tyr His Val Thr Asn Asp Cys
1               5                   10                  15

Pro Asn Ser Ser Ile Val Tyr Glu Ala Ala Asp Ala Ile Leu His Ala
            20                  25                  30

Pro Gly Cys Val Pro Cys Val Arg Glu Gly Asn Ala Ser Arg Cys Trp
        35                  40                  45

Val Ala Met Thr Pro Thr Val Ala Ala Arg Asp Gly Arg Leu Pro Thr
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Ile Phe Leu Val
                85                  90                  95

Gly Gln Leu Phe Thr Phe Ser Pro Arg Arg His Trp Thr Thr Gln Gly
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Thr Ala Leu Val Val Ala
    130                 135                 140

Gln Leu Leu Arg Ile Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Leu Phe Ala Gly Val Asp Ala
            180                 185                 190
```

( 2 ) INFORMATION FOR SEQ ID NO:38:

( i ) SEQUENCE CHARACTERISTICS:
( A ) LENGTH: 192 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:38:

```
Tyr Gln Val Arg Asn Ser Thr Gly Leu Tyr His Val Thr Asn Asp Cys
1               5                   10                  15

Pro Asn Ser Ser Ile Val Tyr Glu Ala Ala Asp Ala Ile Leu His Thr
            20                  25                  30

Pro Gly Cys Val Pro Cys Val Arg Glu Gly Asn Ala Ser Arg Cys Trp
        35                  40                  45

Val Ala Met Thr Pro Thr Val Ala Thr Arg Asp Gly Lys Leu Pro Ala
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Gly
            100                 105                 110

Cys Asn Cys Ser Ile Tyr Pro Gly His Ile Thr Gly His Arg Met Ala
        115                 120                 125
```

```
Trp Asp Met Met Met Asn Trp Ser Pro Thr Thr Ala Leu Val Met Ala
    130                 135                 140

Gln Leu Leu Arg Ile Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Leu Phe Ala Gly Val Asp Ala
            180                 185                 190
```

( 2 ) INFORMATION FOR SEQ ID NO:39:

( i ) SEQUENCE CHARACTERISTICS:
( A ) LENGTH: 192 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:39:

```
Tyr Glu Val Arg Asn Val Ser Gly Ile Tyr His Val Thr Asn Asp Cys
1               5                   10                  15

Ser Asn Ser Ser Ile Val Tyr Glu Ala Ala Asp Met Ile Met His Thr
            20                  25                  30

Pro Gly Cys Val Pro Cys Val Arg Glu Ser Asn Phe Ser Arg Cys Trp
        35                  40                  45

Val Ala Leu Thr Pro Thr Leu Ala Ala Arg Asn Ser Ser Ile Pro Thr
    50                  55                  60

Thr Thr Ile Arg Arg His Val Asp Leu Leu Val Gly Ala Ala Ala Leu
65                  70                  75                  80

Cys Ser Ala Met Tyr Val Gly Asp Leu Cys Gly Ser Val Phe Leu Val
                85                  90                  95

Ser Gln Leu Phe Thr Phe Ser Pro Arg Arg Tyr Glu Thr Val Gln Asp
            100                 105                 110

Cys Asn Cys Ser Ile Tyr Pro Gly His Val Ser Gly His Arg Met Ala
        115                 120                 125

Trp Asp Met Met Met Asn Trp Ser Pro Thr Thr Ala Leu Val Val Ser
    130                 135                 140

Gln Leu Leu Arg Ile Pro Gln Ala Val Val Asp Met Val Ala Gly Ala
145                 150                 155                 160

His Trp Gly Val Leu Ala Gly Leu Ala Tyr Tyr Ser Met Val Gly Asn
                165                 170                 175

Trp Ala Lys Val Leu Ile Val Met Leu Leu Phe Ala Gly Val Asp Gly
            180                 185                 190
```

( 2 ) INFORMATION FOR SEQ ID NO:40:

( i ) SEQUENCE CHARACTERISTICS:
( A ) LENGTH: 192 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:40:

```
His Gln Val Arg Asn Ser Thr Gly Leu Tyr His Val Thr Asn Asp Cys
1               5                   10                  15

Pro Asn Ser Ser Ile Val Tyr Glu Ala Ala Asp Ala Ile Leu His Thr
            20                  25                  30
```

-continued

```
Pro Gly Cys Val Pro Cys Val His Glu Gly Asn Val Ser Arg Cys Trp
        35                  40                  45

Val Ala Val Thr Pro Thr Val Ala Thr Arg Asp Gly Lys Leu Pro Thr
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Gly
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Ala Ala Leu Val Met Ala
    130                 135                 140

Gln Leu Leu Arg Ile Pro Gln Ala Ile Met Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Leu Phe Ala Gly Val Asp Ala
            180                 185                 190
```

( 2 ) INFORMATION FOR SEQ ID NO:41:

( i ) SEQUENCE CHARACTERISTICS:
( A ) LENGTH: 192 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:41:

```
Tyr Gln Val Arg Asn Ser Thr Gly Leu Tyr His Val Thr Asn Asp Cys
1               5                   10                  15

Pro Asn Ser Ser Ile Val Tyr Glu Ala His Asp Ala Ile Leu His Thr
            20                  25                  30

Pro Gly Cys Val Pro Cys Val Arg Glu Gly Asn Val Ser Arg Cys Trp
        35                  40                  45

Val Ala Met Thr Pro Thr Val Ala Thr Arg Asp Gly Lys Leu Pro Ala
    50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Ile
                85                  90                  95

Gly Gln Leu Phe Thr Phe Ser Pro Arg Arg His Trp Thr Thr Gln Gly
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Ala Ala Leu Val Met Ala
    130                 135                 140

Gln Leu Leu Arg Ile Pro Gln Ala Ile Leu Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Leu Phe Ala Gly Val Asp Ala
            180                 185                 190
```

-continued ( 2 ) INFORMATION FOR SEQ ID NO:42:

( i ) SEQUENCE CHARACTERISTICS:
( A ) LENGTH: 192 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:42:

Tyr Glu Val Arg Asn Val Ser Gly Ile Tyr His Val Thr Asn Asp Cys
1 5 10 15

Ser Asn Ser Ser Ile Val Tyr Glu Ala Ala Asp Met Ile Met His Thr
20 25 30

Pro Gly Cys Val Pro Cys Val Arg Glu Asp Asn Ser Ser Arg Cys Trp
35 40 45

Val Ala Leu Thr Pro Thr Leu Ala Ala Arg Asn Ala Ser Val Pro Thr
50 55 60

Thr Thr Ile Arg Arg His Val Asp Leu Leu Val Gly Ala Ala Ala Phe
65 70 75 80

Cys Ser Ala Met Tyr Val Gly Asp Leu Cys Gly Ser Val Phe Leu Val
85 90 95

Ser Gln Leu Phe Thr Phe Ser Pro Arg Arg His Glu Thr Val Gln Asp
100 105 110

Cys Asn Cys Ser Ile Tyr Pro Gly His Leu Ser Gly His Arg Met Ala
115 120 125

Trp Asp Met Met Met Asn Trp Ser Pro Thr Thr Ala Leu Val Val Ser
130 135 140

Gln Leu Leu Arg Ile Pro Gln Ala Val Val Asp Met Val Ala Gly Ala
145 150 155 160

His Trp Gly Val Leu Ala Gly Leu Ala Tyr Tyr Ser Met Val Gly Asn
165 170 175

Trp Ala Lys Val Leu Ile Val Ala Leu Leu Phe Ala Gly Val Asp Gly
180 185 190

( 2 ) INFORMATION FOR SEQ ID NO:43:

( i ) SEQUENCE CHARACTERISTICS:
( A ) LENGTH: 192 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:43:

Tyr Glu Val His Asn Val Ser Gly Ile Tyr His Val Thr Asn Asp Cys
1 5 10 15

Ser Asn Ala Ser Ile Val Tyr Glu Ala Ala Asp Leu Ile Met His Thr
20 25 30

Pro Gly Cys Val Pro Cys Val Arg Glu Gly Asn Ser Ser Arg Cys Trp
35 40 45

Val Ala Leu Thr Pro Thr Leu Ala Ala Arg Asn Val Thr Ile Pro Thr
50 55 60

Thr Thr Ile Arg Arg His Val Asp Leu Leu Val Gly Ala Ala Ala Phe
65 70 75 80

Cys Ser Ala Met Tyr Val Gly Asp Leu Cys Gly Ser Val Phe Leu Val
85 90 95

Ser Gln Leu Phe Thr Phe Ser Pro Arg Arg His Val Thr Leu Gln Asp 100 105 110

Cys Asn Cys Ser Ile Tyr Pro Gly His Val Ser Gly His Arg Met Ala
115 120 125

Trp Asp Met Met Met Asn Trp Ser Pro Thr Thr Ala Leu Val Val Ser
130 135 140

Gln Leu Leu Arg Ile Pro Gln Ala Val Val Asp Met Val Ala Gly Ala
145 150 155 160

His Trp Gly Val Leu Ala Gly Leu Ala Tyr Tyr Ser Met Ala Gly Asn
165 170 175

Trp Ala Lys Val Leu Ile Val Met Leu Leu Phe Ala Gly Val Asp Gly
180 185 190

( 2 ) INFORMATION FOR SEQ ID NO:44:

( i ) SEQUENCE CHARACTERISTICS:
( A ) LENGTH: 192 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:44:

Tyr Gln Val Arg Asn Ser Ser Gly Ile Tyr His Val Thr Asn Asp Cys
1 5 10 15

Pro Asn Ser Ser Ile Val Tyr Glu Thr Ala Asp Thr Ile Leu His Ser
20 25 30

Pro Gly Cys Val Pro Cys Val Arg Glu Gly Asn Ala Ser Lys Cys Trp
35 40 45

Val Pro Val Ala Pro Thr Val Ala Thr Arg Asp Gly Asn Leu Pro Ala
50 55 60

Thr Gln Leu Arg Arg His Ile Asp Leu Leu Val Gly Ser Ala Thr Leu
65 70 75 80

Cys Ser Ala Leu Tyr Val Gly Asp Leu Cys Gly Ser Val Phe Leu Val
85 90 95

Gly Gln Leu Phe Thr Phe Ser Pro Arg Arg His Trp Thr Thr Gln Asp
100 105 110

Cys Asn Cys Ser Ile Tyr Pro Gly His Ile Thr Gly His Arg Met Ala
115 120 125

Trp Asp Met Met Met Asn Trp Ser Pro Thr Ala Ala Leu Val Met Ala
130 135 140

Gln Leu Leu Arg Ile Pro Gln Ala Ile Leu Asp Met Ile Ala Gly Ala
145 150 155 160

His Trp Gly Val Leu Ala Gly Ile Ala Tyr Phe Ser Met Val Gly Asn
165 170 175

Trp Ala Lys Val Leu Val Val Leu Leu Leu Phe Ala Gly Val Asp Ala
180 185 190

( 2 ) INFORMATION FOR SEQ ID NO:45:

( i ) SEQUENCE CHARACTERISTICS:
( A ) LENGTH: 192 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:45:

Tyr Gln Val Arg Asn Ser Thr Gly Leu Tyr His Val Thr Asn Asp Cys

-continued

| 1 | | | | 5 | | | | | 10 | | | | | 15 | |
|---|---|---|---|---|---|---|---|---|---|---|---|---|---|---|---|
| Pro | Asn | Ser | Ser | Ile | Val | Tyr | Glu | Ala | Ala | Asp | Ala | Ile | Leu | His | Ala |
| | | | 20 | | | | | 25 | | | | | 30 | | |
| Pro | Gly | Cys | Val | Pro | Cys | Val | Arg | Glu | Asp | Asn | Val | Ser | Arg | Cys | Trp |
| | | 35 | | | | | 40 | | | | | 45 | | | |
| Val | Ala | Val | Thr | Pro | Thr | Val | Ala | Thr | Lys | Asp | Gly | Lys | Leu | Pro | Thr |
| | 50 | | | | | 55 | | | | | 60 | | | | |
| Thr | Gln | Leu | Arg | Arg | His | Ile | Asp | Leu | Leu | Val | Gly | Ser | Ala | Thr | Leu |
| 65 | | | | | 70 | | | | | 75 | | | | | 80 |
| Cys | Ser | Ala | Leu | Tyr | Val | Gly | Asp | Leu | Cys | Gly | Ser | Ile | Phe | Leu | Val |
| | | | | 85 | | | | | 90 | | | | | 95 | |
| Gly | Gln | Leu | Phe | Thr | Phe | Ser | Pro | Arg | Arg | His | Trp | Thr | Thr | Gln | Asp |
| | | | 100 | | | | | 105 | | | | | 110 | | |
| Cys | Asn | Cys | Ser | Ile | Tyr | Pro | Gly | His | Ile | Thr | Gly | His | Arg | Met | Ala |
| | | 115 | | | | | 120 | | | | | 125 | | | |
| Trp | Asp | Met | Met | Met | Asn | Trp | Ser | Pro | Thr | Ala | Ala | Leu | Val | Val | Ala |
| | 130 | | | | | 135 | | | | | 140 | | | | |
| Gln | Leu | Leu | Arg | Ile | Pro | Gln | Ala | Ile | Leu | Asp | Met | Ile | Ala | Gly | Ala |
| 145 | | | | | 150 | | | | | 155 | | | | | 160 |
| His | Trp | Gly | Val | Leu | Ala | Gly | Met | Ala | Tyr | Phe | Ser | Met | Val | Gly | Asn |
| | | | | 165 | | | | | 170 | | | | | 175 | |
| Trp | Ala | Lys | Val | Leu | Val | Val | Leu | Leu | Leu | Phe | Ala | Gly | Val | Asp | Ala |
| | | | 180 | | | | | 185 | | | | | 190 | | |

IMMUNOREACTIVE POLYPEPTIDE COMPOSITIONS

This application is a continuation of application Ser. No. 07/759,575, filed Sep. 13, 1991.

TECHNICAL FIELD

This invention relates generally to immunoreactive polypeptide compositions, methods of using the compositions in immunological applications, and materials and methods for making the compositions.

BACKGROUND

The hepatitis C virus has been recently identified as the major causative agent of post-transfusion Non-A, Non-B hepatitis (NANHB), as well as a significant cause of community-acquired NANBH. Materials and methods for obtaining the viral genomic sequences are known. See, e.g. PCT Publication Nos. W089/04669, W090/11089 & W090/14436.

Molecular characterization of the HCV genome indicates that it is a RNA molecule of positive polarity containing approximately 10,000 nucleotides that encodes a polyprotein of about 3011 amino acids. Several lines of evidence suggest that HCV has a similar genetic organization to the viruses of the family Flaviviridae, which includes the flavi- and pestivirus. Like its pesti- and flaviviral relatives, HCV appears to encode a large polyprotein precursor from which individual viral proteins (both structural and non-structural) are processed.

RNA-containing viruses can have relatively high rates of spontaneous mutation, i.e., reportedly on the order of $10^{-3}$ to $10^{-4}$ per incorporated nucleotide. Therefore, since heterogeneity and fluidity of genotype are common in RNA viruses, there may be multiple viral isolates, which may be virulent or avirulent, within the HCV species.

A number of different isolates of HCV have now been identified. The sequences of these isolates demonstrate the limited heterogeneity characteristic of RNA viruses.

Isolate HCV J1.1 is described in Kubo, Y. et al. (1989), Japan. Nucl. Acids Res. 17: 10367–10372; Takeuchi, K. et al.(1990), Gene 91: 287–291; Takeuchi et al. (1990), J. Gen. Virol. 71: 3027–3033; Takeuchi et al. (1990), Nucl. Acids Res. 18: 4626.

The complete coding sequences plus the 5'- and 3'-terminal sequences of two independent isolates, "HCV-J" and "BK", are described by Kato et al. and Takamizawa et al, respectively. (Kato et al. (1990), Proc. Natl. Acad. Sci. USA 87: 9524–9528; Takamizawa et al (1991), J. Virol. 65: 1105–1113.)

Other publications describing HCV isolates are the following;

"HCV-1": Choo et al (1990), Brit. Med. Bull. 46: 423–441; Choo et al. (1991), Proc. Natl. Acad. Sci. USA 88: 2451–2455; Han et al. (1991), Proc. Natl. Acad. Sci. USA 88: 1711–1715; European Patent Publication No. 318, 216.

"HC-J1" and "HC-J4": Okamoto et al. (1991), Japan J. Exp. Med. 60: 167–177.

"HCT 18", "HCT 23", "Th", "HCT 27", "EC1" and "EC10": Weiner et al. (1991), Virol. 180: 842–848.

"Pt-1", "HCV-K1" and "HCV-K2": Enomoto et al, There are two major types of hepatitis C virus in Japan. Division of Gastroenterology, Department of Internal Medicine, Kanazawa Medical University, Japan.

Clones "A", "C", "D" & "E": Tsukiyama-Kohara et al., A second group of hepatitis virus, in *Virus Genes*.

A typical approach to diagnostic and vaccine strategy is to focus on conserved viral domains. This approach, however, suffers from the disadvantage of ignoring important epitopes that may lie in variable domains.

It is an object of this invention to provide polypeptide compositions that are immunologically cross-reactive with multiple HCV isolates, particularly with respect to heterogeneous domains of the virus.

SUMMARY OF THE INVENTION

It has been discovered that a number of important HCV epitopes vary among viral isolates, and that these epitopes can be mapped to particular domains. This discovery allows for a strategy of producing immunologically cross-reactive polypeptide compositions that focuses on variable (rather than conserved) domains.

Accordingly, one embodiment of the present invention is an immunoreactive composition comprising polypeptides wherein the polypeptides comprise the amino acid sequence of an epitope within a first variable domain of HCV, and at least two heterogeneous amino acid sequences from the first variable domain of distinct HCV isolates are present in the composition.

Another embodiment of the invention is an immunoreactive composition comprising a plurality of antigen sets, wherein (a) each antigen set consists of a plurality of substantially identical polypeptides comprising the amino acid sequence of an epitope within a first variable domain of an HCV isolate, and (b) the amino acid sequence of the epitope of one set is heterogeneous with respect to the amino acid sequence of the analogous sequence of at least one other set.

Another embodiment of the invention is an immunoreactive composition comprising a plurality of polypeptides wherein each polypeptide has the formula $$R_r—(SV_n)_x—R'_{r'}$$

wherein

R and R' are amino acid sequences of about 1–2000 amino acids, and are the same or different;

r and r' are 0 or 1, and are the same or different;

V is an amino acid sequence comprising the sequence of an HCV variable domain, wherein the variable domain comprises at least one epitope;

S in an integer≧1, representing a selected variable domain; and n is an integer≧1, representing a selected HCV isolate heterogeneous at a given SV with respect to at least one other isolate having a different value for n, and n being independently selected for each x;

x is an integer≧1; and with the proviso that amino acid sequences are present in the composition representing a combination selected from the group consisting of (i) $1V_1$ and $1V_2$, (ii) $1V_1$ and $2V_2$, and (iii) $1V_1$ and $2V_1$.

Yet another embodiment of the invention is a method for preparing an immunogenic pharmaceutical composition HCV comprising:

(a) providing an immunoreactive composition as described above;

(b) providing a suitable excipient; and (c) mixing the immunoreactive composition of (a) with the excipient of (b) in a proportion that provides an immunogenic response upon administration to a mammal.

Still another embodiment of the invention is a method for producing anti-HCV antibodies comprising administering to a mammal an effective amount of an immunoreactive composition as described above.

Yet another embodiment of the invention is a method of detecting antibodies to HCV within a biological sample comprising:

(a) providing a biological sample suspected of containing antibodies to HCV;

(b) providing an immunoreactive composition described above;

(c) reacting the biological sample of (a) with the immunoreactive composition of (b) under conditions which allow the formation of antigen-antibody complexes; and (d) detecting the formation of antigen-antibody complexes formed between the immunoreactive composition of (a) and the antibodies of the biological sample of (b), if any.

Another embodiment of the invention is a kit for detecting antibodies to HCV within a biological sample comprising an immunoreactive composition as described above packaged in a suitable container.

BRIEF DESCRIPTION OF THE FIGURES

FIG. 2 shows a comparison of the deduced amino acid sequences of the E1 protein encoded by group I and group II HCV isolates.

FIG. 3 shows a comparison of the amino acid sequences of the putative E2/NS1 region of HCV isolates.

FIG. 8A shows the deduced amino acid sequences of isolates HCV J1.1 and J1.2 from amino acids 384 to 647. FIG. 8B shows the deduced amino acid sequences of isolates HCT27 and HCVE1 from amino acids 384 to 651.

FIG. 9 shows the entire polyprotein sequence of isolate HCV-1.

MODES OF PRACTICING THE INVENTION

The practice of the present invention will employ, unless otherwise indicated, conventional techniques of molecular biology, microbiology, recombinant DNA, and immunology, which are within the skill of the art. Such techniques are explained fully in the literature. See e.g., Maniatis, Fitsch & Sambrook, MOLECULAR CLONING; A LABORATORY MANUAL (2nd ed. 1989); DNA CLONING, VOLUMES I AND II (D. N Glover ed. 1985); OLIGONUCLEOTIDE SYNTHESIS (M. J. Gait ed, 1984); NUCLEIC ACID HYBRIDIZATION (B. D. Hames & S. J. Higgins eds. 1984); TRANSCRIPTION AND TRANSLATION (B. D. Hames & S. J. Higgins eds. 1984); ANIMAL CELL CULTURE (R. I. Freshney ed. 1986); IMMOBILIZED CELLS AND ENZYMES (IRL Press, 1986); B. Perbal, A PRACTICAL GUIDE TO MOLECULAR CLONING (1984); the series, METHODS IN ENZYMOLOGY (Academic Press, Inc.); GENE TRANSFER VECTORS FOR MAMMALIAN CELLS (J. H. Miller and M. P. Calos eds. 1987, Cold Spring Harbor Laboratory), Methods in Enzymology Vol. 154 and Vol. 155 (Wu and Grossman, and Wu, eds., respectively), Mayer and Walker, eds. (1987), IMMUNOCHEMICAL METHODS IN CELL AND MOLECULAR BIOLOGY (Academic Press, London), Scopes, (1987), PROTEIN PURIFICATION: PRINCIPLES AND PRACTICE, Second Edition (Springer-Verlag, N.Y.), and HANDBOOK OF EXPERIMENTAL IMMUNOLOGY, VOLUMES I–IV (D. M. Weir and C. C. Blackwell eds 1986); IMMUNOASSAY: A PRACTICAL GUIDE (D. W. Chan ed. 1987). All patents, patent applications, and publications mentioned herein, both above and below, are incorporated by reference herein.

Figure 1:
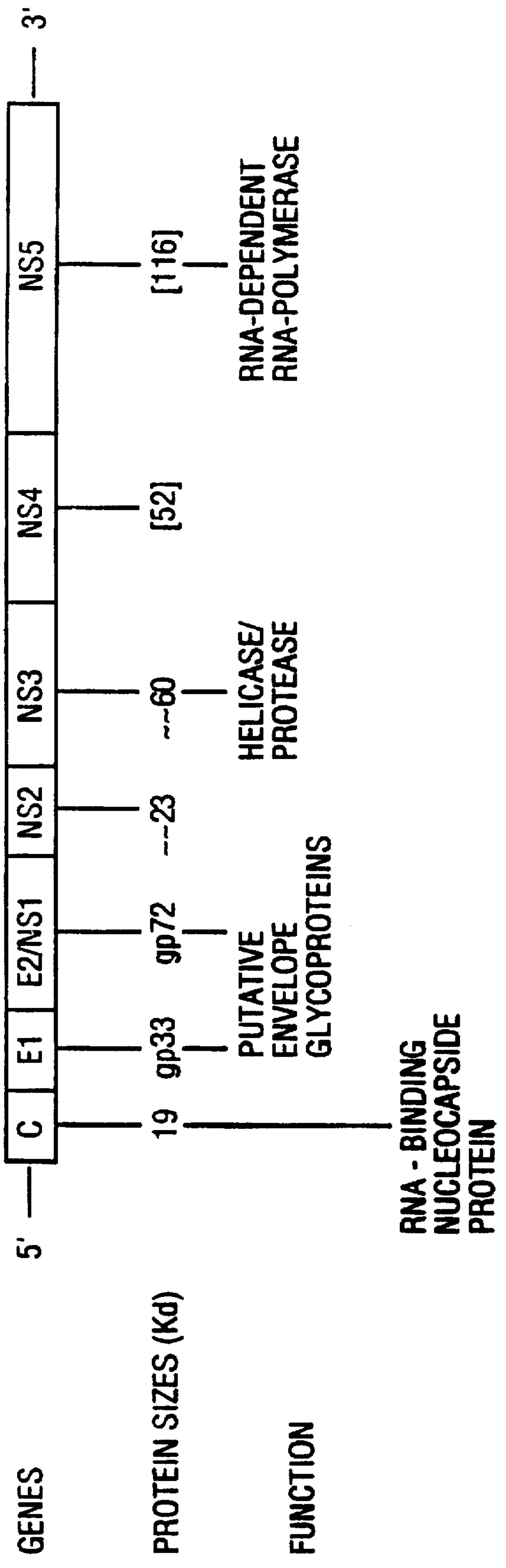
FIG. 1 schematically shows the genetic organization of the HCV genome.

HCV is a new member of the Family Flaviviridae which includes the pestiviruses (Hog Cholera Virus and Bovine Viral Diarrhea Virus) and the Flaviviruses, examples of which are Dengue and Yellow Fever Virus. A scheme of the genetic organization of HCV is shown in FIG. 1. Similar to the flavi- and pestiviruses, HCV appears to encode a basic polypeptide domain ("C") at the N-terminus of the viral polyprotein followed by two glycoprotein domains ("E1", "E2/NS1"), upstream of the nonstructural genes NS2 through NS5. The amino acid coordinates of the putative protein domains are shown in Table 1.

TABLE 1

The Putative Protein Domains in HCV

| a.a. coordinates (approximate) | Protein |
|---|---|
| 1–191 | C |
| 192–383 | E1 |
| 384–750 | E2/NS1 |
| 751–1006 | NS2 |
| 1007–1488 | NS3 |
| 1489–1959 | NS4 |
| 1960–3011 | NS5 |

As discussed above, a number of HCV isolates have been identified. Comparative sequence analysis of complete and partial HCV sequences indicates that based upon homology at the nucleotide and amino acid levels, HCV isolates can be broadly sub-divided into at least three basic groups (Table 2). See Houghton et al., (1991) Hepatology 14: 381–388. However, only partial sequence is available for the isolates in group III. Therefore, when the sequences of these isolates are more defined, one or more of these isolates may deserve separation into a different group, including a potential fourth group. Table 3 shows the sequence homologies between individual viral proteins of different HCV isolates as deduced from their nucleotide sequences. It can be seen that the proteins of the same virus group exhibit greater sequence similarity than the same proteins encoded by different virus groups (Table 3). One exception to this is the nucleocapsid protein that is highly conserved among all group I and II viral isolates sequences to date. (In Table 3, the symbol N/A signifies that the sequences were not available for comparison.) For purposes of the present invention, therefore, group I isolates can be defined as those isolates having their viral proteins, particularly E1 and E2/NS1 proteins, about 90% homologous or more at the amino acid level to the isolates classified as group I herein. Group II is defined in an analogous manner. Future groups can likewise be defined in terms of viral protein homology to a prototype isolate. Subgroups can also be defined by homology in limited proteins, such as the E1, E2/NS1 or NS2 proteins, or by simply higher levels of homology.

TABLE 2

Classification of hepatitis C viral genome RNA sequences into three basic groups.

| HCV I | HCV II | HCV III |
|---|---|---|
| HCV-1 | HCV-J1.1 | Clones A, C, D & E |
| HC-J1 | HC-J4 | HCV-K2 (a & b) |
| HCT 18 | HCV-J | |
| HCT 23 | BK | |
| Th | HCV-K1 | |
| HCT 27 | | |
| EC1 | | |
| Pt-1 | | |

The putative HCV envelope glycoprotein E2/NS1 may correspond to the gp53(BVDV)/gp55 (Hog Cholera Virus) envelope polypeptide of the pestiviruses and the NS1 of the flaviviruses, both of which confer protective immunity in hosts vaccinated with these polypeptides.

Striking similarities between the hypervariable region ("HV") and HIV-1 gp120V3 domains with respect to degree of sequence variation, the predictive effect of amino acid changes on putative antibody binding in addition to the lack of defined secondary structure suggest that the HV domain encodes neutralizing antibodies.

The immunogenicity of the domain is shown by antibody epitope mapping experiments, described in the Examples. The results of these studies suggest that in addition to the three major groups of HCV, HV specific sub-groups also exist.

Analysis of biological samples from individuals with HCV induced NANBH indicate that individuals may be carrying two or more HCV variants simultaneously. Two co-existing HV variants were found in the plasma of one individual, J1. In addition, partial sequencing of the gene of an individual with chronic NANBH, who had intermittent flares of hepatitis, revealed that the individual, Q, was infected with two HCV variants (Q1 or Q3). Each variant was associated with only one episode of the disease. An ELISA using a Q1 or Q3 specific peptide (amino acids 396–407) showed that Q developed an antibody response to the Q1 peptide but not the corresponding Q3 peptide, suggesting that Q's recrudescence of disease was due to the appearance of an HV variant. The presence of antibodies to the Q1 peptide but lack of humoral immune response to the Q3 peptide during the second episode of disease suggest that variation in the HV domain may result from the pressure of immune selection. Amino acids 396–407 appear to be subject to the greatest selective pressure in the HV domain. These findings support the thesis that high levels of chronicity associated with the disease might be due to an inadequate immunological host response to HCV infection and/or effective viral mechanisms of immunological evasion. Moreover, they point to the E2/NS1 HV region as a genetic region involved in a viral escape mechanism and/or an inadequate immunological response mechanism(s).

As discussed above, there are several variant regions within the HCV genome. One or more of these regions are most likely involved in a viral escape mechanism and/or an inadequate immunological response mechanism. Therefore, it is desirable to include in compositions for treatment of HCV polypeptides which would induce an immunogenic response to these variants.

TABLE 3

Amino Acid Homologies (%) Between Viral Proteins Encoded by Different HCV Isolates

| HCV Group | C | E1 | E2/NS1 | NS2 | NS3 | NS4 | NS5 |
|---|---|---|---|---|---|---|---|
| I compared to | | | | | | | |
| I | 98–100 | 94–100 | N/A | N/A | N/A | N/A | 99–100 |
| II | 97–98 | 77–79 | 78–81 | 75–77 | 91–92 | 90–93 | 84–88 |
| III | N/A | N/A | N/A | N/A | 86 | 76–80 | 71–74 |
| II compared to | | | | | | | |
| II | 98–100 | 92–100 | 89–100 | 93–100 | 94–100 | 97–100 | 95–100 |
| III | N/A | N/A | N/A | N/A | 84 | 76 | 74–75 |
| III compared to | | | | | | | |
| III | N/A | N/A | N/A | N/A | N/A | 91–100 | 89–100 |

It is noteworthy that the putative viral envelope proteins encoded by the E1 and E2/NS1 genes show substantial amino acid sequence variation between groups I and II. Only NS2 exhibits a greater degree of heterogeneity, while the C, NS3, NS4 and NS5 proteins all show greater sequence conservation between groups. The sequence variation observed in the putative virion envelope proteins between groups I and II reflects a characteristic segregation of amino acids between the two groups. An example of this is shown in FIG. 2 where the sequence of the E1 gene product is compared between viruses of groups I and II. The E1 amino acid sequences deduced from nucleotide sequences of HCV groups II and II are shown. In the figure, the horizontal bars indicate sequence identity with HCV-1. The asterisks indicate group-specific segregation of amino acids; the group-specific residues can be clearly identified. Group I sequences are HCV-1, HCT18, HCT23, HCT27, and HC-J1. Group II sequences are HC-J4, HCV-J, HCV J1.1, and BK. Such group-specific segregation of amino acids is also present in other gene products including gp72 encoded by the E2/NS1 gene. FIG. 3 shows the comparative amino acid sequence of the putative E2/NS1 region of HCV isolates which segregate as group I and group II. The latter protein also contains an N-terminal hypervariable region ("HV") of about 30 amino acids that shows large variation between nearly all isolates. See Weiner et al. (1991), supra. This region occurs between amino acids 384 to 414, using the amino acid numbering system of HCV-1.

In that the E1 and E2/NS1 regions of the genome encode putative envelope type polypeptides, these regions would be of particular interest with respect to immunogenicity. Thus, these regions are amongst those to which it would be particularly desirable to induce and/or increase an immune response to protect an individual against HCV infection, and to aid in the prevention of chronic recurrence of the disease in infected individuals. In addition, these regions would be amongst those from which it would be desirable to detect HCV variants which are arising during the course of infection, as well as super- or co-infection by two or more variants.

The present invention describes compositions and methods for treating individuals to prevent HCV infections, and particularly chronic HCV infections. In addition, it describes compositions and methods for detecting the presence of anti-HCV antibodies in biological samples. This latter method is particularly useful in identifying anti-HCV antibodies generated in response to immunologically distinct HCV epitopes. This method can also be used to study the evolution of multiple variants of HCV within an infected individual. In the discussion of the invention, the following definitions are applicable.

The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, etc.), polypeptides with substituted linkages, as well as other modifications known in the art, both naturally occurring and non-naturally occurring.

As used herein, A is "substantially isolated" from B when the weight of A is at least about 70%, more preferably at least about 80%, and most preferably at least about 90% of the combined weights of A and B. The polypeptide compositions of the present invention are preferably substantially free of human or other primate tissue (including blood, serum, cell lysate, cell organelles, cellular proteins, etc.) and cell culture medium.

A "recombinant polynucleotide" intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g. metals, radioactive metals, etc.), those containing alkylators, those with modified linkages (e.g., alpha anomeric nucleic acids, etc.), as well as unmodified forms of the polynucleotide.

"Recombinant host cells", "host cells", "cells", "cell lines", "cell cultures", and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

A "replicon" is any genetic element, e.g., a plasmid, a chromosome, a virus, a cosmid, etc., that behaves as an autonomous unit of polynucleotide replication within a cell; i.e., capable of replication under its own control.

A "vector" is a replicon further comprising sequences providing replication and/or expression of the open reading frame.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term "control sequences" is intended to include, at a minimum, all components whose presence is necessary for expression, and may also include additional components whose presence is advantageous, for example, leader sequences which govern secretion.

A "promoter" is a nucleotide sequence which is comprised of consensus sequences which allow the binding of RNA polymerase to the DNA template in a manner such that mRNA production initiates at the normal transcription initiation site for the adjacent structural gene.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, DNA (including cDNA), and recombinant polynucleotide sequences.

As used herein, "epitope" or "antigenic determinant" means an amino acid sequence that is immunoreactive. Generally an epitope consists of at least 3 to 5 amino acids, and more usually, consists of at least about 8, or even about 10 amino acids. As used herein, an epitope of a designated polypeptide denotes epitopes with the same amino acid sequence as the epitope in the designated polypeptide, and immunologic equivalents thereof.

An "antigen" is a polypeptide containing one or more epitopes.

"Immunogenic" means the ability to elicit a cellular and/or humoral immune response. An immunogenic response may be elicited by immunoreactive polypeptides alone, or may require the presence of a carrier in the presence or absence of an adjuvant.

"Immunoreactive" refers to (1) the ability to bind immunologically to an antibody and/or to a lymphocyte antigen receptor or (2) the ability to be immunogenic.

An "antibody" is any immunoglobulin, including antibodies and fragments thereof, that binds a specific epitope. The term encompasses, inter alia, polyclonal, monoclonal, and chimeric antibodies. Examples of chimeric antibodies are discussed in U.S. Pat. Nos. 4,816,397 and 4,816,567.

An "antigen set" is defined as a composition consisting of a plurality of substantially identical polypeptides, wherein the polypeptides are comprised of an amino acid sequence of one defined epitope.

"Substantially identical polypeptides" means polypeptides that are identical with the exception of variation limited to the typical range of sequence or size variation attributable to the polypeptide's method of production; e.g., recombinant expression, chemical synthesis, tissue culture, etc. This variation does not alter the desired functional property of a composition of substantially identical polypeptides; e.g., the composition behaves immunologically as a composition of identical polypeptides. The variations may be due to, for example, alterations resulting from the secretory process during transport of the polypeptide, less than 100% efficiency in chemical synthesis, etc.

Figure 9R:
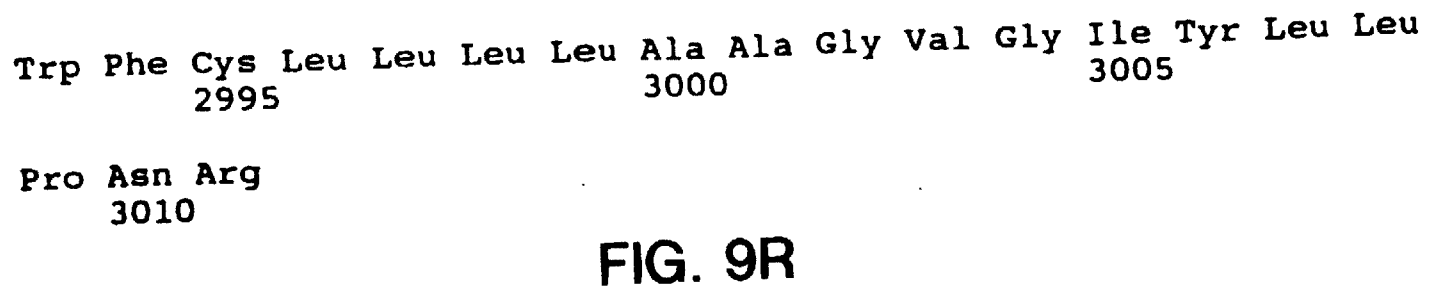

As used herein, a "variable domain" or "VD" of a viral protein is a domain that demonstrates a consistent pattern of amino acid variation between at least two HCV isolates or subpopulations. Preferably, the domain contains at least one epitope. Variable domains can vary from isolate to isolate by as little as 1 amino acid change. These isolates can be from the same or different HCV group(s) or subgroup(s). Variable domains can be readily identified through sequence composition among isolates, and examples of these techniques are described below. For the purposes of describing the present invention, variable domains will be defined with respect to the amino acid number of the polyprotein encoded by the genome of HCV-1 as shown in FIG. 9, with the initiator methionine being designated position 1. The corresponding variable domain in another HCV isolate is determined by aligning the two isolates sequences in a manner the brings the conserved domains outside any variable domain into maximum alignment. This can be performed with any of a number of computer software packages, such as ALIGN 1.0, available from the University of Virginia, Department of Biochemistry (Attn: Dr. William R. Pearson). See Pearson et al., (1988) Proc. Natl. Acad. Sci. USA 85: 2444–2448. It is to be understood that the amino acid numbers given for a particular variable domain are somewhat subjective and a matter of choice. Thus, the beginning and end of variable domains should be understood to be approximate and to include overlapping domains or subdomains, unless otherwise indicated.

An epitope is the "immunologic equivalent" of another epitope in a designated polypeptide when it cross-reacts with antibodies which bind immunologically to the epitope in the designated polypeptide.

Epitopes typically are mapped to comprise at least about five amino acids, sometimes at least about 8 amino acids, and even about 10 or more amino acids.

The amino acid sequence comprising the HCV epitope may be linked to another polypeptide (e.g., a carrier protein), either by covalent attachment or by expressing a fused polynucleotide to form a fusion protein. If desired, one may insert or attach multiple repeats of the epitope, and/or incorporate a variety of epitopes. The carrier protein may be derived from any source, but will generally be a relatively large, immunogenic protein such as BSA, KLH, or the like. If desired, one may employ a substantially full-length HCV protein as the carrier, multiplying the number of immunogenic epitopes. Alternatively, the amino acid sequence from the HCV epitope may be linked at the amino terminus and/or carboxy terminus to a non-HCV amino acid sequence, thus the polypeptide would be a "fusion polypeptide". Analogous types of polypeptides may be constructed using epitopes from other designated viral proteins.

A "variant" of a designated polypeptide refers to a polypeptide in which the amino acid sequence of the designated polypeptide has been altered by the deletion, substitution, addition or rearrangement of one or more amino acids in the sequence. Methods by which variants occur (for example, by recombination) or are made (for example, by site directed mutagenesis) are known in the art.

"Transformation" refers to the insertion of an exogenous polynucleotide into a host cell, irrespective of the method used for the insertion, for example, direct uptake, transduction (including viral infection), f-mating or electroporation. The exogenous polynucleotide may be maintained as a non-integrated vector, for example, a plasmid or viral genome, or alternatively, may be integrated into the host genome.

An "individual" refers to a vertebrate, particularly a member of a mammalian species, and includes but is not limited to rodents (e.g., mice, rats, hamsters, guinea pigs), rabbits, goats, pigs, cattle, sheep, and primates (e.g., chimpanzees, African Green Monkeys, baboons, orangutans, and humans).

As used herein, "treatment" refers to any of (i) the prevention of infection or reinfection, as in a traditional vaccine, (ii) the reduction or elimination of symptoms, and (iii) the substantial or complete elimination of the virus. Treatment may be effected prophylactically (prior to infection) or therapeutically (following infection).

The term "effective amount" refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment, as defined above. The exact amount necessary will vary from application. For vaccine applications or in the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation.

As used herein, a "biological sample" refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumors, organs, biopsies and also samples of in vitro cell culture constituents (including but not limited to conditioned medium resulting from the growth of cells in cell culture medium, e.g., Mab producing myeloma cells, recombinant cells, and cell components).

The immunoreactive polypeptide compositions of the present invention comprise a mixture of isolate- or group-specific epitopes from at least one HCV VD. Thus, there will be present at least two heterogeneous amino acid sequences each defining an epitope found in distinct HCV isolates located in the same or substantially same physical location in an HCV protein; i.e. each sequence maps to the same location within the HCV genome/polypeptide. Since the sequences are heterogeneous, the location is referred to as a variable domain (VD).

To better understand the invention, first the individual amino acid sequences that make up the compositions of the invention will be explained. Then the plurality of such sequences which are found in the compositions of the present invention will be discussed.

The amino acid sequence that characterizes the polypeptides of the present invention have a basic structure as follows:

$$L_y—Z—L'_{y'} \quad (I)$$

Z represents the amino acid sequence from a region of a protein from a selected HCV isolate, where the region comprises at least one variable domain and the variable domain comprises at least one epitope. L and L' are non-HCV amino acid sequences or HCV amino acid sequences that do not contain a variable domain, and which can be the same or different. y and y' are 0 or 1 and can be the same or different. Thus, formula I represents an amino acid sequence comprising the sequence of an HCV VD, wherein the VD comprises an epitope.

As discussed above, the epitope(s) in Z will usually comprise a minimum of about 5 amino acids, more typically a minimum of about 8 amino acids, and even more typically a minimum of about 10 amino acids.

The variable domain of Z can comprise more than one epitope. The variable domain of Z is at least as big as the combined sequences of the epitopes present, thus making it typically a minimum of about 5 amino acids when a single epitope is present. Since epitopes can overlap, the minimum amino acid sequence for combined epitopes in the variable domain may be less than the sum of the individual epitopes' sequences.

Z is the amino acid sequence of an HCV isolate comprising the above-described VD. Thus, the minimum size of Z is the minimum size of the VD. Z can comprise more HCV amino acid sequence than just the VD, and can further comprise more than one VD. The maximum size of Z is not critical, but obviously cannot exceed the length of the entire HCV polyprotein. Typically, however, Z will be the sequence of an entire HCV protein (particularly E1, E2/NS1, NS2, NS3, NS4 and NS5) or, even more typically, a fragment of such an HCV protein. Thus, Z will preferably range from a minimum of about 5 amino acids (more preferably about 8 or about 10 amino acids minimum) to a maximum of about 1100 amino acids (more preferably a maximum of about 500, more preferably a maximum of about 400 or even more preferably a maximum of about 200 amino acids maximum). More usually, the polypeptide of formula I and/or Z, when prepared by, e.g., chemical synthesis, is a maximum of about 50 amino acids, more typically a maximum of about 40 amino acids, and even more typically a maximum of about 30 amino acids.

The non-HCV amino acid sequences, L and L', if present, can constitute any of a number types of such sequences. For example, L and L' can represent non-HCV sequences to which Z is fused to facilitate recombinant expression (e.g., beta-galactosidase, superoxide dismutase, invertase, alpha-factor, TPA leader, etc.), as discussed below. Alternatively, L and L' can represent epitopes of other pathogens, such as hepatitis B virus, Bordetella pertussis, tetanus toxoid, diphtheria, etc., to provide compositions that are immunoreactive relative to a number these other pathogens. L and L' can be amino acid sequences that facilitate attachment to solid supports during peptide synthesis, immunoassay supports, vaccine carrier proteins, etc. In fact, L and L' can even comprise one or more superfluous amino acids with no functional advantage. There is no critical maximum size for L or L', the length being generally governed by the desired function. Typically, L and L' will each be a maximum of about 2000 amino acids, more typically a maximum of about 1000 amino acids. The majority of L and L' sequences with useful properties will be a maximum of about 500 amino acids. It is desirable, of course, to select L and L' so as to not block the immunoreactivity of Z.

The composition of polypeptides provided according to the present invention are characterized by the presence (in an effective amount for immunoreactivity) within the composition of at least two amino acid sequences defined as follows by formulas II and III, respectively:

$$L_y—Z_1—L'_{y'} \quad (II)$$

$$L_y—Z_2—L'_{y'} \quad (III)$$

L, L', y and y' are defined as above, as well as independently defined for each of formulas II and III. $Z_1$ and $Z_2$ are each HCV amino acid sequences as defined for Z above encompassing the same variable domain (i.e., physical location), but derived from different HCV isolates having between them at least one heterogeneous epitope in the common variable domain of $Z_1$ and $Z_2$. As an illustrative example, an amino acid sequence according to formula II could have as $Z_1$ a fragment the hypervariable domain spanning amino acids 384–414 of isolate HCV-1 (or more particularly 396–407 or 396–408), while $Z_2$ is the analogous fragment from isolate HCV-J1.1. These two isolates are heterogeneous in this domain, the amino acid sequences of the epitopes varying significantly.

It is to be understood that the compositions of the present invention may comprise more than just two discrete amino acid sequences according to formula I, and that the Z sequences may be divided into groups encompassing different variable domains. For example, a composition according to the present invention could comprise a group of HCV sequences (with amino acid sequences according to formula I) encompassing the hypervariable domain at amino acids 384–411 from isolates HCV-1, HCV-J1.1, HC-J1, HC-J4, etc. The composition could also comprise an additional group of HCV sequences (within amino acid sequences according to formula I) encompassing the variable domain at amino acids 215–255 also from isolates HCV-1, HCV-J1.1, HC-J1, HC-J4, etc. Within the context of the compositions of the present invention, therefore, the sequence of formula I can be further defined as follows:

$$SV_n \quad (IV)$$

V represents an amino acid sequence comprising the sequence of an HCV variable domain, wherein the variable domain comprises at least one epitope; i.e., formula I. S and n are integers of 1 or greater. S represents a particular variable domain, and n represents a particular isolate. For example, S=1 could represent the variable domain at amino acids 384–411; S=2 could represent the variable domain at amino acids 215–255; and n=1, 2, 3 and 4 could represent isolates HCV-1, HCV-J1.1, HC-J1 and HC-J4, respectively. Thus, the two groups of sequences discussed above could be represented by:

$1V_1$, $1V_2$, $1V_3$ & $1V_4$ Group 1

$2V_1$, $2V_2$, $2V_3$ & $2V_4$ Group 2

There are at least two distinct sequences of formula IV in the compositions according to the present invention; i.e., the composition contains two different sequences according to formula IV where the values for S and or n are different. For example, at least $1V_1$ and $1V_2$ are present, or at least $1V_1$ and $2V_2$ are present, or at least $1V_1$ and $2V_1$ are present.

The distinct sequences falling within formula IV are present in the composition either on the same or different polypeptide molecules. Using the minimum combination of $1V_1$ and $1V_2$ to illustrate, these two sequences could be present in the same polypeptide molecule (e.g., $1V_1$–$1V_2$) or in separate molecules. This feature of the compositions of the present invention can be described as compositions of polypeptides as follows:

$$R_r—(SV_n)_x—R'_{r'} \qquad (V)$$

wherein S, V and n are as defined above; R and R' are amino acid sequences of about 1–2000 amino acids, and are the same or different; r and r' are 0 or 1, and are the same or different; x is an integer≧1; n is independently selected for each x; and with the proviso that amino acid sequences are present in the composition representing a combination selected from the group consisting of (i) $1V_1$ and $1V_2$, (ii) $1V_1$ and $2V_2$, and (iii) $1V_1$ and $2V_1$. In embodiments where the distinct sequences of formula IV are in different polypeptides, x can be 1, although it can still be >1 if desired; e.g., a mixture of polypeptides $1V_1$–$V_2$ and $1V_1$–$2V_2$. When x is 1, r and r' are preferably both 0 to avoid redundancy with $L_y$ and $L'_y$, since V can be described by in a preferred embodiment by formula I. When x is >1, the combined lengths of R and the adjacent L, and of R' and the adjacent L', are preferably no more than the typical maximum lengths described above for L and L'.

The selection of the HCV amino acid sequences included within the distinct V sequences of the compositions will depend upon the intended application of the sequences and is within the skill of the art in view of the present disclosure. First, it should be appreciated that the HCV epitopes of concern to the present invention can be broken down into two types. The first type of epitopes are those that are "group-specific"; i.e., the corresponding epitopes in all or substantially all isolates within an HCV isolate group are immunologically cross-reactive with each other, but not with the corresponding epitopes of substantially all the isolates of another group. Preferably, the epitopes in a group-specific class are substantially conserved within the group, but not between or among the groups. The second type of epitopes are those that are "isolate-specific"; i.e., the epitope is immunologically cross-reactive with substantially identical isolates, and is not cross-reactive with all or substantially all distinct isolates.

These group- and isolate-specific epitopes can be readily identified in view of the present disclosure. First, the sequences of several HCV isolates is compared, as described herein, and areas of sequence heterogeneity identified. The pattern of heterogeneity usually indicates group or isolate specificity. If an identified area is known to comprise one or more epitopes, then a sequence of sufficient size to include the desired epitope(s) is selected to as an variable domain that may be included in the compositions of the present invention. If the immunoreactivity of a given heterogeneous area is not known, peptides representing the sequences found in that area of the various HCV isolates can be prepared and screened. Screening can include, but is not limited too, immunoassays with various sources of anti-HCV antibody (e.g., patient serum, neutralizing Mabs, etc.) or generation of antibody and testing the ability of such antibody to neutralize virus in vitro. Alternatively, the loci of epitopes identified in a screening protocol, such as that described below, can be examined for heterogeneity among various isolates and the immunological properties of corresponding heterogeneous sequences screened.

For vaccine applications, it is believed that variable domains from the E1 and/or E2/NS1 domains will be of particular interest. In particular, an E1 variable domain within amino acids 215–255 (see FIG. 2), and an E2/NS1 variable domain within amino acids 384–414 (see FIG. 3), have been identified as being important immunoreactive domains. The preliminary evidence suggests that one or both of these domains may be loci of heterogeneity responsible for escape mutants, leading to chronic HCV infections. Thus, polypeptide compositions as described above where the variable domain(s) in V are one or both of these variable domains are particularly preferred. Furthermore, the polypeptide compositions of the present invention, while particularly concerned with the generally linear epitopes in the variable domains, may also include conformational epitopes. For example, the composition can be comprised of a mixture of recombinant E1 and/or E2/NS1 proteins (exhibiting the variable domains of different isolates) expressed in a recombinant system (e.g., insect or mammalian cells) that maintains conformational epitopes either inside or outside the variable domain. Alternatively, an E1 and/or E2/NS1 subunit antigen from a single isolate that maintains conformational epitopes can be combined with a polypeptide composition according to the present invention (e.g., a mixture of synthetic polypeptides or denatured recombinant polypeptides). In another preferred application for vaccines, the polypeptide compositions described herein are combined with other HCV subunit antigens, such as those described in commonly owned U.S. Ser. No. 07/758,880, entitled "Hepatitis C Virus Asialoglycoproteins" (Attorney Docket No. 0154.002) by Robert O. Ralston, Frank Marcus, Kent B. Thudium, Barbara Gervase, and John Hall, filed on even date herewith, and incorporated herein by reference.

For diagnostic application, it may be useful to employ the compositions of the present invention as antigens, thereby improving the ability to detect antibody to distinct HCV isolates. Typically the polypeptide mixtures can be used directly in a homogeneous or heterogeneous immunoassay format, the latter preferably comprising immobilizing the polypeptide on a solid substrate (e.g., microtiter plate wells, plastic beads, nitrocellulose, etc.). See, e.g., PCT Pub. No. W090/11089; EPO Pub. No. 360,088; IMMUNOASSAY: A PRACTICAL GUIDE, supra. Alternatively, each substantially identical polypeptide that makes up the polypeptide composition of the present invention could be immobilized on the same support at discrete loci, thereby providing information as to which isolate or group the antibody has been generated. This may be particularly important in diagnostics if various isolates cause hepatitis, cancer or other diseases with different clinical prognoses. A preferred format is the Chiron RIBA™ strip immunoassay format, described in commonly owned U.S. Ser. No. 07/138,894 and U.S. Ser. No. 07/456,637, the disclosures of which are incorporated herein by reference.

Polypeptides useful in the manufacture of the compositions of the present invention can be made recombinantly, synthetically or in tissue culture. Recombinant polypeptides comprised of the truncated HCV sequences or full-length HCV proteins can be made up entirely of HCV sequences (one or more epitopes, either contiguous or noncontiguous), or sequences in a fusion protein. In fusion proteins, useful heterologous sequences include sequences that provide for secretion from a recombinant host, enhance the immunological reactivity of the HCV epitope(s), or facilitate the coupling of the polypeptide to a support or a vaccine carrier. See, e.g., EPO Pub. No. 116,201; U.S. Pat. No. 4,722,840; EPO Pub. No. 259,149; U.S. Pat. No. 4,629,783, the disclosures of which are incorporated herein by reference.

Full length as well as polypeptides comprised of truncated HCV sequences, and mutants thereof, may be prepared by chemical synthesis. Methods of preparing polypeptides by chemical synthesis are known in the art. They may also be prepared by recombinant technology. A DNA sequence encoding HCV-1, as well as DNA sequences of variable regions from other HCV isolates have been described and/or referenced herein. The availability of these sequences permits the construction of polynucleotides encoding immunoreactive regions of HCV polypeptides.

Polynucleotides encoding the desired polypeptide comprised of one or more of the immunoreactive HCV epitope from a variable domain of HCV may be chemically synthesized or isolated, and inserted into an expression vector. The vectors may or may not contain portions of fusion sequences such as beta-Galactosidase or superoxide dismutase (SOD). Methods and vectors which are useful for the production of polypeptides which contain fusion sequences of SOD are described in European Patent Office Publication number 0196056, published Oct. 1, 1986.

The DNA encoding the desired polypeptide, whether in fused or mature form and whether or not containing a signal sequence to permit secretion, may be ligated into expression vectors suitable for any convenient host. The hosts are then transformed with the expression vector. Both eukaryotic and prokaryotic host systems are presently used in forming recombinant polypeptides, and a summary of some of the more common control systems and host cell lines is presented infra. The host cells are incubated under conditions which allow expression of the desired polypeptide. The polypeptide is then isolated from lysed cells or from the culture medium and purified to the extent needed for its intended use.

The general techniques used in extracting the HCV genome from a virus, preparing and probing DNA libraries, sequencing clones, constructing expression vectors, transforming cells, performing immunological assays such as radioimmunoassays and ELISA assays, for growing cells in culture, and the like, are known in the art. (See, e.g., the references cited in the "Background" section, above, as well as the references cited at the beginning of this ("Modes of Practicing the Invention") section above.

Transformation of the vector containing the desired sequence into the appropriate host may be by any known method for introducing polynucleotides into a host cell, including, for example, packaging the polynucleotide in a virus and transducing the host cell with the virus, or by direct uptake of the polynucleotide. The transformation procedure used depends upon the host to be transformed. Bacterial transformation by direct uptake generally employs treatment with calcium or rubidium chloride (Cohen (1972), Proc. Natl. Acad. Sci. USA 69: 2110. Yeast transformation by direct uptake may be carried out using the method of Hinnen et al. (1978), J. Adv. Enzyme Reg. 7: 1929. Mammalian transformations by direct uptake may be conducted using the calcium phosphate precipitation method of Graham and Van der Eb (1978), Virology 52: 546, or the various known modifications thereof. Other methods for the introduction of recombinant polynucleotides into cells, particularly into mammalian cells, which are known in the art include dextran mediated transfection, calcium phosphate mediated transfection, polybrene mediated transfection, protoplast fusion, electroporation, encapsulation of the polynucleotide (s) in liposomes, and direct microinjection of the polynucleotides into nuclei.

In order to obtain expression of desired coding sequences, host cells are transformed with polynucleotides (which may be expression vectors), which are comprised of control sequences operably linked to the desired coding sequences. The control sequences are compatible with the designated host. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. Promoter sequences may be naturally occurring, for example, the β-lactamase (penicillinase) (Weissman (1981), "The cloning of interferon and other mistakes" in *Interferon* 3 (ed. I. Gresser), lactose (lac) (Chang et al. (1977), Nature 198: 1056) and tryptophan (trp) (Goeddel et al. (1980), Nucl. Acids Res. 8: 4057), and lambda-derived $P_L$ promoter system and N gene ribosome binding site (Shimatake et al. (1981), Nature 292: 128). In addition, synthetic promoters which do not occur in nature also function as bacterial promoters. For example, transcription activation sequences of one promoter may be joined with the operon sequences of another promoter, creating a synthetic hybrid promoter (e.g., the tac promoter, which is derived from sequences of the trp and lac promoters (De Boer et al. (1983), Proc. Natl. Acad. Sci. USA 80:21). The foregoing systems are particularly compatible with *E. coli;* if desired, other prokaryotic hosts such as strains of Bacillus or Pseudomonas may be used, with corresponding control sequences.

Eukaryotic hosts include yeast and mammalian cells in culture systems. *Saccharomyces cerevisiae* and *Saccharomyces carlsbergensis* are the most commonly used yeast hosts, and are convenient fungal hosts. Yeast compatible vectors generally carry markers which permit selection of successful transformants by conferring prototropy to auxotrophic mutants or resistance to heavy metals on wild-type strains. Yeast compatible vectors may employ the 2 micron origin of replication (Broach et al. (1983), Meth. Enz. 101: 307), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes (Hess et al. (1968), J. Adv. Enzyme Reg. 7: 149); for example, alcohol dehydrogenase (ADH) (E.P.O. Publication No. 284044), enolase, glucokinase, glucose-6-phosphate isomerase, glyceraldehyde-3-phosphate dehydrogenase (GAP or GAPDH), hexokinase, phosphofructokinase, 3-glycerophosphate mutase, and pyruvate kinase (PyK) (E.P.O. Publication No. 329203). The yeast PHO5 gene, encoding acid phosphatase, also provides useful promoter sequences. In addition, synthetic promoters which do not occur in nature also function as yeast promoters. For example, upstream activating sequences (UAS) of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (E.P.O. Publication No. 164556). Furthermore, a yeast promoter can include naturally occurring promoters of non-yeast origin that have the ability to bind yeast RNA polymerase for the appropriate initiation of transcription.

Other control elements which may be included in the yeast expression vector are terminators (e.g., from GAPDH, and from the enolase gene (Holland (1981), J. Biol. Chem. 256: 1385), and leader sequences. The leader sequence fragment typically encodes a signal peptide comprised of hydrophobic amino acids which direct the secretion of the protein from the cell. DNA encoding suitable signal sequences can be derived from genes for secreted yeast proteins, such as the yeast invertase gene (E.P.O. Publication No. 12,873) and the α-factor gene (U.S. Pat. No. 4,588,684). Alternatively, leaders of non-yeast origin, such as an interferon leader, also provide for secretion in yeast (E.P.O. Publication No. 60057). A preferred class of secretion leaders are those that employ a fragment of the yeast α-factor gene, which contains both a "pre" signal sequence, and a "pro" region. The types of α-factor fragments that can be employed include the full-length pre-pro α-factor leader, as well as truncated α-factor leaders (U.S. Pat. Nos. 4,546,083 and 4,870,008; E.P.O. Publication No. 324274. Additional leaders employing an α-factor leader fragment that provides for secretion include hybrid α-factor leaders made with a pre-sequence of a first yeast, but a pro- region from a second yeast α-factor. (See, e.g., P.C.T. WO 89/02463).

Expression vectors, either extrachromosomal replicons or integrating vectors, have been developed for transformation into many yeasts. For example, expression vectors have been developed for *Candida albicans* (Kurtz et al. (1986), Mol. Cell Biol. 6: 142), *Candida maltosa* (Kunze et al. (1985) J. Basic Microbiol. 25: 141), *Hanzenula polymorpha* (Gleeson et al. (1986), J. Gen. Microbiol. 132: 3459), *Kluyveromyces fragilis* (Das et al. (1984), J. Bacteriol. 158: 1165), *Kluyveromyces lactis* (De Louvencourt et al. (1983), J. Bacteriol. 154: 737), *Pichia quillerimondii,* (Kunze et al. (1985), supra), *Pichia pastoris* (Cregg et al. (1985), Mol. Cell. Biol. 5: 3376; U.S. Pat. Nos. 4,837,148 and 4,929,555) ), *Schizosaccharomyces pombe* (Beach and Nurse (1981), Nature 300: 706), and *Yarrowia lipolytica* (Davidow et al. (1985), Curr. Genet. 10: 39).

Mammalian cell lines available as hosts for expression are known in the art and include many immortalized cell lines available from the American Type Culture Collection (ATCC), including, for example, HeLa cells, Chinese hamster ovary (CHO) cells, baby hamster kidney (BHK) cells, COS monkey cells, and a number of other cell lines. Suitable promoters for mammalian cells are also known in the art and include viral promoters such as that from Simian Virus 40 (SV40), Rous sarcoma virus (RSV), adenovirus (ADV) and bovine papilloma virus (BPV) (See, Sambrook (1989) for examples of suitable promoters). Mammalian cells may also require terminator sequences and poly A addition sequences; enhancer sequences which increase expression may also be included, and sequences which cause amplification of the gene may also be desirable. These sequences are known in the art.

Vectors suitable for replication in mammalian cells are known in the art, and may include viral replicons, or sequences which ensure integration of the appropriate sequences encoding the desired polypeptides into the host genome.

A vector which is used to express foreign DNA and which may be used in vaccine preparation is Vaccinia virus. In this case, the heterologous DNA is inserted into the Vaccinia genome. Techniques for the insertion of foreign DNA into the vaccinia virus genome are known in the art, and utilize, for example, homologous recombination. The insertion of the heterologous DNA is generally into a gene which is non-essential in nature, for example, the thymidine kinase gene (tk), which also provides a selectable marker. Plasmid vectors that greatly facilitate the construction of recombinant viruses have been described (see, for example, Mackett et al. (1984) in "DNA Cloning", Vol. II. IRL Press, p. 191, Chakrabarti et al. (1985), Mol. Cell Biol. 5: 3403; Moss (1987) in "Gene Transfer Vectors for Mammalian Cells" (Miller and Calos, eds., p. 10). Expression of the desired polypeptides comprised of immunoreactive regions then occurs in cells or individuals which are infected and/or immunized with the live recombinant vaccinia virus.

Other systems for expression of polypeptides include insect cells and vectors suitable for use in these cells. These systems are known in the art, and include, for example, insect expression transfer vectors derived from the baculovirus *Autographa californica* nuclear polyhedrosis virus (AcNPV), which is a helper-independent, viral expression vector. Expression vectors derived from this system usually use the strong viral polyhedron gene promoter to drive expression of heterologous genes. Currently the most commonly used transfer vector for introducing foreign genes into AcNPV is pAc373. Many other vectors, known to those of skill in the art, have also been designed for improved expression. These include, for example, pVL985 (which alters the polyhedron start codon from ATG to ATT, and which introduces a BamHI cloning site 32 basepairs downstream from the ATT; See Luckow and Summers (1989), Virology 17: 31. Good expression of nonfused foreign proteins usually requires foreign genes that ideally have a short leader sequence containing suitable translation initiation signals preceding an ATG start signal. The plasmid also contains the polyhedron polyadenylation signal and the ampicillin-resistance (amp) gene and origin of replication for selection and propagation in *E. coli.*

Methods for the introduction of heterologous DNA into the desired site in the baculovirus are known in the art. (See Summers and Smith, Texas Agricultural Experiment Station Bulletin No. 1555; Ju et al. (1987), in "Gene Transfer Vectors for Mammalian Cells (Miller and Calos, eds.); Smith et al. (1983), Mol. & Cell. Biol. 3: 2156; and Luckow and Summers (1989), supra). For example, the insertion can be into a gene such as the polyhedron gene, by homologous recombination; insertion can also be into a restriction enzyme site engineered into the desired baculovirus gene. The inserted sequences may be those which encode all or varying segments of the desired HCV polypeptides including at least one epitope from a variable domain.

The signals for posttranslational modifications, such as signal peptide cleavage, proteolytic cleavage, and phosphorylation, appear to be recognized by insect cells. The signals required for secretion and nuclear accumulation also appear to be conserved between the invertebrate and vertebrate cells. Examples of the signal sequences from vertebrate cells which are effective in invertebrate cells are known in the art, for example, the human interleukin 2 signal ($IL2_s$) which is a signal for transport out of the cell, is recognized and properly removed in insect cells.

It is often desirable that the polypeptides prepared using the above host cells and vectors be fusion polypeptides. As with non-fusion polypeptides, fusion polypeptides may remain intracellular after expression. Alternatively, fusion proteins can also be secreted from the cell into the growth medium if they are comprised of a leader sequence fragment. Preferably, there are processing sites between the leader fragment and the remainder of the foreign gene that can be cleaved either in vivo or in vitro.

In cases where the composition is to be used for treatment of HCV, it is desirable that the composition be immunogenic. In instances wherein the synthesized polypeptide is correctly configured so as to provide the correct epitope, but is too small to be immunogenic, the polypeptide may be linked to a suitable carrier. A number of techniques for obtaining such linkage are known in the art, including the formation of disulfide linkages using N-succinimidyl-3-(2-pyridyl-thio)propionate (SPDP) and succinimidyl 4-(N-maleimidomethyl)cyclohexane-1-carboxylate (SMCC) (if the peptide lacks a sulfhydryl group, this can be provided by addition of a cysteine residue.) These reagents create a disulfide linkage between themselves and peptide cysteine resides on one protein and an amide linkage through the α-amino on a lysine, or other free amino group in other amino acids. A variety of such disulfide/amide-forming agents are known. See, for example, Immun. Rev. (1982) 62: 185. Other bifunctional coupling agents from a thioether rather than a disulfide linkage. Many of these thio-ether-forming agents are commercially available and include reactive esters of 6-maleimidocaproic acid, 2-bromoacetic acid, 2-iodoacetic acid, 4-(N-maleimidomethyl) cyclohexane- 1-carboxylic acid, and the like. The carboxyl groups can be activated by combining them with succinimide or 1-hydroxyl-2-nitro-4-sulfonic acid, sodium salt. Additional methods of coupling antigens employ the rotavirus/"binding peptide" system described in EPO Publication No. 259,149. The foregoing list is not meant to be exhaustive, and modifications of the named compounds can clearly be used.

Any carrier may be used which does not itself induce the production of antibodies harmful to the host. Suitable carriers are typically large, slowly metabolized macromolecules such as proteins; polysaccharides such as latex functionalized sepharose, agarose, cellulose, cellulose beads and the like; polymeric amino acids, such as polyglutamic acid, polylysine, and the like; amino acid copolymers; and inactive virus particles (see infra.). Especially useful protein substrates are serum albumins, keyhole limpet hemocyanin, immunoglobulin molecules, thyroglobulin, ovalbumin, tetanus toxoid, and other proteins well known to those of skill in the art.

The immunogenicity of the epitopes of the HCV variable domains, particularly of E1 and E2/NS1, may also be enhanced by preparing them in eukaryotic systems fused with or assembled with particle-forming proteins such as, for example, that associated with hepatitis B surface antigen. See, e.g., U.S. Pat. No. 4,722,840. Constructs wherein the polypeptide containing the HCV epitope from a variable domain is linked directly to the particle-forming protein coding sequences produces hybrids which are immunogenic with respect to the HCV epitope. In addition, all of the vectors prepared include epitopes specific to HBV, having various degrees of immunogenicity, such as, for example, the pre-S peptide. Thus, particles constructed from particle forming protein which include HCV sequences are immunogenic with respect to HCV and HBV.

Hepatitis surface antigen (HBSAg) has been shown to be formed and assembled into particles in *S. cerevisiae* (Valenzuela et al. (1982), Nature 298: 344, as well as in, for example, mammalian cells (Valenzuela et al. (1984), in "Hepatitis B", Millman I. et al., ed.). The formation of such particles has been shown to enhance the immunogenicity of the monomer subunit. The constructs may also include the immunodominant epitope of HBSAg, comprising the 55 amino acids of the presurface (pre-S) region. Neurath et al. (1984). Constructs of the pre-S-HBSAg particle expressible in yeast are disclosed in E.P.O. Publication No. 174,444; hybrids including heterologous viral sequences for yeast expression are disclosed in E.P.O. Publication No. 175,261. These constructs may also be expressed in mammalian cells such as CHO cells using an SV40-dihydrofolate reductase vector (Michelle et al. (1984)).

In addition, portions of the particle-forming protein coding sequence may be replaced with codons encoding an epitope from an HCV variable domain. In this replacement, regions which are not required to mediate the aggregation of the units to form immunogenic particles in yeast or mammals can be deleted, thus eliminating additional HBV antigenic sites from competition with the HCV epitope(s).

The preparation of vaccines which contain an immunogenic polypeptide(s) as an active ingredient(s) is known to one skilled in the art. Typically, such vaccines are prepared as injectables, either as liquid solutions or suspensions; solid forms suitable for solution in, or suspension in, liquid prior to injection may also be prepared the preparation may also be emulsified, or the polypeptide(s) encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include, but are not limited to: aluminum hydroxide, N-acetyl-muramyl-L-threonyl-D-isoglutamine (thr-MDP), N-acetyl-nor-muramyl-L-alanyl-D-isoglutamine (CGP 11637), referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE, and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against an immunogenic polypeptide containing an HCV epitope from a variable domain, the antibodies resulting from administration of this polypeptide in vaccines which are also comprised of the various adjuvants.

The proteins may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%–95% of active ingredient, preferably 25%–70%.

In addition to the above, it is also possible to prepare live vaccines of attenuated microorganisms which express recombinant polypeptides of the HCV antigen sets. Suitable attenuated microorganisms are known in the art and include, for example, viruses (e.g., vaccinia virus) as well as bacteria.

The vaccines are administered in a manner compatible with the dosage formulation, and in such amount as will be prophylactically and/or therapeutically effective. The quantity to be administered, which is generally in the range of 5 μg to 250 μg of antigen per dose, depends on the subject to be treated, capacity of the subject's immune system to synthesize antibodies, and the degree of protection desired. Precise amounts of active ingredient required to be administered may depend on the judgment of the practitioner and may be peculiar to each individual.

The vaccine may be given in a single dose schedule, or preferably in a multiple dose schedule. A multiple dose schedule is one in which a primary course of vaccination may be with 1–10 separate doses, followed by other doses given at subsequent time intervals required to maintain and/or reenforce the immune response, for example, at 1–4 months for a second dose, and if needed, a subsequent dose(s) after several months. The dosage regimen will also, at least in part, be determined by the need of the individual and be dependent upon the judgment of the practitioner.

In addition, the vaccine containing the antigen sets comprised of HCV polypeptides described above, may be administered in conjunction with other immunoregulatory agents, for example, immune globulins.

The compositions of the present invention can be administered to individuals to generate polyclonal antibodies (purified or isolated from serum using conventional techniques) which can then be used in a number of applications. For example, the polyclonal antibodies can be used to passively immunize an individual, or as immunochemical reagents.

In another embodiment of the invention, the above-described immunoreactive compositions comprised of a plurality of HCV antigen sets are used to detect anti-HCV antibodies within biological samples, including for example, blood or serum samples. Design of the immunoassays is subject to a great deal of variation, and a variety of these are known in the art However, the immunoassay will use antigen sets wherein each antigen set consists of a plurality of substantially identical polypeptides comprising the amino acid sequence of an epitope within a first variable domain of an HCV isolate, and the amino acid sequence of one set is heterogeneous with respect to the amino acid sequence of at least one other set. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention containing HCV epitopes from variable domains, in suitable containers, along with the remaining reagents and materials (for example, suitable buffers, salt solutions, etc) required for the conduct of the assay, as well as a suitable set of assay instructions.

Described below are examples of the present invention which are provided only for illustrative purposes, and not to limit the scope of the present invention. In light of the present disclosure, numerous embodiments within the scope of the claims will be apparent to those of ordinary skill in the art.

EXAMPLES

In the Examples the following materials and methods were used.

Patient Samples and RNA Extraction

Asymptomatic HCV carriers HCT 18 and HCV J1 and chronically infected HCV patient Th have been previously described in Weiner et al. (1991) *Virol.* 180: 842–848. Patient Q was diagnosed with chronic active hepatitis based on a liver biopsy and was placed on alfa-2b interferon therapy (3 million units, thrice weekly) for six months. RNA from 0.2 ml of plasma was extracted according to the method of Chomcynski and Sacchi, (1987) Anal. Biochem. 162: 156–159, using RNAzol™ B reagent (Cinna/Biotecx Laboratories) containing 10 μg/ml MS2 carrier RNA (Boehringer Mannheim, 165–948) as indicated by the manufacturer. RNA was resuspended in 200 μl of diethyl pyrocarbonate treated distilled water and reprecipitated in a final concentration of 0.2M sodium acetate and two and one half volumes of 100% ethanol (−20° C.).

cDNA and Polymerase Chain Reactions

All reactions were performed according to Weiner et al. (1990) Lancet 335: 1–5. M13 sequencing was performed according to Messing et al. (1983), Methods in Enzymology 101: 20–37. The consensus sequence of at least four cloned inserts are presented with the exception of the HCV J1.2 E2/NS1 sequence which was derived from two clones.

Cloning and sequencing of HCT 18 and Th was as reported in Weiner et al. (1991), supra. Nested PCR primers used to clone the amino terminal and carboxy proximal segments of E2/NS1 in patient Q were: PCR I
X(E2)14 GGTGCTCACTGGGGAGTCCT(1367–1386)S
X(E2)18J CATTGCAGTTCAGGGCCGTGCTA (1608–1588)A, PCR II X(E2)4 TCCATGGTGGGGAACTGGGC(1406–1425)S
X(E2)19J TGCCAACTGCCATTGGTGTT(1582–1562)A; PCR I
X(E2)14 (above)S
J1rc12 TAACGGGCTGAGCTCGGA(2313–2296)A PCR II
US(E2)5 CAATTGGTTCGGTTGTACC(1960–1978)S
J1rc13 CGTCCAGTTGCAGGCAGCTTC(2260–2240)A.
PCR primers used to clone the HCV J1 E2/NS1 gene were:
PCR I
J1(E2)14 (above)S
J1(E2)rc30** CAGGGCAGTATCTGCCACTC (2349–2330)A
J1IZ-2* TGAGACGGACGTGCTGCTCCT(1960–1978)S
J1(E2)rc32** TTTGATGTACCAGGCGGCGCA (2658–2636)A PCR II-E2384.5*
GGATCCGCTAGCCATACCCGCGTGACGGGGGGGG-TGCAA(1469–1495)S
DSCON1JBX*
GGATCCTCTAGATTACTCTTCTGAC-CTATCCCTGTCCTCCAAGTC
ACA(2272–2301)A
J1IZ-1* CAACTGGTTCGGCTGTACA(1915–1935)S
J1(E2)rc31** (2566–2546)A.

*, nt sequence from Takeuchi et al., (1990) Nucl. Acids Res. 18: 4626; **, nt sequence from Kato et al., (1989) Proc. Jpn. Acad. 65B: 219–223. Sense (S) or antisense (A) PCR primers are given in the 5' to 3' orientation according nucleotide numbers in reference.

Synthesis of Biotinylated Peptides

The overlapping octapeptides for the hypervariable regions of three strains of HCV were synthesized on cleavable-linker, derivatized, polyethylene pins essentially as described by (Maeji et al., (1990) J. Immunol. Methods 134: 23–33, was coupled to the N-terminus of each peptide. Finally, biotin was coupled to the N-terminus using 150 µl of a dimethylformamide solution containing 40 mM biotin, 40 mM 1-hydroxybenzotriazole (HOBt), 40 mM benzotriazole-1-yl-oxy-tris-pyrrlidino-phosphonium hexafluorophosphate (PYBOP, NOVABIOCHEM) and 60 mM N-methylmorpholine (NMM) reacting overnight at 20° C.

After biotinylation, the peptides were side-chain deprotected, washed and the peptide from each pin was cleaved in 200 µl of 0.1M phosphate buffer (pH 7.2). Microtitre plates containing the cleaved peptide solutions were stored at –20° C. until needed.

ELISA Testing of Biotinylated Peptides

Polystyrene plates (Nunc immuno plate maxisorb F96) were coated with streptavidin by incubating overnight at 4° C. with 0.1 ml/well of a 5 µg/ml solution of streptavidin (Sigma Cat. No. S4762) in 0.1M carbonate buffer at pH 9.6. After removal of the streptavidin solution, the wells were washed four times with a 0.1% solution of Tween 20 in PBS. Nonspecific binding was blocked by incubating each well with 0.2 ml of 2% BSA in PBS for 1 h at 20° C. The wells were again washed four times with PBS/Tween 20. Plates were air-dried and stored at 4° C. until required. The streptavidin in each well was coupled to cleaved peptides by incubation with 100 µl of a 1: 100 dilution of cleaved peptide solution with 0.1% BSA in PBS containing 0.1% sodium azide for 1 h at 20° C. After incubation, the plate was washed four times with PBS/Tween 20. Each well was incubated with 100 µl of a suitable dilution of serum (diluted with 2% BSA in PBS containing 0.1% sodium azide) for 1 h at 20° C. or overnight at 4° C. followed by four washes with PBS/Tween 20. Bound antibody was detected by reaction for 1 h at 20° C. in 0.1 ml conjugate. This consisted of 0.25 ml/l (a saturating level) of horseradish peroxidase-labeled goat anti-rabbit IgG (H+L) (Kirkegaard and Perry Labs, Gaithersburg, Md.) in CASS (0.1% sheep serum, 0.1% Tween 20, 0.1% sodium caseinate diluted in 0.1M PBS, pH 7.2). The wells were washed 2 times with PBS/Tween 20 followed by two washes with PBS only. The presence of enzyme was detected by reaction for 45 min at 20° C. with 0.1 ml of a freshly-prepared solution containing 50 mg of ammonium 2,2'-azino-bis[3-ethylbenzothiazoline-6-sulphonate (ABTS, Boehringer Mannheim Cat. no. 122661) and 0.03 ml of 35% (w/w) hydrogen peroxide solution in 100 ml of 0.1M phosphate/0.08M citrate buffer, pH 4.0. Color development was measured in a Titertek Multiscan MC plate reader in the dual wavelength mode at 405 nm against a reference wavelength of 492 nm.

Computer Generated Antigenicity Profile

Antigenicity profiles for the HCV E2/NS1 protein and HIV-1 gp120 hypervariable region V3 (aa 303–338) were derived from a computer program based on the degree of sequence variability as originally proposed by Kabat [Sequences of proteins of immunological interest. U.S. Department of Health and Human Services, Public Health Service, National Institutes of Health (1983)] for the identification of the hypervariable loops of immunoglobulins multiplied by the average of the individual probability that antibody binding is retained for each possible pair-wise amino acid. Probabilities for retention of antibody binding associated with a given amino acid change were the values experimentally determined by assessing the effects on antibody binding of all possible amino acid substitutions for 103 characterized linear epitopes. Geysen et al., (1988) J. Mol. Rec. 1: 32–41. This algorithm thus weights the variability index to give more significance to amino acid changes likely to have a significant effect on antibody binding, i.e., compensates for conservative amino acid changes. Fifteen HCV sequences [HCV-1, Q3.2, HCT 23, EC10, HC-J1, HCVE1, TH, HCT 27, Q1.2, HCT18, HC-J4, HCV J1.2/HCV J1.1, HCV J , HCV BK], were used to determine the antigenicity profile for HCV. The HIV-1 V3 profile was obtained by averaging 242 individual profiles of 15 sequences selected at random from the numerically greater data base of unique HIV-1 sequences. LaRosa et al., (1990) Science 249: 932–935 & Correction in Science (1991) p. 811. The amino acid sequences of some of these isolates between aa 384 and 420 are shown in FIG. 3.

Computer Generated Secondary Structure Predictions

The α-helix, β-sheet and β-turn secondary structure probabilities for the amino-terminal region (384–420) were determined using an algorithm, which assigns the probabilities for each of the three above secondary structural motifs to each residue. The coefficients used in the algorithm were obtained for all pair-wise combinations of residues of the structural data base. Levitt and Greer, (1977) J. Mol. Biol. 114: 181–293. The prediction parameters obtained from these coefficients were fitted to the observed outcome when the algorithm was applied back on the database to obtain probabilities that a given residue would be found in one of the three defined secondary structural motifs.

EXAMPLE 1

Figure 4A:
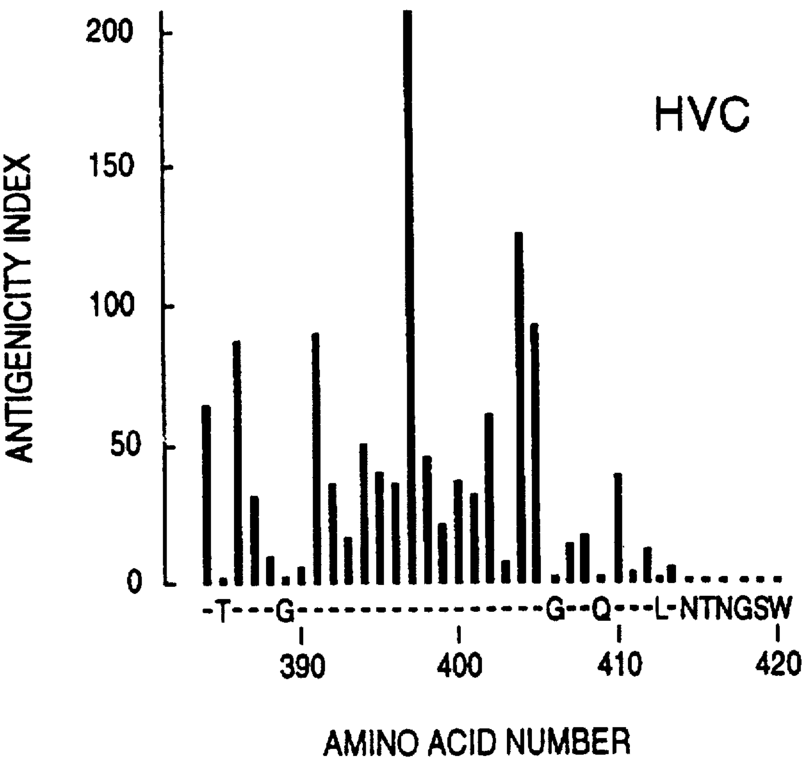
FIG. 4 are graphs showing the antigenicity profiles for the amino-terminal region of the putative HCV E2/NS1 protein (amino acids 384–420), and the gp 120 V3 hypervariable region of HIV-1.
Figure 4B:
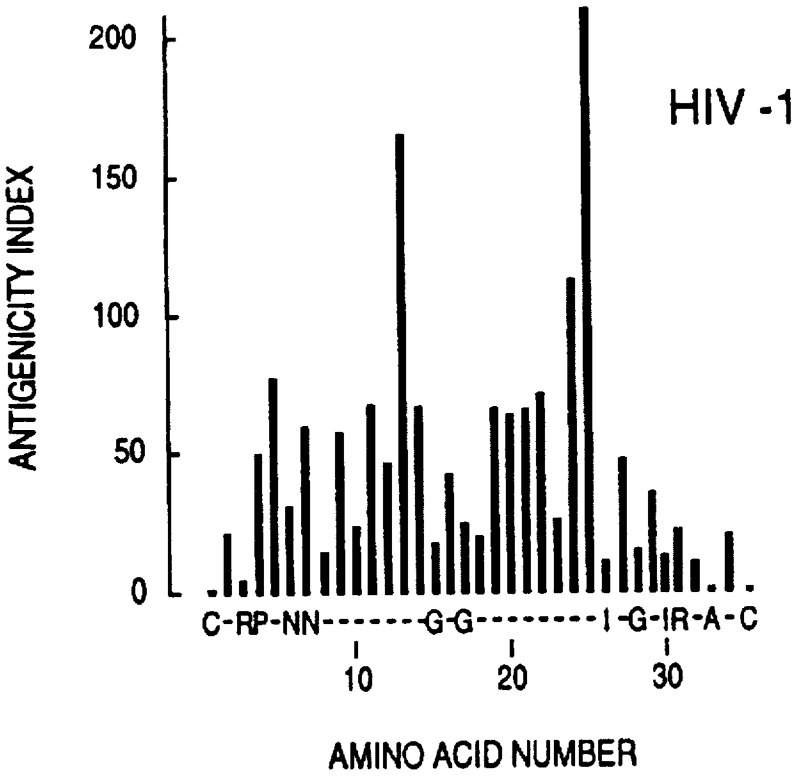
Figure 5A:
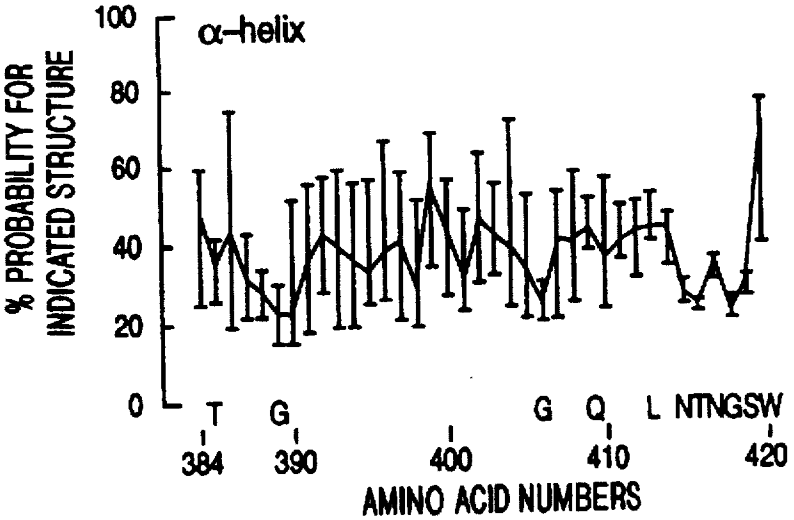
FIG. 5 shows a series of graphs which give the percentage probabilities that a given residue from the amino-terminal region of HCV E2/NS1 protein (amino acids 384 to 420) will be found in either alpha-helix, beta-sheet or beta-turn secondary structural motif.
Figure 5B:
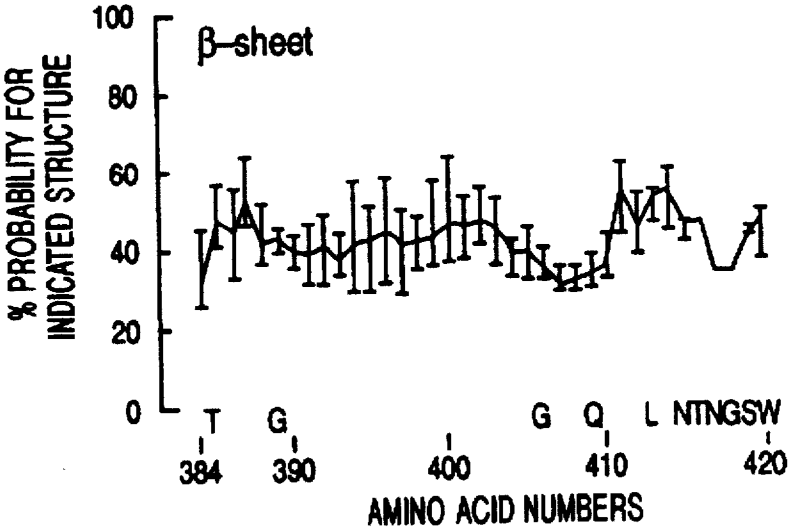
Figure 5C:
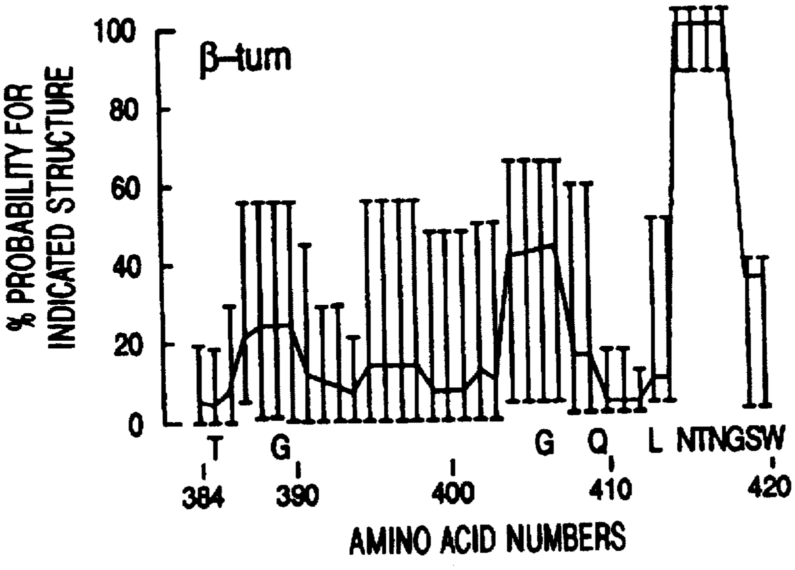

Comparison of Secondary Structure and Amino Acid Sequence Variation in the HCV E2/NS1 HV and HIV-1 gp120 Domains The amino acid sequences from fifteen HCV and HIV-1 isolates were compared with respect to the number of positions at which amino acid sequence heterogeneities were observed in the HCV E2 HV or HIV-1 gp120 V3 domains (FIG. 4, A and B, respectively). Amino acid heterogeneities occurred in 25 of 30 amino acid positions in the E2 HV region and 23 of 35 amino acid positions in the HIV-1 gp120 V3 domain. Dashes on the x-axis of FIGS. 4A and B represent amino acid positions where variable amino acid residues occur and invariant amino acids are given in the single letter amino acid code. The antigenicity profiles shown in FIG. 4 indicate that, similar to the V3 loop of the HIV-1 gp120 protein (FIG. 4B), a block of amino acid residues in the HCV E2 (amino acids 384–414 in FIG. 4A) was identified whose variation had a predicted adverse affect on antibody binding. The data in FIG. 4 indicate that the HCV E2 domain resembles the HIV-1 gp120 V3 domain, which is known to encode virus neutralizing epitopes, in both the degree and predicted significance of observed amino acid variation and suggests that the E2 HV domain may have a similar function as the gp120 V3 domain.

Linear epitopes are more likely associated with less structured regions of proteins, in particular, the ends of proteins or with extended surface loops. A computer analysis was used to predict the probability that an individual residue is associated with a defined secondary structural motif for 15 E2 HV amino acid sequences between residues 384 to 420. FIG. 4 shows that the region between the E2 amino-terminal residue 384 and the strongly predicted, highly conserved beta-turn (residues 415–418) is relatively unstructured as indicated by less than 50 percent probability of alpha-helix, beta-sheet or beta-turn character. Lack of strongly predictive structure in the E2 HV domain is consistent with the tolerance for extensive sequence variation found between isolates and is in contrast with highly structured regions which contribute to tertiary folding of the protein. The HCV E2 HV domain appears to be even less structured than the V3, principal neutralizing domain of HIV-1 gp120, which has been reported to contain a beta strand-type II beta turn-beta strand-alpha helix motif and may have greater structural constraints on amino acid variability than the HCV E2 HV domain. Taken together, the evidence suggests that the E2 HV domain appears to have features characteristic of protein domains which contain likely sites of linear neutralizing epitopes.

EXAMPLE 2

Epitope Mapping of the HCV E2/NS1 HV Domain

Figure 6A:
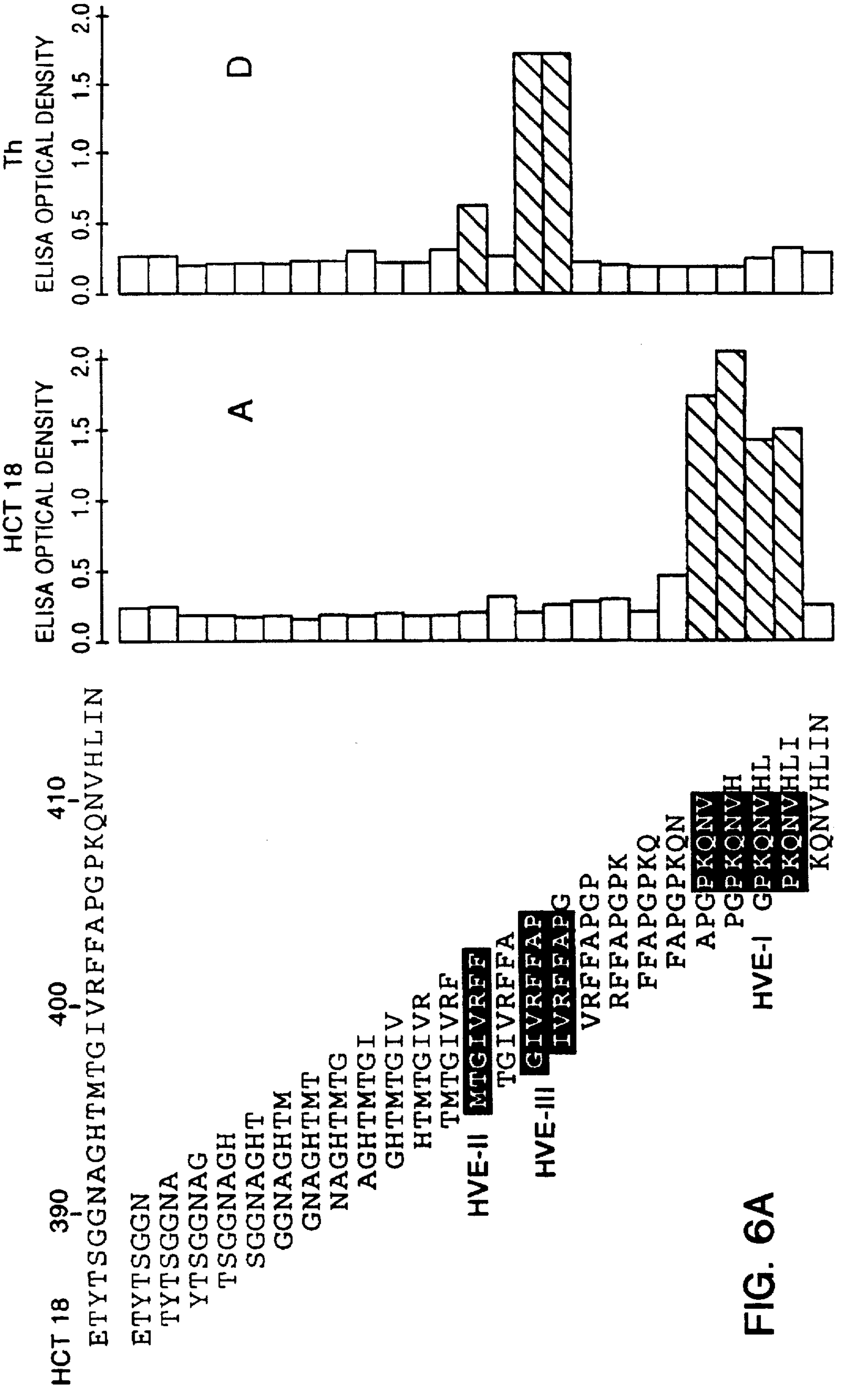
FIG. 6 are bar graphs showing the reactivity of antibodies in the plasma from HCV 18 (panels A-C) or Th (Panels D-f) with overlapping biotinylated 8mer peptides derived from amino acids 384 to 415 or 416 of HCV isolates HCT 18 (A,D), Th (B,E) and HCV J1 (C,F), respectively.
Figure 6B:
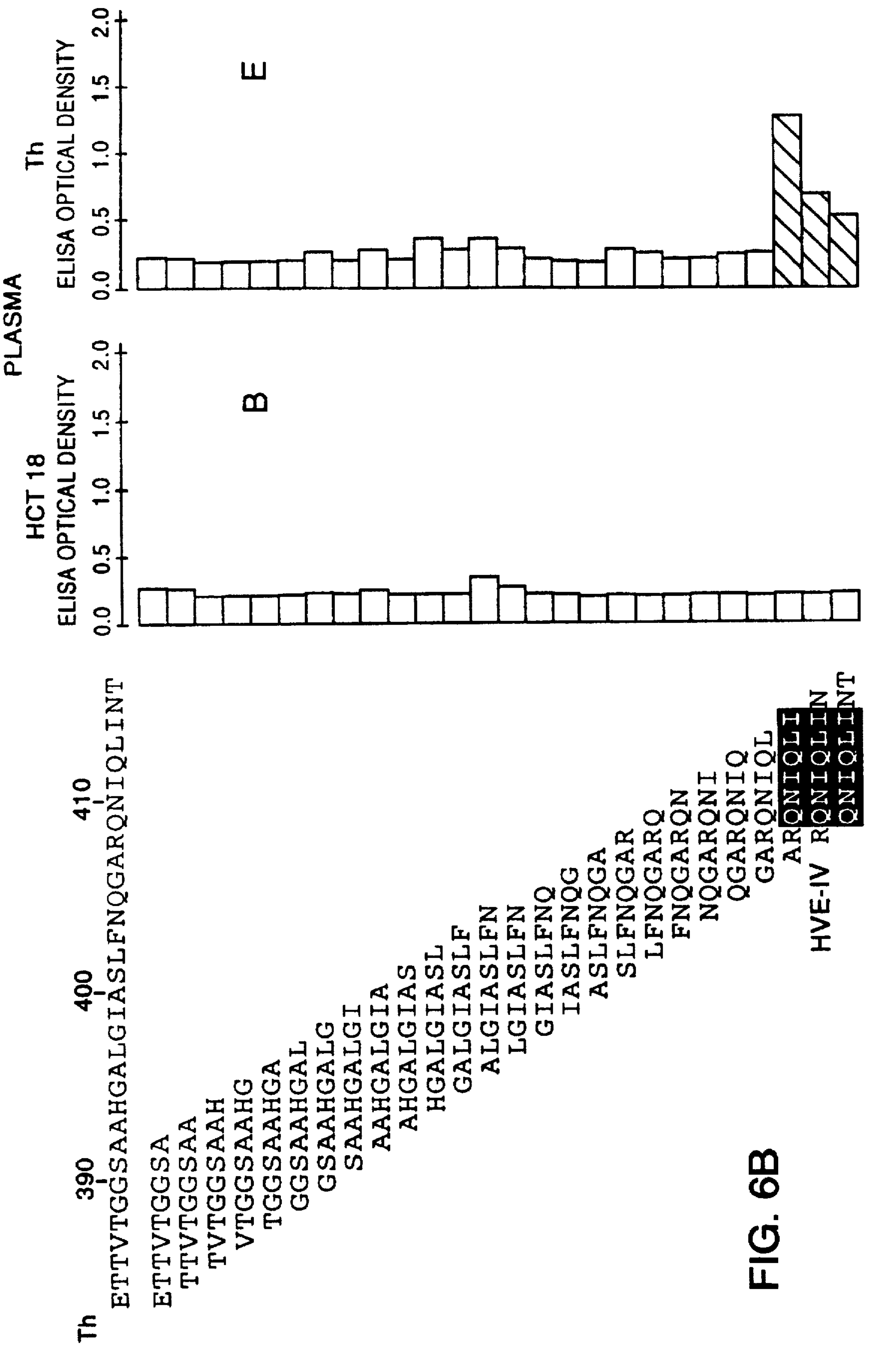
Figure 6C:
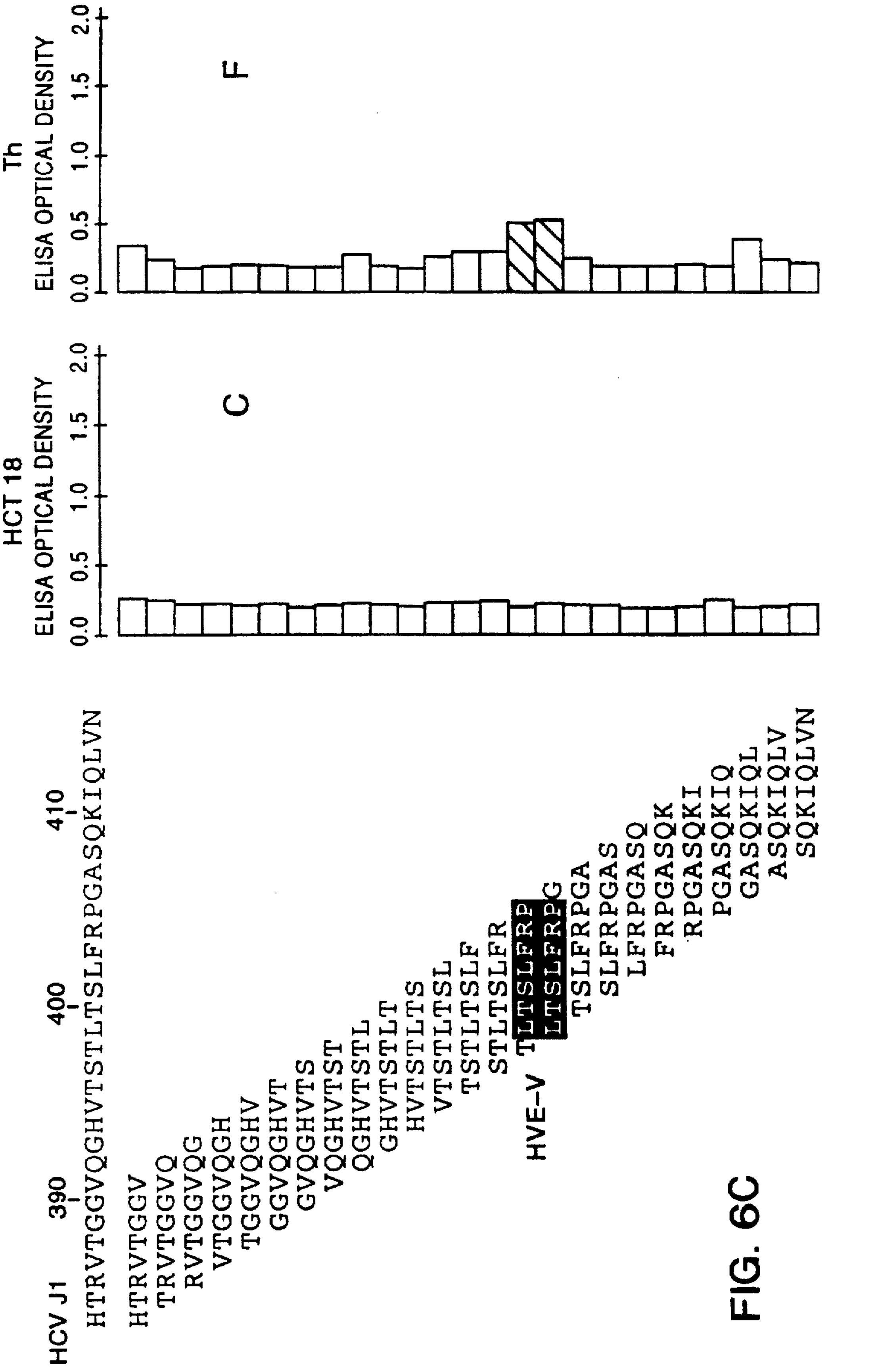

Overlapping biotinylated 8-mer peptides corresponding to and extending past the E2/NS1 HV domain (amino acids 384 to 416) of HCT 18 (A,D), Th (B,E) and HCV J1 (C,F) were bound to plates coated with streptavidin and reacted with plasma from either HCT 18 (A–C) or Th (D–F). The results are shown in FIG. 6 for HCV isolates HCT 18 (FIG. 6A and 6D), Th (FIGS. 6B and 6E), and HCV J1 (FIGS. 6C and 6F). HCT 18 plasma was diluted 1:200 and Th plasma was diluted 1:500. HVE-1, -2, -3, -4 and -5, represent isolate specific epitopes.

As seen from FIG. 6, HCT 18 plasma identified a linear epitope ($^{407}$PKQNV$^{411}$) when tested with peptides derived from the HCT18 sequence (HVE-I in FIG. 6A), but failed to react with peptides corresponding to the HV domain of two different strains Th and HCV J1 (FIGS. 6B and 6C). In contrast, Th plasma identified linear epitope HVE-IV in the HV domain of Th ($^{409}$QNIQLI$^{414}$, FIG. 6E), and also epitopes in strain HCT 18 ($^{399}$IVRFFAP$^{405}$, FIG. 6D) and HCV J1. Th, an IV drug user, may have been exposed to multiple strains of HCV.

Both Th and HCT 18 plasma each reacted with an epitope (amino acids 413–419) common to all three isolates (data not shown) when used in an ELISA with pin synthesized overlapping 8mer peptides from each isolate.

In order to validate antibody binding specificity, antibodies bound to biotinylated peptides containing amino acids 403–407 were eluted and used to block the reactivity of HCT 18 plasma with pins containing overlapping 8-mers for the HCT 18 HV domain. These data indicate that 1) the E2/NS1 HV domain is immunogenic, 2) there are multiple epitopes which map to this region, and 3) a subset of epitopes (HVE-1, -2, -3, -4 or -5 in FIG. 6) in the HV domain are isolate specific.

EXAMPLE 3

Determination that Variant E2/NS1 HV Domains Can Be Associated With Flares of Hepatitis To investigate the possibility of finding HCV variants associated with the intermittent flares of hepatitis often found in chronic HCV infections, we partially sequenced the E2/NS1 gene from a patient, Q, with chronic hepatitis during two distinct episodes of hepatitis approximately two years apart (Q1 and Q3, respectively). The second episode of hepatitis occurred 1.5 years after the termination of interferon treatment.

Figure 7:
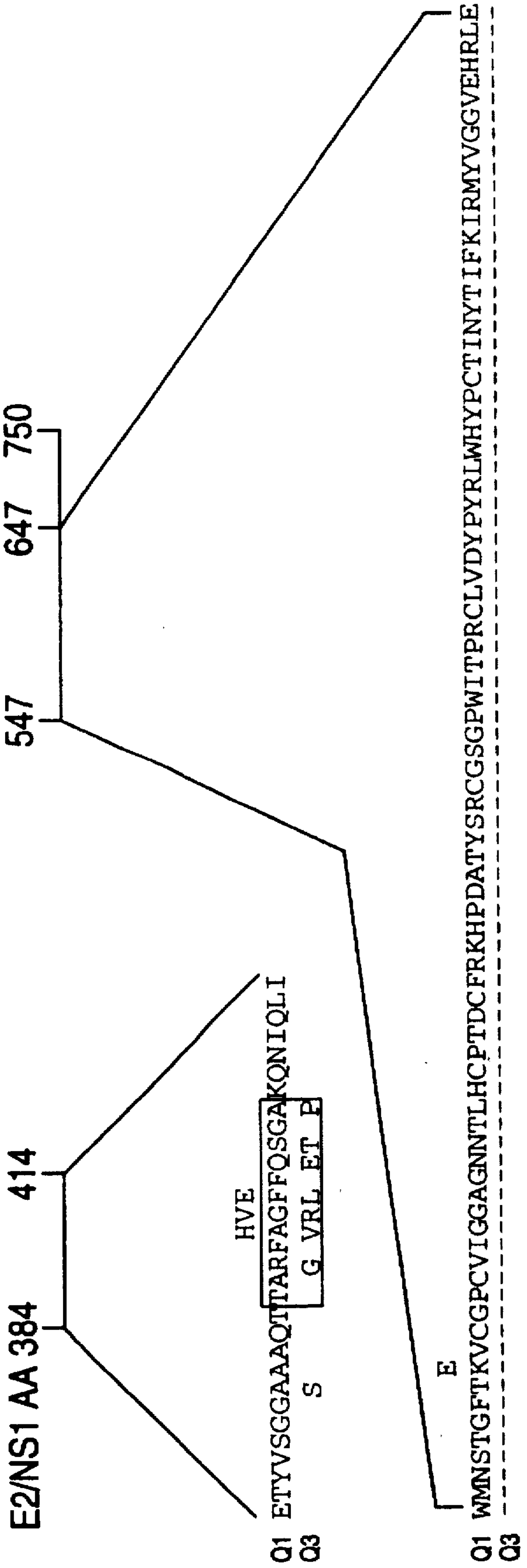
FIG. 7 shows the deduced amino acid sequences of two regions of the E2/NS1 polypeptide, amino acids 384–414 and 547–647, given for the Q1 and Q3 isolates.

The differences in the deduced amino acid sequence of the Q1 and Q3 E2/NS1 HV region was strikingly different only between amino acids 391–408 with seven of eight changes occurring between amino acid 398 and 407 (FIG. 7). FIG. 7 shows the deduced amino acid sequences of two regions of the E2/NS1 polypeptide, amino acids 384–414 and 547–647, for the Q1 and Q3 isolates. The amino acid (E) above the Q1 sequence was found in one of four Q1 clones. The boxed amino acids represent the location of the Q1 or Q3 HVE 12mer peptide. Amino acid sequence differences found between Q1 and Q3 are printed in bold type.

Only one amino acid heterogeneity was observed between amino acids 547 and 647 of the Q1 and Q3 E2/NS1 polypeptides (FIG. 7).

To examine the effect of the amino acid substitutions observed in the Q1 and Q3 E2 HV domains on antibody binding, we synthesized a Q1 and Q3 specific 12-mer peptide from amino acids 396 to 407 (HVE Q1 or Q3 in FIG. 7B) and separately reacted the Q1 and Q3 plasma with each peptide in an ELISA. Table 4 shows that antibodies in both the Q1 and Q3 plasma reacted with the Q1 peptide but not with the Q3 peptide. Statistical analysis (Student's Test) indicated that the binding of the Q1/Q3 plasma to the Q1 peptide was significantly above background binding of those plasma to a panel of 12 randomly chosen control peptides ($P<0.001$), while binding of either the Q1 or Q3 plasma to the Q3 peptide was not statistically significant. The data indicate that although patient Q developed antibodies to the HCV Q1 HV domain, which were still detectable two years later at the Q3 time point, no detectable humoral response had developed to the Q3 E2 HV variant which was predominant during the second episode of hepatitis.

TABLE 4

Elisa Results on 12-mer Peptides

| | TARFAGFFQSGA Q1 seq | | TAGFVRLFETGP Q3 seq | |
|---|---|---|---|---|
| Plasma | Mean | sd | Mean | sd |
| Q1 | 1.158 | 0.134 | 0.691 | 0.123 |
| Q3 | 1.022 | 0.123 | 0.693 | 0.036 |

EXAMPLE 4

Detection of Coexisting E2/NS1 Genes With Distinct E2/NS1 HV Domains in HCV Infected Individuals FIG. 8A shows the amino acid sequences deduced from two isolates of HCV J1 (J1.1 & J1.2) which were cloned from one plasma sample of the Japanese volunteer blood donor HCV J1. Kubo et al., (1989) Nucl. Acids Res. 17: 10367–10372. Of the 23 total amino acid changes between HCV J1.1 and HCV J1.2, 9 differences indicated by bold type are clustered in the 30 amino acid E2/NS1 HV domain. Five of the 9 amino acid substitutions in the E2/NS1 HV domain represent nonconservative amino acid changes. Since HCV J1 is the only group II HCV genome which has been cloned in our laboratory, it is unlikely that these differences are due to cross contamination of the HCV J1 plasma. The HCV J1.2 sequence represents a minority sequence in HCV J1's blood since only two E2/NS1 HV variant sequences were identified from 7 cloned sequences which originated from two independent PCR reactions.

Interestingly, a comparison of the HCT27 and HCV E1 isolates (FIG. 8B), which were sequenced in different laboratories and derive from presumably unrelated individuals, showed that the number of amino acid differences in the E2/NS1 HV domain of these isolates were fewer than the number of differences observed between isolates from the same individual.

The above described results lead to the suggestion that the HCV genome is rapidly evolving in individuals and the population.

Industrial Utility

The immunoreactive compositions of the invention, have utility in the preparation of materials, for example, vaccines, which in turn may be used for the treatment of individuals against HCV infections, particularly chronic HCV infections. In addition, the compositions may be used to prepare materials for the detection of multiple variants of HCV in biological samples. For example, the immunoreactive compositions of the present invention can be used to generate polyclonal antibody compositions that recognize more than one HCV isolate, or as the antigen in an anti-HCV antibody immunoassay. The latter method can be used to screen blood products for possible HCV contamination. Polyclonal antiserum or antibodies can be used to for passive immunization of an individual.

What is claimed is:

1. A DNA molecule encoding a polypeptide comprising two heterogeneous amino acid sequences from the same variable domain of distinct HCV isolates.

2. A host cell comprising a DNA molecule according to claim 1.

3. A host cell according to claim 2 wherein the DNA molecule comprises control sequences that are capable of causing the expression of the polypeptide.

4. A method of making a recombinant protein comprising growing a population of host cells according to claim 3 under conditions that provide for the expression of the polypeptide.

5. A DNA molecule encoding a polypeptide comprising two heterogeneous amino acid sequences from the same variable domain of distinct HCV isolates, wherein the variable domain is selected from the group consisting of the E1 or E2/NS1 domains.

6. A host cell comprising a DNA molecule according to claim 5.

7. A host cell according to claim 6 wherein the DNA molecule comprises control sequences that are capable of causing the expression of the polypeptide.

8. A method of making a recombinant protein comprising growing a population of host cells according to claim 7 under conditions that provide for the expression of the polypeptide.

* * * * *